(12) United States Patent
Burja et al.

(10) Patent No.: US 9,719,116 B2
(45) Date of Patent: *Aug. 1, 2017

(54) EUKARYOTIC MICROORGANISMS FOR PRODUCING LIPIDS AND ANTIOXIDANTS

(71) Applicant: DSM NUTRITIONAL PRODUCTS AG, Kaiseraugst (CH)

(72) Inventors: Adam M. Burja, Palo Alto, CA (US); Helia Radianingtyas, Palo Alto, CA (US); Colin James Barrow, Torquay (AU); Anthony James Windust, Kars (CA)

(73) Assignee: DSM NUTRITIONAL PRODCUTS AG, Kaiseraugst (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,316

(22) Filed: Nov. 18, 2014

(65) Prior Publication Data

US 2015/0218603 A1    Aug. 6, 2015

Related U.S. Application Data

(63) Continuation of application No. 13/427,562, filed on Mar. 22, 2012, now Pat. No. 8,921,069, which is a continuation of application No. 11/916,781, filed as application No. PCT/IB2006/003977 on Jun. 7, 2006, now Pat. No. 8,163,515.

(60) Provisional application No. 60/751,401, filed on Dec. 16, 2005, provisional application No. 60/688,207, filed on Jun. 7, 2005.

(51) Int. Cl.
| | | |
|---|---|---|
| *C12P 7/64* | (2006.01) | |
| *A21D 8/04* | (2006.01) | |
| *A61K 9/48* | (2006.01) | |
| *A61K 31/20* | (2006.01) | |
| *C12R 1/00* | (2006.01) | |
| *A23K 10/18* | (2016.01) | |
| *A23K 20/158* | (2016.01) | |
| *A23P 10/30* | (2016.01) | |
| *A23L 29/00* | (2016.01) | |
| *A23L 33/115* | (2016.01) | |
| *A23L 33/12* | (2016.01) | |
| *A23L 33/135* | (2016.01) | |

(52) U.S. Cl.
CPC ............. *C12P 7/6427* (2013.01); *A21D 8/04* (2013.01); *A23K 10/18* (2016.05); *A23K 20/158* (2016.05); *A23L 29/065* (2016.08); *A23L 33/115* (2016.08); *A23L 33/12* (2016.08); *A23L 33/135* (2016.08); *A23P 10/30* (2016.08); *A61K 9/4875* (2013.01); *A61K 31/20* (2013.01); *C12R 1/00* (2013.01); *A23V 2002/00* (2013.01)

(58) Field of Classification Search
CPC ......................................................... A21D 8/04
See application file for complete search history.

(56) References Cited

U.S. PATENT DOCUMENTS

| | | |
|---|---|---|
| 2,076,018 A | 4/1937 | Ferguson |
| 4,295,383 A | 10/1981 | Frost |
| 4,341,038 A | 7/1982 | Bloch et al. |
| 4,445,495 A | 5/1984 | Frost |
| 4,680,314 A | 7/1987 | Nonomura |
| 4,952,511 A | 8/1990 | Radmer |
| 5,070,018 A | 12/1991 | Peters et al. |
| 5,104,803 A | 4/1992 | Delente et al. |
| 5,130,242 A | 7/1992 | Barclay et al. |
| 5,151,347 A | 9/1992 | Delente et al. |
| 5,162,051 A | 11/1992 | Hoeksema |
| 5,164,308 A | 11/1992 | Kyle et al. |
| 5,168,056 A | 12/1992 | Frost et al. |
| 5,171,680 A | 12/1992 | Mullenbach et al. |
| 5,211,181 A | 5/1993 | Delente |
| 5,232,565 A | 8/1993 | Zare et al. |
| 5,244,921 A | 9/1993 | Kyle et al. |
| 5,272,073 A | 12/1993 | Frost et al. |
| 5,324,658 A | 6/1994 | Cox et al. |
| 5,327,901 A | 7/1994 | Delente |
| 5,340,594 A | 8/1994 | Barclay et al. |
| 5,340,742 A | 8/1994 | Barclay et al. |
| 5,374,657 A | 12/1994 | Kyle |
| 5,376,540 A | 12/1994 | Kyle et al. |
| 5,393,669 A | 2/1995 | Brown |
| 5,397,591 A | 3/1995 | Kyle et al. |
| 5,407,957 A | 4/1995 | Kyle et al. |
| 5,432,094 A | 7/1995 | Delente |
| 5,466,434 A | 11/1995 | Kyle et al. |
| 5,487,987 A | 1/1996 | Frost et al. |
| 5,492,938 A | 2/1996 | Kyle et al. |
| 5,518,918 A | 5/1996 | Barclay et al. |
| 5,547,699 A | 8/1996 | Iizuka et al. |

(Continued)

FOREIGN PATENT DOCUMENTS

| | | |
|---|---|---|
| CA | 2072978 | 10/2006 |
| DE | 19832784 | 2/2000 |

(Continued)

OTHER PUBLICATIONS

Mexican Application No. MX/a/2012/009979 Office Action mailed Jan. 28, 2015, 5 pages, with English translation.

(Continued)

*Primary Examiner* — Bin Shen
(74) *Attorney, Agent, or Firm* — Kilpatrick Townsend & Stockton, LLP

(57) ABSTRACT

Disclosed are compositions and methods related to eukaryotic microorganisms that can produce unsaturated fatty acids which can be purified and used.

19 Claims, 19 Drawing Sheets

(56) References Cited

U.S. PATENT DOCUMENTS

| | | |
|---|---|---|
| 5,550,156 A | 8/1996 | Kyle |
| 5,567,732 A | 10/1996 | Kyle et al. |
| 5,583,019 A | 12/1996 | Barclay et al. |
| 5,593,853 A | 1/1997 | Chen et al. |
| 5,616,496 A | 4/1997 | Frost et al. |
| 5,627,044 A | 5/1997 | Brown |
| 5,629,181 A | 5/1997 | Frost et al. |
| 5,656,319 A | 8/1997 | Barclay et al. |
| 5,658,767 A | 8/1997 | Kyle |
| 5,688,500 A | 11/1997 | Barclay et al. |
| 5,698,244 A | 12/1997 | Barclay et al. |
| 5,711,983 A | 1/1998 | Kyle et al. |
| 5,741,713 A | 4/1998 | Brown et al. |
| 5,770,598 A | 6/1998 | Miller et al. |
| 5,776,736 A | 7/1998 | Frost et al. |
| 5,798,236 A | 8/1998 | Frost et al. |
| 5,817,474 A | 10/1998 | Brown |
| 5,821,266 A | 10/1998 | Frost |
| 5,882,703 A | 3/1999 | Barclay et al. |
| 5,908,622 A | 6/1999 | Barclay et al. |
| 5,985,348 A | 11/1999 | Barclay |
| 6,027,900 A | 2/2000 | Allnutt et al. |
| 6,054,147 A | 4/2000 | Barclay et al. |
| 6,103,225 A | 8/2000 | Barclay et a. |
| 6,111,066 A | 8/2000 | Anderson et al. |
| 6,140,365 A | 10/2000 | Kiy et al. |
| 6,140,486 A | 10/2000 | Facciotti et al. |
| 6,166,230 A | 12/2000 | Bijl et al. |
| 6,166,231 A | 12/2000 | Hoeksema |
| 6,168,912 B1 | 1/2001 | Chen |
| 6,177,108 B1 | 1/2001 | Barclay |
| 6,180,376 B1 | 1/2001 | Liddell |
| 6,207,808 B1 | 3/2001 | Naae et al. |
| 6,255,505 B1 | 7/2001 | Bijl et al. |
| 6,335,196 B1 | 1/2002 | Anderson et al. |
| 6,340,578 B1 | 1/2002 | Anderson et al. |
| 6,350,890 B1 | 2/2002 | Kiy et al. |
| 6,372,460 B1 | 4/2002 | Gladue et al. |
| 6,372,461 B1 | 4/2002 | Frost |
| 6,376,253 B1 | 4/2002 | Anderson et al. |
| 6,395,778 B1 | 5/2002 | Luthria |
| 6,399,803 B1 | 6/2002 | Corley et al. |
| 6,410,281 B1 | 6/2002 | Barclay |
| 6,410,282 B1 | 6/2002 | Kumar et al. |
| 6,432,468 B1 | 8/2002 | Akimoto et al. |
| 6,441,208 B2 | 8/2002 | Bijl et al. |
| 6,451,567 B1 | 9/2002 | Barclay |
| 6,461,839 B2 | 10/2002 | Yokochi et al. |
| 6,472,169 B1 | 10/2002 | Frost et al. |
| 6,472,190 B1 | 10/2002 | Frost |
| 6,509,178 B1 | 1/2003 | Tanaka et al. |
| 6,541,049 B2 | 4/2003 | Barclay |
| 6,566,123 B1 | 5/2003 | Barclay |
| 6,566,583 B1 | 5/2003 | Facciotti et al. |
| 6,568,351 B1 | 5/2003 | Barclay et al. |
| 6,582,941 B1 | 6/2003 | Yokochi et al. |
| 6,596,766 B1 | 7/2003 | Igarashi et al. |
| 6,600,077 B1 | 7/2003 | Frost et al. |
| 6,607,900 B2 | 8/2003 | Bailey et al. |
| 6,613,552 B1 | 9/2003 | Frost et al. |
| 6,620,602 B2 | 9/2003 | Frost et al. |
| 6,716,460 B2 | 4/2004 | Abril |
| 6,727,373 B2 | 4/2004 | Bijl et al. |
| 6,749,849 B2 | 6/2004 | Barclay |
| 6,750,048 B2 | 6/2004 | Ruecker et al. |
| 6,750,049 B1 | 6/2004 | Frost et al. |
| 6,783,951 B2 | 8/2004 | Long, II |
| 6,812,009 B2 | 11/2004 | Gladue et al. |
| 6,974,592 B2 | 12/2005 | Yan |
| 6,977,167 B2 | 12/2005 | Barclay |
| 7,001,772 B2 | 2/2006 | Roessler et al. |
| 7,005,280 B2 | 2/2006 | Barclay |
| 7,011,962 B2 | 3/2006 | Barclay |
| 7,022,512 B2 | 4/2006 | Barclay |
| 7,033,584 B2 | 4/2006 | Barclay |
| 7,045,683 B2 | 5/2006 | Mukerji et al. |
| 7,063,855 B2 | 6/2006 | Hjaltason et al. |
| 7,067,145 B2 | 6/2006 | Place et al. |
| 7,067,285 B2 | 6/2006 | Mukerji et al. |
| 7,070,970 B2 | 7/2006 | Mukerji et al. |
| 7,087,432 B2 | 8/2006 | Qiu et al. |
| 7,172,886 B2 | 2/2007 | Keasling et al. |
| 7,183,089 B2 | 2/2007 | Keasling et al. |
| 7,192,751 B2 | 3/2007 | Keasling et al. |
| 7,214,853 B2 | 5/2007 | Facciotti et al. |
| 7,247,461 B2 | 7/2007 | Metz et al. |
| 7,259,006 B2 | 8/2007 | Komazawa et al. |
| 7,351,558 B2 | 4/2008 | Ruecker et al. |
| 7,374,908 B2 | 5/2008 | Yamaoka |
| 7,381,558 B2 | 6/2008 | Barclay |
| 7,419,596 B2 | 9/2008 | Dueppen et al. |
| 7,514,244 B2 | 4/2009 | Tanaka et al. |
| 7,642,083 B2 | 1/2010 | Frost et al. |
| 7,923,226 B2 | 4/2011 | Frost |
| 8,168,225 B2 | 5/2012 | Casaña Giner et al. |
| 2003/0060509 A1 | 3/2003 | Elswyk |
| 2003/0143659 A1 | 7/2003 | Bijl et al. |
| 2003/0180898 A1 | 9/2003 | Bailey et al. |
| 2004/0067574 A1 | 4/2004 | Bijl et al. |
| 2004/0209337 A1 | 10/2004 | Frost et al. |
| 2005/0181490 A1 | 8/2005 | Cheong et al. |
| 2005/0222312 A1 | 10/2005 | Frost et al. |
| 2006/0094089 A1 | 5/2006 | Barclay |
| 2006/0160203 A1 | 7/2006 | Barclay |
| 2006/0188969 A1 | 8/2006 | Barclay |
| 2006/0275904 A1 | 12/2006 | Ono et al. |
| 2008/0038800 A1 | 2/2008 | Ruecker et al. |
| 2008/0044875 A1 | 2/2008 | Ruecker et al. |
| 2008/0044876 A1 | 2/2008 | Ruecker et al. |
| 2008/0155888 A1 | 7/2008 | Vick et al. |
| 2008/0165786 A1 | 7/2008 | Ahuja et al. |
| 2008/0220515 A1 | 9/2008 | McCall |
| 2009/0029445 A1 | 1/2009 | Eckelberry et al. |
| 2009/0077863 A1 | 3/2009 | Oyler |
| 2009/0081748 A1 | 3/2009 | Oyler |
| 2010/0099901 A1 | 4/2010 | Hayashi et al. |

FOREIGN PATENT DOCUMENTS

| | | |
|---|---|---|
| EP | 568608 | 11/1993 |
| EP | 823475 | 2/1998 |
| EP | 894142 | 2/1999 |
| EP | 1305382 | 5/2003 |
| EP | 2110438 | 10/2009 |
| JP | 10072590 A2 | 3/1998 |
| JP | 11075884 | 3/1999 |
| JP | 2976027 | 11/1999 |
| JP | 2000060587 | 2/2000 |
| JP | 2003304894 | 10/2003 |
| JP | 2003319795 | 11/2003 |
| JP | 2004168985 | 6/2004 |
| JP | 2006304686 | 11/2006 |
| WF | 03033663 | 4/2003 |
| WO | WO 8703899 | 7/1987 |
| WO | WO 8900606 | 1/1989 |
| WO | WO 9107498 | 5/1991 |
| WO | WO 9114427 | 10/1991 |
| WO | WO 9212711 | 8/1992 |
| WO | WO 9213086 | 8/1992 |
| WO | 9408467 | 4/1994 |
| WO | 9633263 | 10/1996 |
| WO | 9704121 | 2/1997 |
| WO | 9737032 | 10/1997 |
| WO | 9743362 | 11/1997 |
| WO | WO 9111918 | 8/1999 |
| WO | 0005396 | 2/2000 |
| WO | 0054575 | 9/2000 |
| WO | 0154510 | 8/2001 |
| WO | 0210322 | 2/2002 |
| WO | 02092540 | 11/2002 |
| WO | 03086104 | 10/2003 |
| WO | 2004041251 | 5/2004 |
| WO | 2005058476 | 6/2005 |
| WO | 2007068997 | 6/2007 |

(56) References Cited

FOREIGN PATENT DOCUMENTS

| WO | 2007069078 | 6/2007 |
|---|---|---|
| WO | 2007074479 | 7/2007 |
| WO | 2008090989 | 7/2008 |
| WO | 2008129358 | 10/2008 |
| WO | 2009034124 | 3/2009 |

OTHER PUBLICATIONS

Japanese Application No. 2008-515327, Notice of Reasons for Rejection issued Feb. 24, 2015, 13 pages with English translation.
Canada Application No. 2611324, Office Action issued Feb. 11, 2015. 3 pages.
Mexico Application No. MX/a/2012/009979, office action issued Apr. 17, 2015, 5 pages.
Marine Biopharmacy, Marine Biopharmacy fermentation engineering, Beijing Chemical Industry Press, 2002, 1: 96-101, with translation (12 pages).
Napier et al., The production of long chain polyunsaturated fatty acids in transgenic plants, Genetic Engineering, vol. 26, 2004, 147-148.
Dongping et al., Chemical Insdustry Press, 2006: 37-38, with translation (49 pages).
Japan Application No. 2008-515327, Office Action mailed Sep. 1, 2015, 6 pages, with English translation.
European application No. 11170447.4, Communication pursuant to Article 94(3) EPC, issued Jan. 30, 2015, 4 pages.
Omega-3 News, Ocean Nutrition Canada Ltd., 2011.
Thraustochytriaceae Family Data Sheet, 2007, 2 pages.
Breakthrough Process to Extract Oil from Algae, http://www.miningtopnews.com/originoil-announces-breakthrough-process-to-extract-oil-from-.htm., Apr. 20, 2009.
Oilgae Glossary, Available at http://www.oilgae.com/algae/oil/extract/extract.html, Jun. 4, 2009, 8 pages.
*Thraustochytniidae* sp. MBIC11093 gene for 18S rRNA, partial sequence, strain: MBIC11093, Primary Accession No. AB183664, Online Database EMBL-EBI, Jul. 22, 2004.
*Thraustochytriidae* sp. MBIC11093 gene for 18S ribosomal RNA, partial sequence, Primary Accession No. AB073306, Online Database EMBL-EBI, Apr. 20, 2002.
*Thraustochytrium* sp. CHN-1 gene for 18S rRNA, partial sequence, Primary Accession No. AB126669, Online Database EMBL-EBI, Nov. 11, 2002.
*Thraustochytrium* sp. ONC-T18 18S ribosomal RNA gene, partial sequence, Primary Accession No. DQ3741149, Online Database EMBL-EBI, Oct. 20, 2006.
Thraustochytrium striatum small subunit ribosomal RNA gene, partial sequence, Primary Accession No. AF265338, Online Database EMBL-EBI, Jul. 8, 2001.
*Thrausiochyinun* sp. FJN-10 18S ribosomal RNA gene, partial sequence, Primary Accession No. AY773276, Online Database EMBL-EBI, Nov. 3, 2004.
U.S. Appl. No. 11/916,781, Non-Final Office Action mailed on Aug. 4, 2011. 15 pages.
U.S. Appl. No. 11/916,781, Notice of Allowance mailed on Dec. 15, 2011, 3 pages.
U.S. Appl. No. 11/916,781, Preliminary Amendment mailed on Jun. 23, 2008. 14 pages.
U.S. Appl. No. 11/916,781, Preliminary Amendment mailed on Feb. 25, 2010, 7 pages.
U.S. Appl. No. 11/916,781, Preliminary Amendment mailed on Dec. 6, 2007, 9 pages.
U.S. Appl. No. 11/916,781, Restriction Requirement mailed on May 17, 2011, 6 pages.
U.S. Appl. No. 11/916,781, Response to Office Action mailed on Oct. 10, 2011, 18 pages.
U.S. Appl. No. 11/916,781, Response to Restriction Requirement mailed on Jun. 15, 2011, 10 pages.
U.S. Appl. No. 12/309,895, Non-Final Office Action mailed on Oct. 15, 2012, 10 pages.
U.S. Appl. No. 12/309,895, Preliminary Amendment mailed on Jan. 25, 2010, 12 pages.
U.S. Appl. No. 12/309,895, Preliminary Amendment mailed on Mar. 8, 2010, 5 pages.
U.S. Appl. No. 12/309,895, Restriction Requirement mailed on May 10, 2012, 8 pages.
U.S. Appl. No. 12/309,895, Response to Restriction Requirement mailed on Aug. 7, 2012, 9 pages.
Aki et al., Thraustochytrid as a potential source of carotenoids, Journal of the American Oil Chemists' Society, vol. 80, Issue 8, 2003, pp. 789-794.
Armstrong et al., Carotenoids 2: Genetics and molecular biology of carotenoid pigment biosynthesis, Faseb Journal, vol. 10, issue 2, Feb. 1996, pp. 228-237.
Armstrong et al., Genetics Of Eubacterial Carotenoid Biosynthesis: A Colorful Tale, Annual Review of Microbiology, vol. 51, 1997, pp. 629-659.
Australian Application No. 2006325040, Amendments to Specification and Claims mailed on Sep. 30, 2009, 17 pages.
Australian Application No. 2006325040, Notice of Acceptance mailed on Apr. 4, 2012, 3 pages.
Australian Application No. 2006325040, Office Action mailed on Mar. 17, 2011, 3 pages.
Australian Application No. 2006325040, Office Action mailed on Sep. 26, 2011, 3 pages.
Australian Application No. 2006325040, Response to Office Action mailed on Mar. 16, 2012, 24 pages.
Australian Application No. 2006325040, Response to Office Action mailed on Aug. 19, 2011, 28 pages.
Australian Application No. 2007351658, Office Action mailed on May 14, 2012, 4 pages.
Bajpai et al., Optimization of production of docosahexaenoic acid (DHA) byThraustochytrium aureum ATCC 34304, Journal of the American Oil Chemists' Society, vol. 68, Issue 7, Jul. 1991, pp. 509-514.
Bajpai et al., Production of docosahexaenoic acid by Thraustochyinum aureum, Applied Microbiology and Biotechnology, vol. 35, Issue 6, Sep. 1991, pp. 706-710.
Baldwin, Application for the Approval of DHA-rich Oil, Omega Tech GmbH, Version No. Draft, 1997, 104 pages.
Barclay et al., Heterotrophic production of long chain omega-3 fatty acids utilizing algae and algae-like microorganisms, Journal of Applied Phycology, vol. 6, Issue 2, Apr. 1994, pp. 123-129.
Barclay et al., Nutritional Enhancement of n-3 and n-6 Fatty Acids in Rotifers and Artemia Nauplii by Feeding Spray-dried *Schizochytrium* sp., Journal of the World Aquaculture Society, vol. 27, Issue 3, Sep. 1995, pp. 314-322.
Basu et al., Nutritional and potential disease prevention properties of carotenoids, Journal of the American Oil Chemists' Society, vol. 78, Issue 7, 2001, pp. 665-675.
Bateman et al., Method for Extraction and Separation by Solid Phase Extraction of Neutral Lipid, Free Fatty Acids, and Polar Lipid from Mixed Microbial Cultures, Journal of Agricultural and Food Chemistry, Jan. 20, 1997, pp. 132-134.
Beckles et al., Omega-3 fatty acids (from fish oils) for cystic fibrosis, Cochrane Database Syst Rev., vol. 3, 2022, 12 pages.
Benson et al., GenBank, Nucleic Research, vol. 33, Jan. 2005, pp. D34-D38.
Bligh et al., A Rapid Method of Total Lipid Extraction and Purification, Canadian Journal of Biochemistry and Physiology, vol. 37, No. 8, 1959, pp. 911-917.
Bowles et al., Long-chain n-3 polyunsaturated fatty acid production by members of the marine protistan group the thraustochytrids: screening of isolates and optimisation of docosahexaenoic acid production. Journal of Biotechnology, vol. 70, Issues 1-3, Apr. 1999, pp. 193-202.
Burja et al., Evaluation of fatty acid extraction methods for *Thraustochyinum* sp. ONC-T18, J. Agric. Food Chem., vol. 55, issue 12, May 12, 2007, pp. 4795-4801.
Burja et al., Isolation and characterization of polyunsaturated fatty acid producing *Thraustochytrium* species: screen of strains and optimization of omega-3 production. Appl. Microbial Biotechnol., vol. 72, issue 6, Oct. 2006, pp. 1161-1169.

(56) References Cited

OTHER PUBLICATIONS

Canadian Application No. 2,611,324, Office Action mailed on Nov. 25, 2013, 3 pages.
Canadian Application No. 2,611,324, Office Action mailed on Apr. 30, 2012, 16 pages.
Canadian Application No. 2,611,324, Office Action mailed on Jun. 2, 2011, 5 pages.
Canadian Application No. 2,611,324, Office Action mailed on Nov. 2, 2011, 7 pages.
Canadian Application No. 2,611,324, Request for Examination and Preliminary mailed on Sep. 7, 2010, 9 pages.
Canadian Application No, 2,611,324, Voluntary Amendment mailed on Jan. 11, 2008, 4 pages.
Canadian Application No. 2,611,324, Office Action mailed on Oct. 29, 2010, 7 pages.
Canadian Application No. 2,611,324, Response to Office Action mailed on Apr. 29, 2011, 45 pages.
Canadian Application No. 2,611,324, Response to Office Action mailed on Sep. 2, 2011, 27 pages.
Canadian Application No. 2,659,603, Voluntary Amendment mailed on Jan. 30, 2009. 6 pages.
Carmona et al. Identification by HPLC-MS of carotenoids of the Thraustochytrium CHN-1 strain isolated from the Seto Inland Sea, Biosci Biotechnol Biochem., vol. 67, issue 4, 2003, pp. 884-888.
Caron et al., Defining DNA-Based Operational Taxonomic Units for Microbial-Eukaryote Ecology, Applied and Environmental Microbiology, vol. 75, issue 18, Sep. 2009, pp. 5797-5808.
Cartens et al., Eicosapentaenoic acid (20:5n-3) from the marine microalga *Phaeodactylum tricornutum*, Journal of the American Oil Chemists' Society, vol. 73, Issue 8, Aug. 1996, pp. 1025-1031.
Clarridge, Impact of 16S rRNA Gene Sequence Analysis for Identification of Bacteria on Clinical Microbiology and Infectious Diseases, Clinical Microbiol Rev., vol. 17, Issue 4, Oct. 2004, pp. 840-862.
Cleland et al., The Role of Fish Oils in the Treatment of Rheumatoid Arthritis, Drugs, vol. 63, Issue 9, May 2003, pp. 845-853.
Chinese Application No. 200680029630.5, Office Action mailed on Dec. 3, 2014, with English translation. 27 pages.
Chinese Application No. 200680029630.5, Office Action mailed on Mar. 14, 2014, 11 pages.
Chinese Application No. 200680029630.5, Office Action mailed on Dec. 9, 2011, 6 pages.
Chinese Application No. 200680029630.5, Office Action mailed on Sep. 6, 2010, 9 pages.
Chinese Application No. 200680029630.5, Rejection Decision mailed on Jul. 30, 2012, 9 pages.
Chinese Application No. 200680029630.5, Response to Office Action mailed on Apr. 10, 2012, 3 pages.
Chinese Application No. 200680029630.5, Response to Office Action mailed on Mar. 21, 2011, 9 pages.
Das et al., Beneficial effects(s) of n-3 fatty acids in cardiovascular disease: but, why and how?, Prostaglandins Leukot Essent Fatty Acids, vol. 63, Issue 6, Dec. 2000, pp. 351-362.
De Swaaf et al., Analysis of docosahexaenoic acid biosynthesis in Crypthecodinium cohnii by 13C labelling and desaturase inhibitor experiments, Journal of Biotechnology, vol. 103, Issue 1, Jun. 12, 2003, pp. 21-29.
Edge et al., The carotenoids as anti-oxidants—a review, J Photochem Photobiol B., vol. 41, Issue 3, Dec. 1997, pp. 189-200.
Ellenbogen et al. Polyunsaturated fatty acids of aquatic fungi: Possible phylogenetic significance, Comparative Biochemistry and Physiology, vol. 29, Issue 2, May 1969, pp. 805-811.
European Application No. 06848643.0, Amended Claim Set mailed on Mar. 3, 2008, 12 pages.
European Application No. 06848643.0, Communication Pursuant to 94(3) mailed on Jun. 8, 2009, 2 pages.
European Application No. 06848643.0, Consultation by Telephone mailed on Oct. 12, 2012, 4 pages.
European Application No. 06848643.0, Office Action mailed on Jan. 24, 2011, 4 pages.
European Application No. 06848643.0, Office Action mailed on Mar. 15, 2010, 4 pages.
European Application No. 06848643.0, Office Action mailed Oct. 23, 2012, 4 pages.
European Application No. 06848643.0, Pre-Exam Communication mailed on Jan. 12, 2008, 2 pages.
European Application No. 06848643.0, Request for Oral Proceedings mailed on May 16, 2012, 4 pages.
European Application No. 06848643.0, Written Submission for Oral Proceedings mailed on Sep. 7, 2012, 26 pages.
European Application No. 06848643.0, Written Submission for Oral Proceedings mailed on Oct. 1, 2012, 7 pages.
European Application No. 06848643.0, Response to Office Action mailed on Sep. 10, 2009, 9 pages.
European Application No. 06848643.0, Response to Office Action mailed on Mar. 25, 2011, 11 pages.
European Application No. 06848643.0, Response to Office Action mailed on Jun. 5, 2010, 15 pages.
European Application No. 07873362.3, Preliminary Amendment mailed on Apr. 18, 2011, 3 pages.
European Application No. 07873362.3, Supplementary European Search Report mailed on Sep. 3, 2012, 20 pages.
European Application No. 11170443.3, Examination Notification mailed on Apr. 23, 2013, 4 pages.
European Application No. 11170443.3, Supplementary European Search and Opinion mailed on May 31, 2012, 9 pages.
European Application No, 11170447.4, Examination Notification mailed on Nov. 4, 2013, 4 pages.
European Application No. 11170447.4, Preliminary Amendment mailed on Nov. 2, 2012, 17 pages.
European Application No. 11170447.4, European Search Report mailed on Apr. 4, 2012, 10 pages.
Felsenstein, Confidence Limits on Phytogenies: An Approach Using the Boostrap, Evolution, vol. 39, No 4, Jul. 1985, pp. 783-791.
Fleischhacker et al., New developments in the pharmacotherapy of schizophrenia, J. Neural Transm Suppl., vol. 64, 2003, pp. 105-117.
Franklin et al., Dietary marine algae (*Schizocytrium* sp.) increases concentration of conjugated linoleic, docosahexaenoic and transvaccenic acids in milk of dairy cows, The American Society for Nutritional Sciences, vol. 129, No. 11, Nov. 1, 1999, pp. 2048-2054.
Fu et al., Study on Production of EPA and DHA in Microbe Fermentation, Grain Processing, No. 1, 48-51, 2004, (12 pages with translation).
Gill, Celiruptor a highly efficient biomass processing & biofuels processing platform technology, Eco-Solids International, http://w3.gre.ac.uk/cost859/Biohaste/ESICellruptor.pdf, 2008.
Haag, Essential fatty acids and the brain, Can J Psychiatry., vol. 48, issue 3, 2003, pp. 195-203.
Hauvennale et al. Fatty acid production in *Schizochytrium* sp.: Involvement of a polyunsaturated fatty acid synthase and a type I fatty acid synthase, Lipids, vol. 41, issue 8, Aug. 2006, pp. 739-747.
Hong-Kong Application No. 08109347.3, Request to Record mailed on Aug. 20, 2008, 1 page.
Honda et al. Molecular phylogeny of labyrinthuiids and thraustochytrids based on the sequencing of 18S ribosomal RNA gene, Journal of Eukaryotic Microbiology, vol. 46, Issue 6, Nov. 1999, pp. 637-647.
Horrocks et al., Health Benefits of Docosahexaenoic Acid (DHA), Pharmacal Res., vol. 40, No. 3, 1999, pp. 211-255.
Huang et al. Grouping Newly Isolated Docosahexaenoic Acid-Producing Thraustochytrids Based on Their Polyunsaturated Fatty Acid Profiles and Comparative Analysis of 18S rRNA Genes, Marine Biotechnology, vol. 5, Issue 5, Oct. 2003, pp. 450-457.
Haung et al., Immunonutrients and neonates, Eur J Pediatr, vol. 162, issue 3, 2003, pp. 122-128.
Iida et al., Improvement of docosahexaenoic acid production in a culture of Thraustochytrium aureum by medium optimization, Journal of Fermentation and Bioengineering, vol. 81, Issue 1, 1996, pp. 76-78.
Indian Application No. IN9824/DELNP/2007, First Examiner Report mailed on May 22, 2013. 4 pages.
Japanese Application No. 2008-515327, Office Action mailed on Dec. 27, 2011, 3 pages.

(56) References Cited

OTHER PUBLICATIONS

Japanese Application No. 2008-515327, Office Action mailed on Aug. 14, 2012, 4 pages.
Japanese Application No. 2008-515327, Reexamination Prior to Trial mailed on Jun. 17, 2014, 5 pages.
Japanese Application No. 2008-515327, Request for Examination and Preliminary Amendment mailed on Jun. 8, 2009, 14 pages.
Japanese Application No. 2009-522370, Office Action mailed on Sep. 25, 2012, 8 pages.
Japanese Application No. 2009-522370, Response to Office Action mailed on Mar. 26, 2012, 3 pages.
Kaulmann et al., Biosynthesis of Polyunsaturated Fatty Acids by Polyketide Synthases Angewandte Chemie International Edition, vol. 41, Issue 11, Jun. 3, 2002, pp. 1866-1869.
Kazama et al., Mineral nutrition of *Pytium marinum*, a marine facultative parasite, Canadian Journal of Botany, vol. 51, issue 4, 1973, pp. 693-699.
Khozin et al., Differential response of microalgae to the substituted pyridazinone, sandoz 9785, reveal different pathways in the biosynthesis of eicosapentaenoic acid, Phystochemisty, vol. 42, Issue 4, Jul. 1996, pp. 1025-1029.
Kowalchuk et al., Detection and characterization of fungal infections of *Ammophila arenaria* (marram grass) roots by denaturing gradient gel electrophoresis of specifically amplified 18s rDna, Appl Environ Microbiol., vol. 63, issue 10, Oct. 1997, pp. 3858-3865.
Kumar et al., Radioprotection by antioxidant enzymes and enzyme mimetics, Pharmacol Ther., vol. 39, issue 1-3, 1988, pp. 301-309.
Leander et al., The Labyrinthulomycota Is Comprised of Three Distinct Lineages, Mycologia, vol. 39, No. 3, Botany, University of Georgia, Miller Plant Sciences, May-Jun. 2001, pp. 459-464.
Lewis et al., Evaluation of extraction methods for recovery of fatty acids from lipid-producing microheterotrophs, Journal of Microbiological Methods, vol. 43, Issue 2, Dec. 15, 200, pp. 107-116.
Li et al., Production of docosahexaenoic acid by Thraustochytrium roseum, Journal of Industrial Microbiology, vol. 13, issue 4, Aug. 1994, pp. 238-241.
Liu et al., Study on Production of EPA and DHA by Microbe Fermentation, Food Science and Technology, No. 6, 13-16, 2004, (12 pages with translation).
Machlin et al., Free radical tissue damage: protective role of antioxidant nutrients, FASEB J., vol. 1, issue 6, Dec. 1987, pp. 441-445.
Mares-Perlman et al., The body of evidence to support a protective role for lutein and zeaxanthin in delaying chronic disease. Overview, The Journal of Nutrition, vol. 132, No. 3, Mar. 1, 2002, pp. 518S-524S.
Metz et al., Production of polyunsaturated fatty acids by polyketide synthases in both prokaryotes and eukaryotes, Science, vol. 293, issue 5528, Jul. 2001, pp. 290-293.
Mo et al., Development of a PCR strategy for thraustochytrid identification based on 18S rDNA sequence, Marine Biology, vol. 140, Issue 5, May 2002, pp. 883-889.
Molina Grima et al., Recovery of microalgal biomass and metabolites: process options and economics, Biotechnology Advances, vol. 20, Issues 7-8, Jan. 2003, pp. 491-515.
Morita et al., Enhancement of polyunsaturated fatty acid production by cerulenin treatment in polyunsaturated fatty acid-producing bacteria, Biotechnol Lett.: vol. 27, issue 6, Mar. 2005, pp. 389-393.
Mexican Application No. MX/A/2007/015519, Notice of Allowance mailed on Jun. 19, 2012, 1 page.
Mexican Application No. MX/A/2007/015519, Office Action mailed on Jan. 31, 2012, 11 pages.
Mexican Application No. MX/A/2007/015519, Office Action mailed on Mar. 11, 2011, 3 pages.
Mexican Application No. MX/A/2007/015519, Office Action mailed on May 8, 2012, 5 pages.
Mexican Application No. MX/A/2007/015519, Office Action mailed on Jun. 3, 2011, 6 pages.
Mexican Application No. MX/A/2007/015519, Response to Office Action mailed on Jun. 11, 2012, 8 pages.
Mexican Application No. MX/A/2007/015519, Response to Office Action mailed on Apr. 13, 2012, 11 pages.
Mexican Application No. MX/A/2007/015519, Response to Office Action mailed on Aug. 29, 2011, 17 pages.
Mexican Application No. MX/A/2007/015519, Response to Office Action mailed on May 24, 2011, 12 pages.
Mexican Application No. MX/A/2012/009979, Office Action mailed on Aug. 22, 2014, with translation. 4 pages.
Nakahara et al., Production of docosahexaenoic and docosapentaenoic acids by *Schizochytnum* sp. isolated from Yap Islands, Journal of the American Oil Chemists' Society, vol. 73, Issue 11, Nov. 1996,, pp. 1421-1426.
Nakano et al., Inhibitory effects of capsaicinoids on fatty acid desaturation in a rat liver cell line, Biosci Biotechnol Biochem. vol. 65, issue 8, Aug. 2001, pp. 1859-1863.
International Application No. PCT/IB2006/003977, International Preliminary Report on Patentability and Written Opinion mailed on Dec. 11, 2007, 8 pages.
International Application No. PCT/IB2006/003977, International Search Report mailed on Sep. 24, 2007, 7 pages.
International Application No. PCT/IB2007/004596, International Search Report and Written Opinion mailed on Jan. 14, 2009, 14 pages.
International Application No. PCT/IB2007/004596, International Preliminary Report on Patentability mailed on Jan. 18, 2011, 10 pages.
Pignatiello et al., An Overview of the Strategy and Tactics of Taguchi, IIE Transactions, vol. 20, Issue 3, 1988, pp. 247-254.
Pinkart et al., Rapid separation of microbial lipids using solid phase extraction columns. Journal of Microbiological Methods, vol. 34, Issue 1, Sep. 1, 1998, pp. 9-15.
Ratledge et al., Single cell oils—A coming of age, Lipid Technology, vol. 16, 2004, pp. 34-39.
Saitou et al., The Neighbor-joining Method: A New Method for Reconstructing Phylogenetic Tress, Mol. Biol. Evol., vol. 4, 1987, pp. 406-425.
Schagerl et al., Acclimation of chlorophyll a and carotenoid levels to different irradiances in four freshwater cyanobacteria. J Plant Physiol., vol. 163, issue 7, May 2006, pp. 709-716.
Schill, OriginOil achieves rapid algae oil extraction. Biomass Magazine, retrieved from the Internet: < URL:www.biomassmagazine.com/article.jsp?article id=2700>, 2009.
Shapiro, Could n-3 olyunsaturated fatty acids reduce pathological pain by direct actions on the nervous system?, Prostaglandins Leukot Essent Fatty Acids., vol. 68, issue 3, Mar. 2003, pp. 219-224.
Shimizu et al., Inhibitory effects of curcumin on fatty acid desaturation inMortierella aplina 1S-4 and rat liver microsomes. Lipids, vol. 27, Issue 7, Jul. 1992, pp. 509-512.
Shirasaka et al., Effects of Cyanocobalamin and p-toluic acid on the Fatty Acid Composition of Schizochytrium limacinum (Thraustochytriaceae, Labyrinthulomycota), Mycoscience, vol. 46, Dec. 2005, pp. 356-363.
Sijtsma et al., Recent advances in fatty acid synthesis in oleaginous yeasts and microalgae, ecent Research Developments in Microbiology, vol. 2, Jan. 1998, pp. 219-232.
Singh et al., Cancer chemoprevention. Part 1: Retinoids and carotenoids and other classic antioxidants. Oncology (Williston Park). vol. 12, issue 11, 1996, pp. 1643-1653.
Singh et al., Docosahexaenoic acid (DHA) production by *Thraustochytrium* sp. ATCC 20892, World Journal Microbiology and Biotechnology, vol. 12, Issue 1, Jan. 1996, pp. 76-81.
Skerett et al., Consumption of fish and fish oils and decreased risk of stroke, Prev. Cardiol., vol. 6, issue 1, 2003, pp. 38-41.
Smith, Carotenoids and cancer prevention and potential therapy, Br J Biomed Sci., vol. 55, issue 4, Dec. 1998, pp. 268-275.
Song et al., Effective Phase Separation of Biomass Pyrolysis Oils by Adding Aqueous Salt Solutions, Energy Fuels, vol. 23, Apr. 29, 2009, pp. 3307-3312.
Spector et al., Diet and asthma: has the role of dietary lipids been overlooked in the management of asthma?, Ann Allergy Asthma Immunol., vol. 90, issue 4, Apr. 2003, pp. 371-377.

(56) References Cited

OTHER PUBLICATIONS

Tao et al., Engineering a β-carotene ketolase for astaxanthin production, Metabloic Engineering, vol. 8, Issue 6, Nov. 2006, pp. 523-531.
Terry et al., Intakes of fish and marine fatty acids and the risk of cancers of the breast and prostate and of the other hormone-related cancers: a review of the epidemiologic evidence, Am J Clin Nutr., vol. 77. issue 3, 2003, pp. 532-543.
Tian et al., Progress in understanding the origin and functions of carotenoid hyroxylases in plants, Archives of Biochemistry and Biophysics, vol. 430, Issue 1, Oct. 1, 2004, pp. 22-29.
Valadon. Carotenoids as additional taxonomic characters in fungi: A review Transactions of the British Mycological Society, vol. 67, Issue 1, 1976, pp. 1-15.
Wardencki et al., Trends in solventless sample preparation techniques for environmental analysis, Journal of Biochemical and Biophysical Methods, vol. 70, Issue 2, Mar. 10, 2007, pp. 275-288.
Yamaoka et al., Growth and carotenoid production of *Thraustochytrium* sp. CHN-1 cultured under superbright red and blue light-emitting diodes, Bioscience, Biotechnology, and Biochemistry, vol. 68, issue 7, 2004, pp. 1594-1597.
Yamaoka et al., Growth Characterization and Resources of Thraustochytrium CHN-1 Isolated from the Seto Inland Sea, Bulletin of the Society of Sea Water Science, Japan. vol. 59, No. 1, 2005, pp. 23-31.
Yokochi et al., Optimization of docosahexaenoic acid productions by Schizocytrium limacinum SR21, Applied Microbiology and Biotechnology, vol. 49, Issue 1, Jan. 1996, pp. 72-76.
Yokoyama et al., Taxonomic rearrangement of the genus *Schizochytrium sensu lato* based on morphology, chemotaxonomic charateristics, and 18S rRNA phylogeny (Thraustochytriaceae, Labyrinthulomycetes): emendation for Schizochytrium and erection of Aurantiochytrium and. <Oblongichytrium gen. nov.> Mycoscience, vol. 48, Issue 4, Aug. 2007, pp. 199-211.
South African Application No. 2000/01192, Acceptance of Amendment mailed on Mar. 27, 2012, 1 page.
South African Application No. 2000/01192, Preliminary Amendment mailed on Mar. 27, 2012, 13 pages.
South African Application No. 2008/00079, Acceptance of Amendment mailed on Mar. 26, 2009, 1 page.
South African Application No. 2008/00079, Application to Amend a Complete Specification mailed on Mar. 24, 2009, 22 pages.
South African Application No. 2008/00079, Certificate of Patent mailed on Mar. 25, 2009, 3 pages.
Zhekisheva et al., Inhibition Of Astaxanthin Synthesis Under High Irradiance Does Not Abolish Triacylglycerol Accumulation in the Green Alga *Haematococcus pluvialis* (Chlorophyceae), Journal of Phycology, vol. 41, Issue 4, Aug. 2005, pp. 819-826.
Japanese Application No. P2013-221471, Notice of Reasons For Rejection issued Feb. 16, 2015, 10 pages with English translation.
European Application No. 11170443.3, Office Action, Jan. 5, 2016, 4 pages.
Canadian Patent Application No. 2,611,324 Office Action mailed Apr. 1, 2016, 3 pages.
Chinese Patent Application No. 201510035502.1, Office Action mailed Mar. 3, 2017, English Translation, 4 pages.

FIGURE 5

Microbial Sources of PUFAs

| Micro-organism | PUFA cell content (mg g$^{-1}$) | PUFA Productivity (mg L$^{-1}$ d$^{-1}$) |
|---|---|---|
| *Phaeodactylum tricornutum* (diatom) | 18.7 (EPA) | 47.8 |
| *Monodus sp.* (microalga) | 34.4 (EPA) | 25.7 |
| *Mortierella alpina 1S-4* (fungi) | 67.0 (ARA) | 118.0 |
| *Shewanella sp. SCRC-2738* (bacterium) | 10.4 (EPA) | 64.5 |
| Thraustochytrids (protists) | 100+ (DHA) | 1000+ |

PUFA metabolic pathways

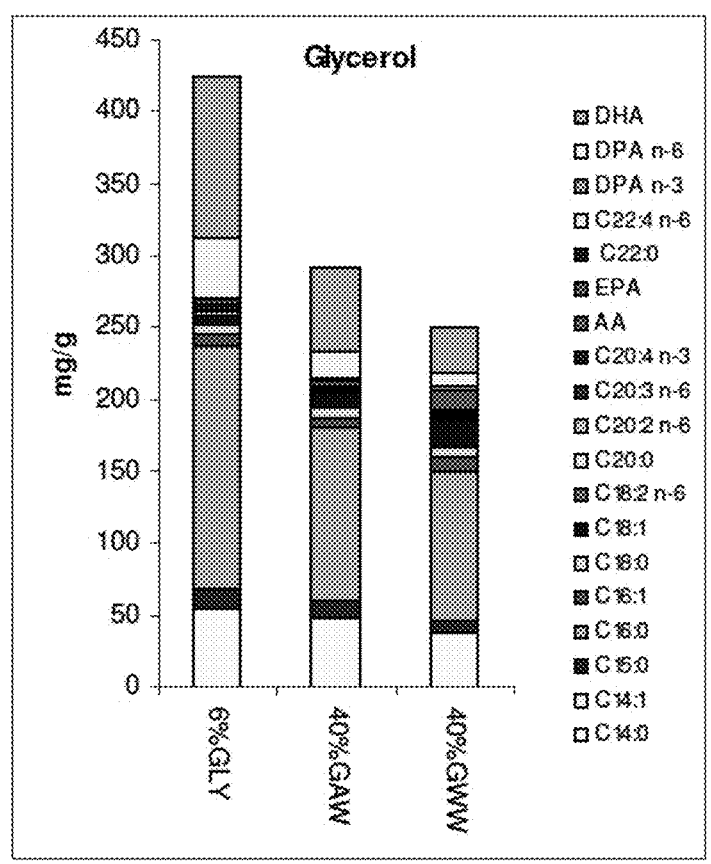

| Name | Retention Time (min) | Amount (µg/ml) | Carotenoid (µg/g) |
|---|---|---|---|
| Astaxanthin | 8.2 | 0.38 | 1.53 |
| Zeaxanthin | 11.2 | 0.11 | 0.42 |
| Canthaxanthin | 15.2 | 1.03 | 4.11 |
| Echinenone | 24.6 | 0.37 | 1.46 |
| β-Carotene | 30.3 | 5.07 | 20.23 |

SEQUENCE LISTING

```
<160> NUMBER OF SEQ ID NOS: 3

<210> SEQ ID NO 1
<211> LENGTH: 1724
<212> TYPE: DNA
<213> ORGANISM: Artificial Sequence
<220> FEATURE:
<223> OTHER INFORMATION: Description of Artificial Sequences; note =
      synthetic construct

<400> SEQUENCE: 1
dgtagtcata cgctcgtctc aaagattaag ccatgcatgt gtaagtataa gcgattatac      60
tgtgagactg cgaacggctc attatatcag ttatgatttc ttcggtattt tctttatatg     120
gatacctgca gtaattctgg aattaataca tgctgagagg gcccgactgt tcgggagggc     180
cgcacttatt agagttgaag ccaagtaaga tggtgagtca tgataattga gcagatcgct     240
tgtttggagc gatgaatcgt ttgagtttct gccccatcag ttgtcgacgg tagtgtattg     300
gactacggtg actataacgg gtgacgggga gttagggctc gactccggag agggagcctg     360
agagacggct accacatcca aggaaggcag caggcgcgta aattacccaa tgtggactcc     420
acgaggtagt gacgagaaat atcaatgcgg ggcgcttcgc gtcttgctat tggaatgaga     480
gcaatgtaaa accctcatcg aggatcaact ggagggcaag tctggtgcca gcagccgcgg     540
taattccagc tccagaagcg tatgctaaag ttgttgcagt taaaaagctc gtagttgaat     600
ttctggggcg ggagccccgg tctttgcgcg actgcgctct gtttgccgag cggctcctct     660
gccatcctcg cctctttttt tagtggcgtc gttcactgta attaaagcag agtgttccaa     720
gcaggtcgta tgacctggat gtttattatg ggatgatcag ataggggctcg ggtgctattt     780 tgttggtttg cacatctgag taatgatgaa taggaacagt tggggggtatt cgtatttagg     840 agctagaggt gaaattcttg gatttccgaa agacgaacta cagcgaaggc atttaccaag     900
catgttttca ttaatcaaga acgaaagtct ggggatcgaa gatgattaga taccatcgta     960
gtctagaccg taaacgatgc cgacttgcga ttgcggggtg tttgtattgg accctcgcag    1020
cagcacatga gaaatcaaag tctttgggtt ccggggggag tatggtcgca aggctgaaac    1080
ttaaaggaat tgacggaagg gcaccaccag gagtggagcc tgcggcttaa tttgactcaa    1140
cacgggaaaa cttaccaggt ccagacatag gtaggattga cagattgaga gctctttctt    1200
gattctatgg gtggtggtgc atggccgttc ttagttggtg gagtgatttg tctggttaat    1260
tccgttaacg aacgagacct cggcctacta aatagcggtg ggtatggcga catacttgcg    1320
tacgcttctt agagggacat gttcggtata cgagcaggaa gttcgaggca ataacaggtc    1380
tgtgatgccc ttagatgttc tgggccgcac gcgcgctaca ctgatgggtt caacgggtgg    1440
tcatcgttgt tcgcagcgag gtgctttgcc ggaaggcatg gcaaatcctt tcaacgccca    1500
tcgtgctggg gctagatttt tgcaattatt aatctccaac gaggaattcc tagtaaacgc    1560
aagtcatcag cttgcattga atacgtccct gcccttgta cacaccgccc gtcgcaccta    1620
```

```
ccgattgaac ggtccgatga aaccatggga tgaccttttg agcgtttgtt cgcgaggggg    1680
gtcagaactc gggtgaatct tattgtttag aggaaggtga agtc                    1724
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequences; note = synthetic construct

<400> SEQUENCE: 2

```
dcaacctggt tgatcctgcc agta                                          24
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequences; note = synthetic construct

<400> SEQUENCE: 3

```
dtcactacgg aaaccttgtt acgac                                         25
```

EUKARYOTIC MICROORGANISMS FOR PRODUCING LIPIDS AND ANTIOXIDANTS

This application is a continuation application of U.S. patent application Ser. No. 13/427,562, filed Mar. 22, 2012, now U.S. Pat. No. 8,921,069, which is a continuation application of, and claims benefit of U.S. patent application Ser. No. 11/916,781, filed Jun. 23, 2008, now U.S. Pat. No. 8,163,515, which is a national phase application of, and claims benefit of PCT/IB2006/003977, filed Jun. 7, 2006, which claims benefit of and priority to U.S. Provisional Patent Application No. 60/688,207, filed Jun. 7, 2005, and U.S. Provisional Application No. 60/751,401, filed Dec. 16, 2005, all of which are incorporated by reference herein their entirety.

I. BACKGROUND

There is overwhelming scientific evidence that (n-3) highly unsaturated fatty acids such as docosahexaenoic acid (DHA) have a positive effect on cardio-circulatory diseases, chronic inflammations and brain disorders. The (n-6) fatty acids on the other hand have been noted as intermediate metabolites within the eicosanoid steroids, such as prostaglandins, leucotrienes or the like.

Currently, the main source of these highly unsaturated fatty acids is fish, with DHA and eicosapentaenoic acid (EPA) noted within various blue fish (such as sardines and tuna) at amounts around 20% and 10%, respectively. Yet, if one intends to use fish oil as the sole source of these lipids, several disadvantages exist, such as problems with flavor taint, uncontrollable fluctuations in availability, natural fish oil content variability, as well as the potential to accumulate harmful environmental pollutants. In addition, if one intends to obtain a highly purified (n-3) or (n-6) oil from these sources, it is very difficult to preferentially separate and purify.

II. SUMMARY

Disclosed are compositions and methods related to a eukaryote of the order Thraustochytriales and family Thraustochytriaceae which when cultured produce quantities of unsaturated fatty acids, such as omega 3 (n-3) and/or omega 6 (n-6) oils, such as DHA, EPA and DPA, capable of being purified and used as all such compositions are used and more, because of their means of production

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a chart showing the results obtained from fatty acid methylation of the lipids derived from ONC-T18.

FIG. 2 graphically depicts a fatty acid methyl ester comparison between the original ONC-T18 isolate collected at Advocate Harbor and that of the ONC-T18 *Thraustochytrium* sp. deposited with ATCC as PTA-6245. All peaks were identified by Gas Chromatography and Mass Spectrometry.

FIG. 5 shows a chart of oil producing organisms isolated as described elsewhere herein.

FIG. 10 shows a comparison of fatty acid production maxima and compositions under various alternative, low-cost carbon sources.

FIGS. 11A, 11B, 11C, and 11D, show a grouping of isolates collected based on their C20 and C22 PUFA profiles. Results were compared to two reference strains: ATCC 20891 and MYA-1381.

Figure 12:
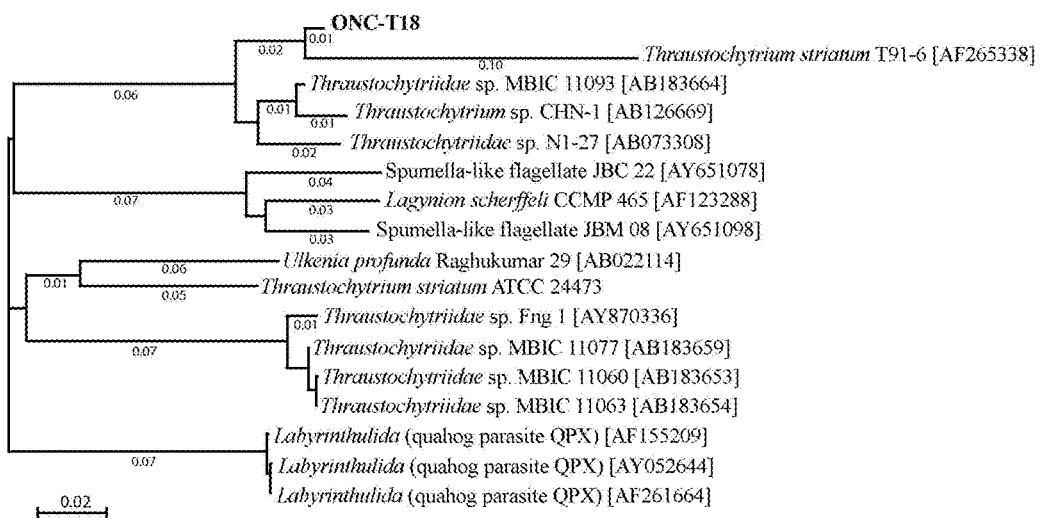

FIG. 12 shows a 18S rRNA Neighbour joining tree of strain ONC-T18. The bar represents genetic distance, while square brackets depict GenBank derived sequences used within this phylogenetic tree.

Figure 13:
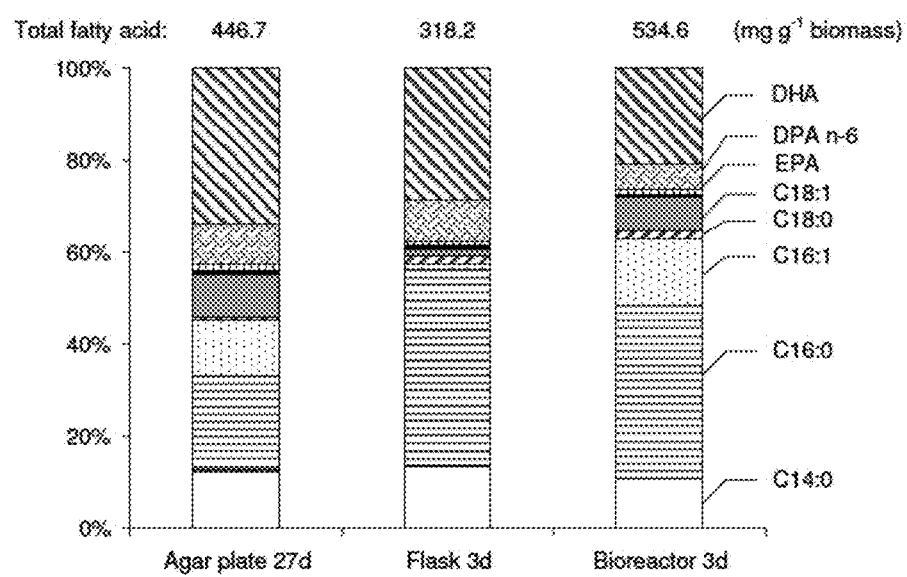

FIG. 13 shows the fatty acid profile of ONC-T18 grown in medium containing 2 g $L^{-1}$ yeast extract, 8 g $L^{-1}$ L-glutamate, 6 g $L^{-1}$ sea salt and 60 g $L^{-1}$ glucose in 3 different types of fermentation: agar plate (1.5% agar, 25° C., 27 days), flasks (50 ml in 250 ml flask, 120 RPM, 25° C., 3 days) and 5 L bioreactor (4 lpm air, $pO_2$ 90%, 25° C., 3 days).

Figure 14:
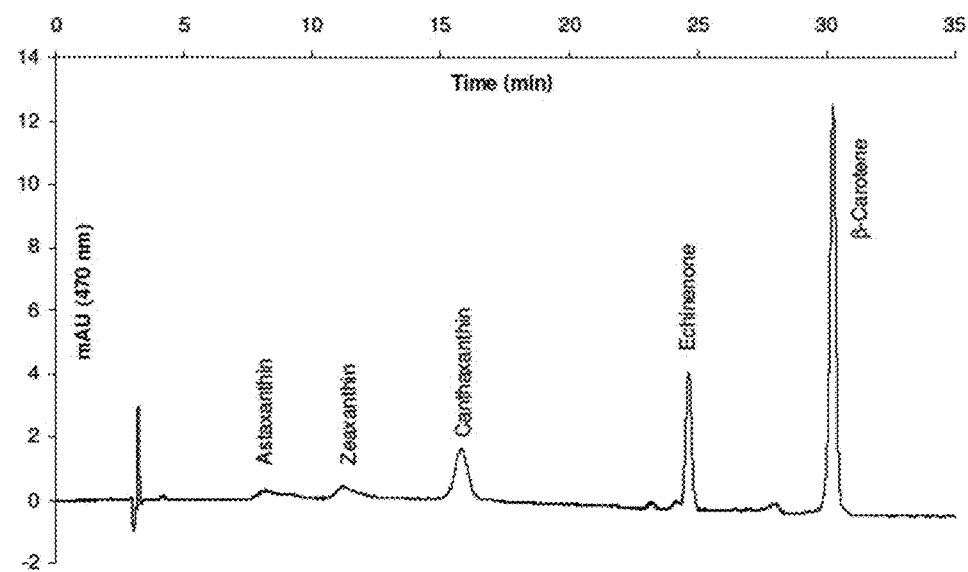

FIG. 14 shows the HPLC chromatogram of carotenoid compounds isolated from *Thraustochytrium* sp. ONC-T18. For example, Astaxanthin, Zeaxanthin, Canthaxanthin, Echinenone, and β-Carotene were isolated from *Thraustochytrium* sp. ONC-T18.

Figure 15:
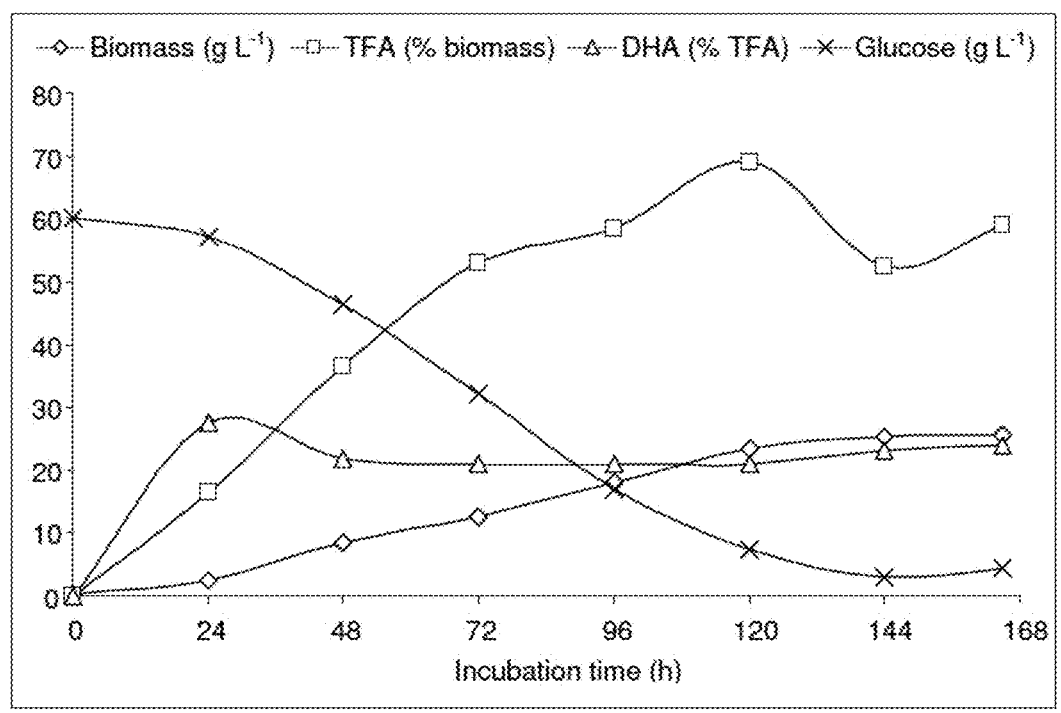

FIG. 15 shows typical biomass, total fatty acid (TFA), DHA production and glucose utilization of *Thraustochytrium* sp. ONC-T18 maintained in a 5 L bioreactor for 168 h with medium composed of 60 g $L^{-1}$ glucose, 2 g $L^{-1}$ yeast extract, 8 g $L^{-1}$ glutamic acid and 6 g $L^{-1}$ salt (4 lpm air, $pO_2$ 90%, 25° C., pH 7-9).

Figure 16:
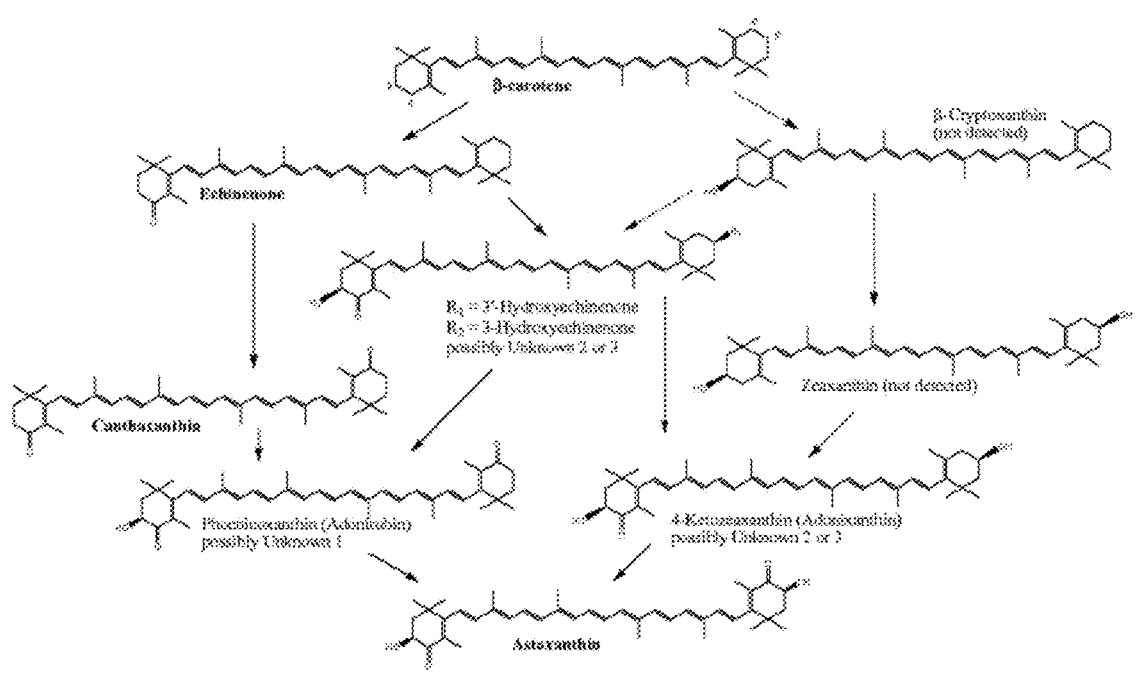

FIG. 16 shows postulated pathways involved in the formation of astaxanthin in *Thraustochytrium* sp. ONC-T18.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Those skilled in the art will recognize, or be able to ascertain using no more than routine experimentation, many equivalents to the specific embodiments of the method and compositions described herein. Such equivalents are intended to be encompassed by the claims below.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control. It is understood that unless specifically indicated otherwise, a compound or composition or condition can be reduced relative to another compound or composition or condition.

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control. It is understood that unless specifically indicated otherwise, a compound or composition or condition can be inhibited relative to another compound or composition or condition.

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

The term "therapeutically effective" means that the amount of the composition used is of sufficient quantity to ameliorate one or more causes or symptoms of a disease or disorder. Such amelioration only requires a reduction or alteration, not necessarily elimination.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

Throughout the description and claims of this specification, the word "comprise" and variations of the word, such as "comprising" and "comprises," means "including but not limited to," and is not intended to exclude, for example, other additives, components, integers or steps.

The term "cell" as used herein also refers to individual microbial cells, or cultures derived from such cells. A "culture" refers to a composition comprising isolated cells of the same or a different type.

The term "metabolite" refers to active derivatives produced upon introduction of a compound into a biological milieu, such as a patient.

When used with respect to pharmaceutical and nutraceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2° C. to 8° C.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Isolating" and any form such as "isolate" refer to a situation where something is in a form wherein it can be manipulated or further purified. Isolated and its forms indicates that something is in a current state which is different than a previous state. For example, a ribosomal RNA molecule can be "isolated" if it is, for example removed from an organism, synthesized or recombinantly produced. Often, the "isolation" of one thing is in relation to something else. For example, a eukaryote as discussed herein can be isolated as discussed herein, by, for example, culturing the eukaryote, such that the eukaryote survives in the absence of appreciable amounts (detectable) of other organisms. It is understood that unless specifically indicated otherwise, any of the disclosed compositions can be isolated as disclosed herein.

"Purify" and any form such as "purifying" refers to the state in which a substance or compound or composition is in a state of greater homogeneity than it was before. It is understood that as disclosed herein, something can be, unless otherwise indicated, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure. For example, if given composition A was 90% pure, this would mean that 90% of the composition was A, and that 10% of the composition was one or more things, such as molecules, compounds, or other substances. For example, if a disclosed eukaryotic microorganism, for example, produces 35% DHA, this could be further "purified" such that the final lipid composition was greater than 90% DHA. Unless otherwise indicated, purity will be determined by the relative "weights" of the components within the composition. It is understood that unless specifically indicated otherwise, any of the disclosed compositions can be purified as disclosed herein.

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular species of the family Thraustochytriaceae is disclosed and discussed and a number of modifications that can be made to a number of organisms including species of the family Thraustochytriaceae are discussed, specifically contemplated is each and every combination and 10 permutation of these species from the family Thraustochytriaceae and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. COMPOSITIONS

Disclosed are eukaryotic microorganisms of the order Thraustochytriales, preferably *Thraustochytrium* or *Schizochytrium* species, having the ability to produce lipids, such as fatty acids, such as unsaturated fatty acids, such as omega-3 fatty acids, such as omega-6 fatty acids, and omega-9 fatty acids, such as the (n-3) series of docosahexaenoic acid (DHA) and eicosapentaenoic acid (EPA), (n-6) series of docosapentaenoic acid (DPA) and the (n-9) series of palmitic and stearic acids. The disclosed eukaryotic microorganisms can also produce antioxidants, such as but not limited to the carotenoid compound carotene, (for example β-carotene) and the xanthophylls compounds astaxanthin, zeaxanthin, canthaxanin, and echinenone.

Also disclosed are conditions for the isolation and growth of the eukaryotic microorganisms. For example, herewith are heterotrophic growth conditions for production of the disclosed lipids and antioxidants, for example, both individually and cumulatively. Accordingly, it is possible through the use of this unique eukaryote, to effectively produce the (n-3) series of DHA and/or the (n-6) series of DPA and/or the carotenoid series of antioxidant compounds and/or the xanthophylls series of antioxidant compounds, which are useful as or within nutraceuticals, food additives, pharmaceuticals or industry.

Disclosed are compositions comprising a eukaryotic microorganism comprising or consisting of a *Thraustochytrium* species, an example as disclosed herein being the ONC-T18 strain which has a deposit number of ATCC accession number PTA-6245.

It is understood that the eukaryotic microorganism and any clones, modified organisms or genes isolated from said organism as set forth in ONC-T18 are also disclosed. The disclosed organisms have the ability to produce unsaturated fatty acids, such as lipids containing the omega-3 series of DHA and EPA, and the omega-6 series of DPA and various antioxidant such as carotenoids, xanthophylls and phenolics.

Also disclosed are processes for the production of biomass containing said compounds. Further disclosed are processes for preparing omega-3, omega-6 and carotenoid compounds utilizing the eukaryotic microorganism. Also disclosed are processes for the production of microbial derived (or single celled) oils.

In addition, disclosed are the fatty acids and carotenoids produced by the disclosed eukaryotic microorganism and any progeny (genetically modified or otherwise), various feedstuffs, nutraceuticals, pharmaceutical and food supplemented with the lipids and antioxidants, as well as a process for utilizing these compounds as an additive for various feedstuffs and foods.

U.S. Pat. No. 5,130,242 to Barclay disclosed a collection and screening process to isolate strains of microorganisms with the following characteristics for the production of omega-3 fatty acids: 1) capable of heterotrophic growth; 2) produce a high content of omega-3 fatty acids; 3) unicellular; 4) produce a low content of standard and omega-6 fatty acids; 5) non-pigmented, white or colorless cells; 6) thermotolerant (e.g., ability to grow above 30° C.); and 7) eurhaline (e.g., ability to grow at a wide range of salinities, but preferably at low salinity).

The '242 disclosure also describes a process for the heterotrophic production of whole-celled or extracted microbial products with a high concentration of omega-3 fatty acids, which can later be used in animal or human food products. This process uses microorganisms identified by the collection and screening process disclosed thereof. These microorganism, which are of the order Thaustochytriales, are cultured in ground grain. To enhance production of omega-3 fatty acids, low temperature stressing and high dissolved oxygen are used, as well as the addition of antioxidants, growth factors, vitamins, and phosphorous. The extracted products contain high concentrations of omega-3 fatty acids (e.g., C20:5w3, C22:5w3; and C22:6w3) and low concentrations of omega-6 fatty acids (e.g., C20:4w6 and C22:5w6). Specifically, the ratios of the C20:5w3 to C22:6w3 fatty acids run from 1:1 to 1:30. Ratios of C22:5w3 to C22:6w3 fatty acids run from 1:12 to only trace amounts of C22:5w3. Also, the microorganisms produce from 0.6 to 0.72% DHA, 0 to 5% DPA, and 0 to 18.9% EPA, by weight of total fatty acid.

U.S. Pat. No. 6,451,567 to Barclay disclosed a process for growing *Thraustochytrium* and *Schizochytrium* in a non-chloride medium (<3 g/L) containing sodium salts (e.g., sodium sulfate). The non-chloride medium results in cell aggregate sizes of less than 150 µm. The disclosed process produces microorganisms and extracts that are useful in food products for aquaculture. Further components of the food products include flaxseed, rapeseed, soybean, and avocado meal. The microorganisms can produce 1.08 g/L of medium per day of omega-3 fatty acids. The '567 disclosure further describes various culture mediums, which include sea water, glucose (1, 3, 5, or 10 g/L), yeast extract (0.01, 0.2, 0.4 and 5 g/L), additional nitrogen sources such as protein hydrosylate (1 g/L), liver extract (1 g/L), glutamate (5 g/L), MSG (3 g/L), and additional salts, trace vitamins and minerals (e.g., $KH_2PO_4$, $MgSO_4$, and gelatin extract).

U.S. Pat. No. 6,582,941 to Yokochi et al. discloses a *Schizochytrium* species, strain SR21 and another *Schizochytrium* strain belonging to the same species that have the ability to produce fatty acid fractions having a high concentration of omega-3 DHA and/or omega-6 DPA and a low concentration of EPA. Also, disclosed are methods of culturing such microorganisms and isolating such fatty acids. The medium used contains sea salt, yeast extract (0.2, 1.0, or 10 g/L), corn steep liquor (0.5, 1.0, or 10 g/L), glucose (10-120 g/L), plus additional salts (e.g., $NH_4OAc$, phosphates). The fatty acid compositions contain about 15 to 20% DHA by weight of biomass (about 28% by weight of total fatty acid). The compositions can be used in food products (e.g., baby milk).

U.S. Pat. No. 6,607,900 to Bailey et al. disclosed a process for growing eukaryotic microorganisms (e.g., *Schizochytrium* sp. ATCC No. 20888) that are capable of producing at least 20% of their biomass as polyunsaturated lipids (particularly omega-3 and -6 fatty acids). The process involves culturing the microorganisms in a medium containing a carbon and nitrogen source. Also disclosed is the use of low dissolved oxygen levels (less than 3%) and low chloride ion levels (less than 3 g/L) to enhance production. The microorganisms have a lipid production rate of at least 0.5 g/L/h. The lipid fraction is from 15 to 20% DHA by weight of biomass (about 35% by weight of total fatty acid methyl ester).

U.S. Publication No. 2004/0161831 to Komazawa et al discloses a *Thraustochytrium* strain (LEFT; ATCC No. FERM BP-08568) that has the ability to produce DHA. By culturing in conventional media, the microorganism can produce oil with at least 50% by weight DHA. The oil can be treated with a lipase prior to isolation of DHA. The oil can be used in food or drinks or the DHA can be hydrolyzed to produce behenic acid.

1. Fatty Acids

Fatty acids are hydrocarbon chains that terminate in a carboxyl group, being termed unsaturated if they contain at least one carbon-carbon double bond, and polyunsaturated when they contain multiple such bonds. Long-chain polyunsaturated fatty acids (PUFA) or highly-unsaturated fatty acids (HUFA), may be divided into the (n-3) and (n-6) series as a result of the location of these double bonds. There is overwhelming scientific evidence that (n-3) highly unsaturated fatty acids such as DHA have a positive effect on cardio-circulatory diseases, chronic inflammation and brain disorders. The (n-6) fatty acids on the other hand have been noted as intermediate metabolites within the eicosanoid steroids, such as prostaglandins, leucotrienes or the like.

Polyunsaturated fatty acids can comprise 1, 2, 3, 4, 5, 6, 7, 8, 9, or 10 double and/or triple carbon-carbon bonds. For example, polyunsaturated fatty acids can comprise 3-8, 4-7, or 5-6 double and/or triple carbon-carbon bonds.

Currently, the main source of these highly unsaturated fatty acids is fish, with DHA and EPA noted within various blue fish (such as sardines and tuna) at amounts around 20% and 10%, respectively. Yet, if one intends to use fish oil as the sole source of these lipids, several disadvantages exist, such as problems with flavor taint, uncontrollable fluctuations in availability, natural fish oil content variability, as well as the potential to accumulate harmful environmental pollutants. In addition, if one intends to obtain a highly purified (n-3) or (n-6) oil from said sources, it is very difficult to preferentially separate and purify. Specifically, a large market is available within the neonatal supplement market for a highly concentrated form of DHA. If fish oil were to be the source of said products, then DHA would have to be preferentially isolated in large quantities from EPA. Clearly an alternative source of highly purified and production tailored source of these highly unsaturated fatty acids is needed.

In addition to fish oils, various microorganisms (mainly marine) are able to produce and/or accumulate the (n-3) series of docosahexaenoic acid. Of particular interest is the fact that microbial production is not subject to fluctuations caused by external variables such as seasonality, weather and food supply. For example, the following microorganisms are known as having the ability to produce DHA: the deep-sea derived bacterium *Vibrio marinus* (ATCC 15381), *Vibrio* sp. T3615, *Photobacterium profundum* SS9, *Mortierella marina* MP-1 and *Psychromonas kaikoae* (ATCC BAA-363T); microalgal species such as *Crypthecodinium cohnii*, *Cyclotella cryptica*, and *Mortieralla alpina* (1S-4); and the protists *Thraustochytrium* sp. (ATCC 20892), *Thraustochytrium aureum* (ATCC 34304) and *Thraustochytrium roseum*. According to a process utilizing these purified organisms, however, the amount of docosahexaenoic acid produced per gram of biomass per liter is low, being within the range of 10 to 500 mg. Some examples and representative microbial oil producing organisms are shown in FIG. 5.

Omega 3s have been shown to have beneficial effects and the oils and compositions disclosed herein can be used for anti-inflammatory effect on cystic fibrosis (Cochrane Database Syst Rev. 3), rheumatoid arthritis (Drugs 63: 845-53), asthma (Ann Allergy Asthma Immunol 90: 371-7) and thrombotic stroke (Prev Cardiol 6: 38-1), cardio-protective, as well as a direct effect on artheriosclerosis and arrhythmia (Prostaglandins Leukot Essent Fatty Acids. 63:351-62), inhibition of cancer proliferation in breast and prostate cancer cell lines and reduction in animal experiments (Am J Clin Nutr 77: 532-43), anti-psychotic effect on schizophrenia (J Neural Transm Suppl 64:105-17) and other psychiatric diseases (Can J Psychiatry 48: 195-203), immunonutrient supplement used for normal neonatal development and in the treatment of neonatal infections (Eur J Pediatr 162: 122-8), and pathological pain treatment by directly attenuate the neuronal and ganglial processes that underlie neuropathic and inflammatory pain (Prostaglandins Leukot Essent Fatty Acids 68: 219-24).

2. Thraustochytriaceae a) ONC-T18

The marine organism ONC-T18, as disclosed herein, was collected as part of a PUFA producing microbial isolation trip, with over 60 pure cultures isolated (see table 7 for details). Further, ONC-T18 was isolated from the leaves of salt marsh grasses in the Advocate Harbor, Bay of Fundy, Nova Scotia, Canada. Through microscopic examinations and serial culture purification techniques, the strain was believed to be a single microorganism belonging to the genus *Thraustochytrium*. All strains and two ATCC comparison cultures (ATCC 20891 & MYA-1381) were grown on 0.5% glucose, 0.2% peptone, 0.2% yeast extract in sea-water (SW) and underwent GC (fatty acid methyl ester, FAME) analysis.

Figure 6:
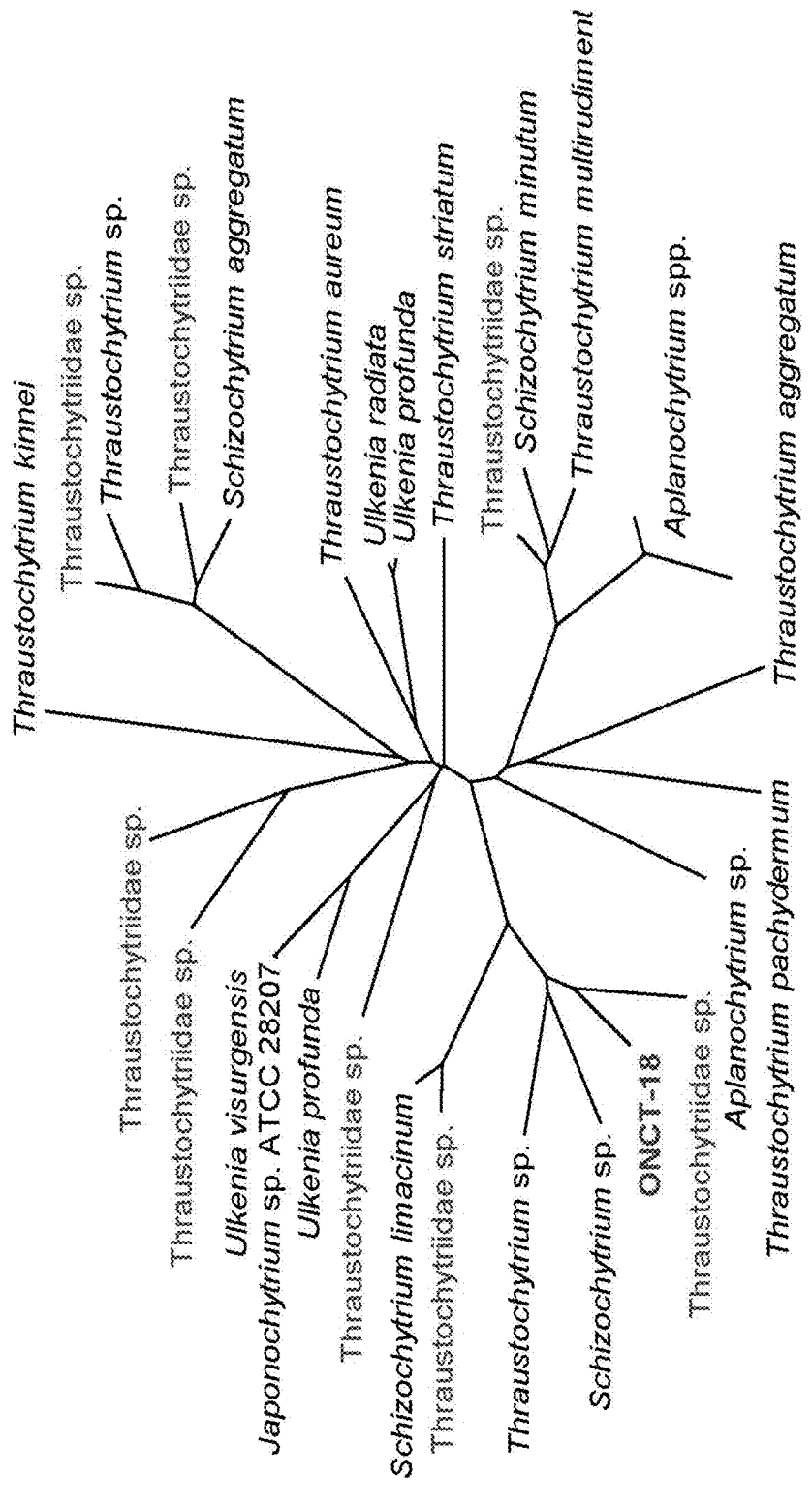
FIG. 6 shows a branched phylogenetic tree of the relationship between the 18S rRNA gene of ONC-T18 and other Thraustochytriales.

FIG. 6 shows a proposed phylogenetic tree of the relationship between ONC-T18, and other closely related organisms.

ONC-T18 was originally isolated as a single microbe using classic pine pollen baiting techniques, followed by culturing on selective medium. Specifically, a nutrient medium containing 5 g L$^{-1}$ glucose, 2 g L$^{-1}$ peptone, 2 g L$^{-1}$ yeast extract to 1 L of 0.2 µm filtered sea water was prepared. The fatty acid profile of ONC-T18 was then determined using the Bligh and Dyer extraction method and PUFA gas chromatographic techniques. Chromatographic results demonstrated the ability of this strain to produce increased amounts of TFA, DHA, as well as marked quantities of EPA and DPA.

The disclosed eukaryotic microorganism can be used in a process for preparing a lipid or fat containing DHA, EPA and DPA, but is not limited to the above-mentioned ONC-T18 or PTA-6245 strain, but any derivation of said strain whether it be via genetic modification, chemical mutagenesis, fermentative adaptation or any other means of producing mutants of the strain, whereby the product of these modifications have genetic or morphological and functional features such as the eukaryotic microorganism, as disclosed herein.

Disclosed are eukaryotic microorganism capable of producing a lipid composition having distinctive lipid class properties, and the solution to the problem of maintaining a stable, reliable and economical source for such a lipid having high functionality and additional value according to the same. Therefore, wild-type strains producing the (n-3) series of DHA and the (n-6) series of DPA to a greater degree as well as variant and recombinant strains designed to produce these polyunsaturated fatty acids to a greater degree are disclosed herein. Such variant or recombinant microorganisms include those designed to have a higher content of said lipids than those produced by the original wild-type strain, when cultured using the same conditions and media. In addition, microorganisms designed to produce a lipid containing similar amounts of the (n-3) series of DHA, EPA and the (n-6) series of DPA can be selected, as compared with the corresponding wild-type strains, effectively using substrates having a superior cost performance, are also included.

Disclosed are compositions comprising a eukaryotic microorganism of the order Thraustochytriales wherein the eukaryotic microorganism produces unsaturated fatty acids. The polyunsaturated fatty acids can be, for example, omega 3 or omega 6 fatty acids, such as DHA and DPA.

Disclosed are compositions comprising a eukaryote, wherein the composition produces a lipid.

Also disclosed are compositions wherein the lipid comprises a lipid as disclosed herein.

Also disclosed are compositions, wherein the eukaryote comprises a member of the order Thraustochytriales.

Also disclosed are compositions, wherein the eukaryote has a 18S ribosome RNA gene sequence having at least 80% identity to SEQ ID NO:1.

It is understood that any form of characterization described herein, such as by genetics or by the lipid signatures or by the classifications, for the eukaryotic microorganisms can be used to characterize the microorganisms as disclosed herein. The eukaryotic microorganism can comprise one or more microorganisms from the family Thraustochytriaceae, and examples are ATCC accession number 20888, 20889, 20890, 20891, and 20892. There are a variety of characteristics that can be used related to the organisms and the unsaturated fatty acids they produce. It is understood that these can be used in any combination or permutation to define a set or sets of organisms or oils or antioxidants, for example. One characteristic is the classification of the organisms themselves, the genetic identification of the organisms, the lipid and antioxidant profiles of the organisms, and the growth conditions of the organisms, for example.

b) Classification

The eukaryotic microorganism can be from the phylum Labyrinthulomycota. The eukaryotic microorganism can be from the class Labyrinthulomycetes. The eukaryotic microorganism can be from the subclass Thraustochytridae. The eukaryotic microorganism can be from the order Thraustochytriales. The eukaryotic microorganism can be from the family Thraustochytriaceae. The eukaryotic microorganism can be from the genus *Thraustochytrium*. The eukaryotic microorganism can be a *Thraustochytrium* sp. The eukaryotic microorganism can be *Thraustochytrium aureum*. The eukaryotic microorganism can be *Thraustochytrium roseum*. The eukaryotic microorganism can be *Thraustochytrium striatum*. The eukaryotic microorganism can be from the genus *Schizochytrium*. The eukaryotic microorganism can be *Schizochytrium* sp. The eukaryotic microorganism can be a modified version of any of the listed eukaryotic microorganisms. The eukaryotic microorganism can also comprise any currently unknown or isolated members of said prokaryotes class, subclass, order, family or genus. A combination of eukaryotic microorganisms can be any combination of any organisms disclosed herein, including, one or more of the *Thraustochytrium* sp., *Schizochytrium* sp., *Thraustochytrium aureum*, *Thraustochytrium striatum* and *Thraustochytrium roseum*.

The eukaryotic microorganisms from the family Thraustochytriaceae can be any of those disclosed above. The eukaryotic microorganism can comprise the organism having ATCC accession number PTA-6245.

c) Genetics

The eukaryotic microorganism can have 18S rRNA sequence SEQ ID NO:1. The eukaryotic microorganism can have an 18S rRNA sequence that, for example, has about 90% homology, or any other identity disclosed herein, to SEQ ID NO:1. The eukaryotic microorganism can have an 18S rRNA sequence that hybridizes under stringent conditions, or any other conditions as disclosed herein, to SEQ ID NO:1, or a portion of SEQ ID NO:1.

The sequence similarity/identity and nucleic acid hybridization of the nucleic acids of the organisms can be as described herein. Specifically, comparison of SEQ ID NO:1 with nucleic acid sequences found in the genomic database, GenBank (National Centre for Biotechnology Information, National Institute of Health, Bethesda, Md., USA) using the BLAST (Basic local alignment search tool) algorithm identified SEQ ID NO:1 as being related (91% similarity) to several eukaryotic *Thraustochytrid* species, closely related to *Thraustochytrium* sp. CHN-1 [AB126669] (94.5% similarity) and *Thraustochytriidae* sp. N1-27 [AB073308] (95.5% similarity), and most closely related to *Thraustochytrium striatum* [AF265338] (97.5% similarity).

3. (1) Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of nucleic acids and proteins herein disclosed typically have at least, about 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2:482, 1981, by the homology alignment algorithm of Needleman and Wunsch, *J. Mol. Biol.* 48:443, 1970, by the search for similarity method of Pearson and Lipman, *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

(2) Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the $T_m$ (the melting temperature at which half of the molecules dissociate from their hybridization partners) followed by washing at a combination of temperature and salt concentration chosen so that the washing temperature is about 5-20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed under conditions where both the limiting and non-limiting primer are for example, 10, 100 or 1000 fold below their $k_d$, or where only one of the nucleic acid molecules is 10, 100 or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 10 percent of the primer is enzymatically manipulated under conditions which promote the enzymatic manipulation, for example if the enzymatic manipulation is DNA extension, then selective hybridization conditions would be when at least about 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example, if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

b) Composition of Molecules Produced

It is understood that the eukaryotes disclosed herein are capable of producing a number of compounds and compositions. The compounds and compositions can be used as a signature, a way of identifying the organism. For example, one way of characterizing an organism is by the lipid profile that the organism produces. As disclosed herein these various lipid profiles can be used to characterize the organism as well as be purified, manipulated, and collected for a variety of reasons.

(1) Lipids

It is understood that each organism can produce some profile of unsaturated fatty acids, as disclosed herein. These profiles are characteristics of the organisms. Below are some examples, of unsaturated and other lipid profiles for the organisms.

The eukaryotic microorganism can produce, for example a lipid or fatty acid fraction of at least about 4 wt. % to 6 wt. % (e.g., about 5 wt. %), which comprises from about 0 wt. % to about 2 wt. % myristic acid (e.g., about 1 wt. %), from about 16 wt. % to about 20 wt. % (e.g., about 18 wt. %) palmitic acid, from about 0 wt. % to about 2 wt. % (e.g., about 1 wt. %) palmitoleic acid, from about 4 wt. % to about 8 wt. % (e.g., about 6 wt. %) stearic acid, from about 30 wt. % to about 34 wt. % (e.g., about 32 wt. %) oleic acid, from about 40 wt. % to about 44 wt. % (e.g., about 42 wt. %) linoleic acid, and from about 0 wt. % to about 3 wt. % (e.g., about 2 wt. %) n-3 EPA per dried cellular biomass.

The eukaryotic microorganism can also produce, for example, a lipid or fatty acid fraction of at least about 1 wt. % to 3 wt. % (e.g., about 1.25 wt. %), which comprises from about 2 wt. % to about 4 wt. % (e.g., about 3 wt. %) myristic acid, from about 50 wt. % to about 60 wt. % (e.g., about 55 wt. %) palmitic acid, from about 2 wt. % to about 4 wt. % (e.g., about 3 wt. %) palmitoleic acid, from about 16 wt. % to about 20 wt. % (e.g., about 18 wt. %) stearic acid, from about 9 wt. % to about 13 wt. % (e.g., about 11 wt. %) oleic acid, from about 1 wt. % to about 3 wt. % (e.g., about 2 wt. %) eicosadienoic acid, and from about 6 wt. % to about 10 wt. % (e.g., about 8 wt. %) n-3 EPA per dried cellular biomass.

The eukaryotic microorganism, for example, such as ONC-T18, can produce at least about 30 wt. %, 40 wt. %, 50 wt. %, 60 wt. %, 70% wt. % or 80 wt. % (e.g., about 80 wt. %) of a lipid composition per dried cellular biomass. For example, the eukaryotic microorganism can produce a lipid composition comprising from about 25% to about 40% of an omega-3 fatty acid, such as n-3 DHA, (for example, at least 15%, 20%, 25%, 30%, 35%, 40%, 45%, 50%, 55% or 60% by weight), and from about 0% to about 3% of the omega-3 fatty acid, EPA, (for example, at least 1% or 2% by weight) and from about 4% to about 12% of an omega-6 fatty acid, such as n-6 DPA, (for example, at least 4%, 5%, 6%, 7%, 8%, 9%, or 10% by weight).

It is understood that the composition of the lipid produced by the eukaryotic microorganism can be manipulated based on the growing conditions the eukaryotic microorganism exists in. By changing various parameters, as disclosed herein, the compositions can be manipulated to produce, for example a better yield of DHA or DPA. For example, the manipulation may not produce more actual grams, but the manipulation, may produce a better ratio of DHA or DPA to EPA and other desired PUFAs, which may be desirable from a purification standpoint. Varying conditions are discussed herein.

FIG. 10 shows a possible metabolic pathway for the various PUFAs produced by the disclosed eukaryotic microorganism, consistent with fatty acid methyl ester metabolite tracking. Proteins which can be identified within the pathways which as disclosed herein are polyketide synthase, using for example a degenerative primer study, (Metz et al. (2001) Science 293:290-3 and Kaulmann & Hertweck (2002) Angew. Chem. Int. Ed. 41:1866-9). Also elongases and desaturases, using for example a hybridization probe study can be identified. Also fatty acid synthases can be identified using, for example, a hybridization probe and/or a degenerative primer study.

4. Growing and Culturing

A phenotypic microplate study including carbon; nitrogen (peptide nitrogen); phosphorus and sulfur; osmolytes, and pH was performed.]

An Orthogonal array (Taguchi) method was used to determine optimum media configurations and variations in nitrogen, carbon and salt concentration (Joseph J & Piganatiells J R (1998) IIE Trans, 20:247-254).

If you increase agitation or $dO_2$ you increase biomass production & TFA but decrease DHA. If you decrease agitation or $dO_2$ you decrease cellular biomass (g) & decrease TFA but increase DHA but also reduce C16:0, C16:1 & C18:1.

If you increase temperature you increase biomass production & TFA but decrease DHA. If you decrease temperature you decrease cellular biomass (g) & decrease TFA but increase DHA, but reduce C16:0, C16:1 & C18:1.

Cellular biomass derived from the disclosed eukaryotic microorganism can be obtained by inoculating a suitable natural or artificial seawater medium, containing from about 2% to about 100% of seawater. This eukaryotic microorganism is able to utilize various nutritional components within this medium. Examples of a carbon source used within the medium are carbohydrates such as glucose, fructose, dextrose, lactulose, galactose, maltotriose, maltose, lactose, glycogen, gelatin, starch (corn or wheat) as well as sugar derivatives such as acetate, m-inositol (derived from corn steep liquor), galacturonic acid (derived from pectin), L fucose (derived from galactose), gentiobiose, glucosamine, α-D-glucose-1-phosphate (derived from glucose), cellobiose (derived from cellulose) dextrin (derived from corn) and a-cyclodextrin (derived from starch) and polyols such as maltitol, erythritol, adonitol and oleic acids such as glycerol and tween 80 and amino sugars such as N-acetyl-D-galactosamine, N-acetyl-D-glucosamine and N-acetyl-β-D-mannosamine. While, examples of a nitrogen source are natural nitrogen sources such as peptone, yeast extract, malt extract and fish meal, or an organic nitrogen sources such as sodium glutamate, but not limited thereto. Furthermore, if necessary phosphates, such as potassium phosphate, and sodium phosphate, inorganic salts such as, ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride and calcium chloride may be used as trace nutrients, along with the chelating compound, ethylenediaminetetraacetic acid, alone or in conjunction with vitamins such as pyridoxine hydrochloride, thiamine hydrochloride, calcium pantothenate, p-aminobenzoic acid, riboflavin, nicotinic acid, biotin, folic acid and vitamin $B_{12}$. After preparing the medium, the pH is adjusted to between 3.0 and 10.0 using acid or base to adjust where appropriate, for example between pH 4.0 and 6.5, and the medium is sterilized by autoclaving, for example. Cultivation can be carried out for 1 to 30 days, 1 to 21 days, 1 to 15 days, 1 to 12 days, 1 to 9 days, or preferably 3 to 5 days at temperatures between 4 to 30° C., preferably 18 to 28° C., by aeration-shaking culture, shaking culture, stationary culture, batch culture, continuous culture, rolling batch culture, or wave culture, or the like.

The following conditions are an example of conditions that can allow for the production of a set of lipids in yields which allows for their use as a commodity. Investigation of culture conditions for ONC-T18 revealed that the eukaryotic microorganism disclosed herein grows well in natural or artificial sea water or in a medium containing down to 5% concentration of natural or artificial sea water. Carbon and nitrogen sources added to the medium may be those conventionally used as described above. The nitrogen source being either natural or organic in nature is relatively equal and total nitrogen concentration within the medium is kept constant. These sources are added to the medium at standard concentrations. If these conditions are met, little influence on the content of lipid, proportions or the amount of accumulated DHA, DPA and EPA is produced, as disclosed herein.

For high-concentration fermentation of ONC-T18, it is possible to use several methods to increase both cellular biomass and lipid production rates. These include, increasing both the carbon and nitrogen concentration in the medium (at a ratio of between 6:1 and 15:1, preferably between 6:1 and 13:1 and at temperatures between 4 to 30° C., preferably 18 to 28° C.) from the range 5 g $L^{-1}$ to 60 g $L^{-1}$ to the range 100 g $L^{-1}$ and 160 g $L^{-1}$ and from the range 4 g $L^{-1}$ to 10 g $L^{-1}$ to the range 40 g $L^{-1}$ to 60 g $L^{-1}$, respectively. Using this method the proportion of biomass and lipid produced is also increased at comparable rates. Furthermore, it is possible to increase lipid production through the use of increased carbon sources from the range 5 g $L^{-1}$ to 60 g $L^{-1}$ to the range 100 g $L^{-1}$ and 160 g $L^{-1}$, while the nitrogen source remains constant. Additionally, it is possible to increase biomass production while maintaining lipid content, through the use of increased amounts of nitrogen sources from the range 10 g $L^{-1}$ to 60 g $L^{-1}$ while the carbon source remains constant. Moreover, experimentation has determined that biomass and lipid production greatly increases with increased agitation from the range 100 and 1000 rpm, better at between 350 and 600 rpm and optimal at between 350 and 450 rpm, with only a marginal decrease in lipid content and no decrease in fatty acid profiles, with agitation particularly relevant at the early stages of heterotrophic fermentation. Experimentation has also determined that lipid production optima are achieved when the dissolved oxygen content of the culture medium is between 1 and 10%, optimally at 5%. Finally, the addition of acetate, trace elements, metals and vitamins to the production medium (as mentioned above) increases the production of DHA, EPA and DPA with respect to other fatty acids without decreasing total lipid values.

By performing heterotrophic fermentation as described above, it is possible to consistently produce cellular biomass which produces a lipid containing the (n-3) series of DHA in a culture of high concentration of not less than 5 g and more preferably not less than 20 g/L medium. Furthermore, experimentation has shown that most of these lipids accumulate during the later-exponential/transition stages of cultivation, after maximal biomass levels are reached. Yet, during the fermentation process, lipid content typically does not fall below 25% of the total biomass, typically maximizing at around 80%. The cultivation under the above conditions can be carried out using a conventional agitation-fermenter. It is also possible to use a bubble column fermenter (batch or continuous cultures), or a wave fermentor.

Collection of cellular biomass prior to processing for lipid separation can be performed using various conventional methods such as centrifugation (such as solid-ejecting centrifuges) or filtration (such as cross-flow filtration) and may also include the use of a precipitation agent for the accelerated collection of cellular biomass (such as sodium phosphate, calcium chloride or polyacridamide).

5. Isolation of Lipid

Figure 7:
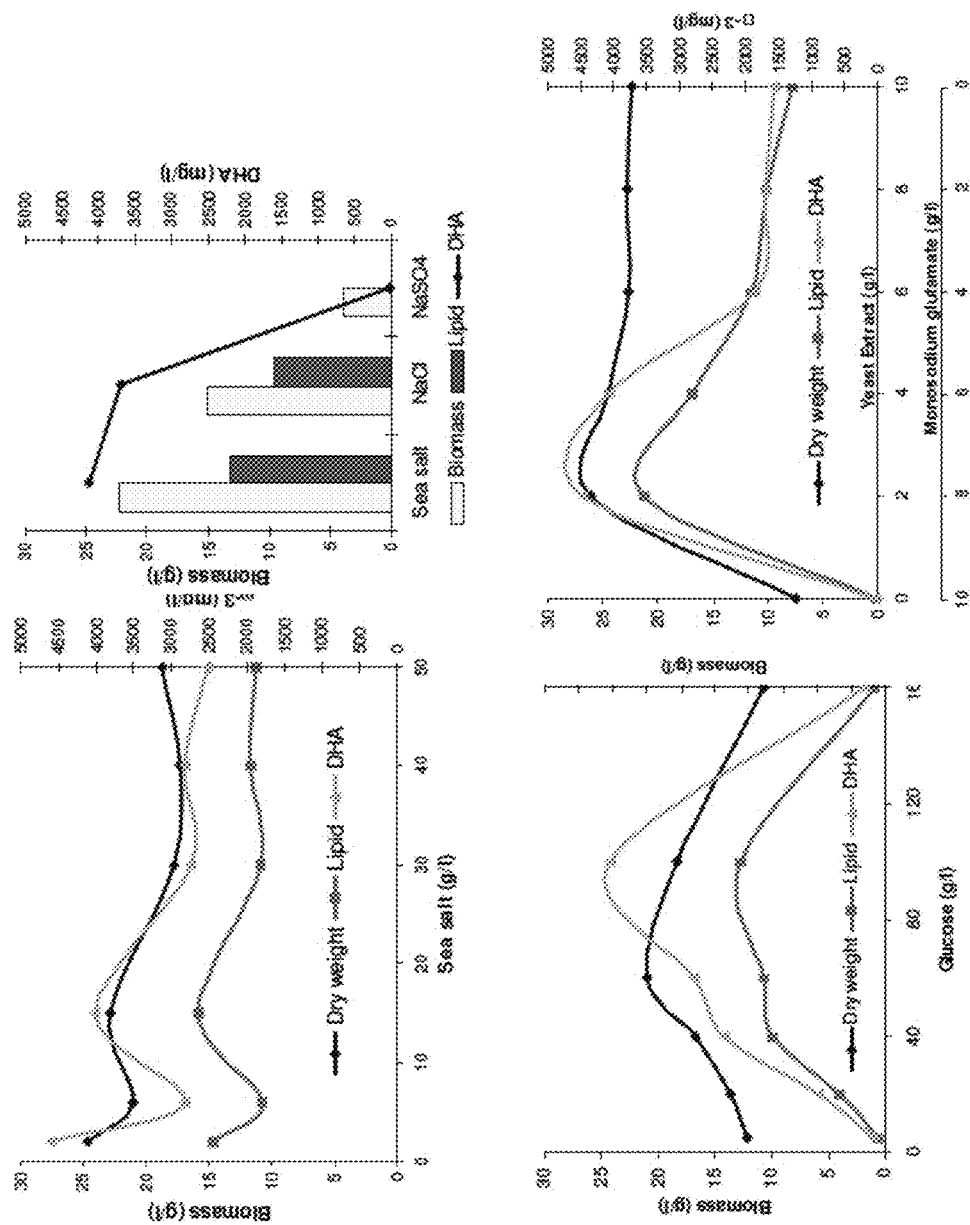
FIG. 7 shows lipid and DHA production of ONC-T18 under different conditions.
Figure 8:
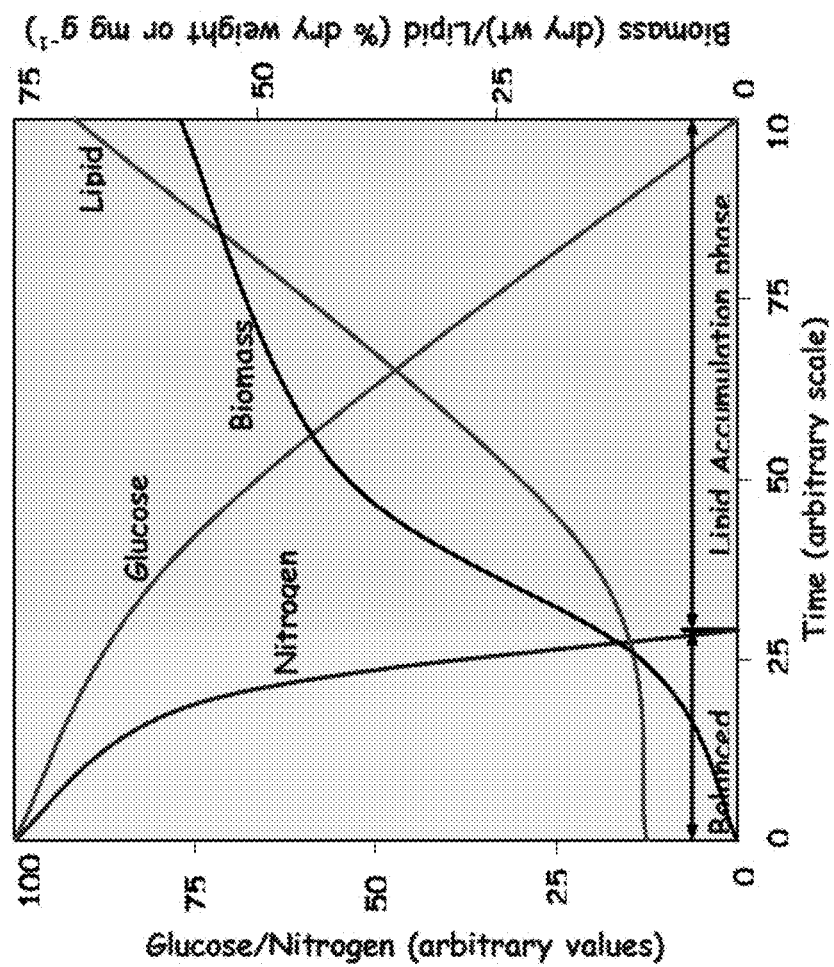
FIG. 8 shows a modified graph with information about growth conditions on it for the eukaryotes disclosed herein. (Modified from Ratledge, C. (2004), Lipid Technol. 16:34-39).

FIG. 7 shows lipid and DHA profiles as functions of a variety of parameters. All of this data can be used to extract specific characteristics about the ONC-T18 eukaryotic microorganism. FIG. 13 shows a general fatty acid profile for the disclosed eukaryote.

The fat containing the (n-3) series of DHA and the (n-6) series of DPA can be obtained by breaking or disrupting the collected cell biomass, for example, via milling, ultrasonication, and then carrying out extraction with a solvent such as chloroform, hexane, methanol, ethanol or via supercritical fluid extraction means. The content of the resultant fat containing the (n-3) series of DHA and the (n-6) series of DPA per gram of dried cellular biomass is preferably greater than 0.25 g and more preferably greater than 0.6 g.

The disclosed eukaryotic microorganisms, such as ONC-T18, are able to produce lipid thus obtained, any of its variants and any associations between members of the same species of eukaryotic microorganisms whereby the lipid profile is as follows. The percentage of neutral lipids can be at least 95% by weight of total lipids. A typical composition of fatty acids for the eukaryotic microorganism, such as ONC-T18, in the neutral lipids is as follows: 15% of myristic acid, 8% of pentadecanoic acid, 35% of palmitic acid, 7% of palmitoleic acid, 1% of stearic acid, 2% of oleic acid, 1% of eicosapentaenoic acid, 6% of docosapentaenoic acid and 25% docosahexaenoic acid (GC spectra shown in FIG. 1).

The disclosed eukaryotic microorganisms, such as ONC-T18, are able to produce lipid thus obtained, any of its variants and any associations between members of the same species of eukaryotic microorganisms whereby the lipid profile is as follows. The percentage of mono-, di- and tri-glycerides in the neutral lipid fraction of ONC-T18 is 0% to about 2%, 0 to about 2% and 96 to about 100%, respectively. While the polar lipid fraction with comprises between 5% and about 10% of the lipid fraction, comprises phosphotidylcholine, phosphotidylserine and phosphotidic acid both bound and unbound to neutral lipids.

It is understood that these lipids can be found in any combination or permutation within the organism. It is also understood that the concentrations of these lipids can be manipulated by changing the growing conditions and media conditions as discussed herein.

(1) Lipid as Concentration

The eukaryotic microorganism can produce a lipid fraction comprising n-3 DHA, EPA and n-6 DPA at greater than or equal to about 4.0 g $L^{-1}$ of medium. The eukaryotic microorganism can produce a lipid composition comprising n-3 DHA, EPA and n-6 DPA at greater than or equal to about 20.0 g $L^{-1}$ of medium. The eukaryotic microorganism can produce a lipid composition comprising n-3 DHA, EPA and n-6 DPA at greater than or equal to about 14.0 g $L^{-1}$ of medium. The eukaryotic microorganism can produce from about 1.5 g $L^{-1}$ to about 5.0 g $L^{-1}$ (e.g., about 4.6 g $L^{-1}$) of the n-3 DHA, from about 0.5 g $L^{-1}$ to about 1.5 g $L^{-1}$ (e.g., about 0.22 g $L^{-1}$) of the n-3 EPA, and from about 0.5 g $L^{-1}$ to about 1.5 g $L^{-1}$ of the n-6 DPA. Furthermore, the eukaryotic microorganism can produce a lipid fraction comprising myristic, myristoleic, pentadecanoic, palmitic, palmitoleic, stearic oleic, linoleic, eicosadienoic, arachidonic, eicosapentaenoic, docosahexanoic and docosapentaenoic acids between 301.2 and 360.3 mg $g^{-1}$ or even up to 790 mg $g^{-1}$ of cellular biomass. The eukaryotic microorganism can also produce a fraction comprising between 44.3 and 57 mg $g^{-1}$ myristic acid (equal to 1134.5 to 1458.1 mg $L^{-1}$), 0.5 to 0.65 myristoleic acid (equal to 13.3 to 16.63 mg $L^{-1}$), 33.5 to 34.6 mg $g^{-1}$ pentadecanoic acid (equal to 856.9 to 885.1 mg $L^{-1}$), 121.9 and 165.1 mg $g^{-1}$ palmitic acid (equal to 3118.2 to 4223.3 mg $L^{-1}$), 7.9 to 28.5 mg $g^{-1}$ palmitoleic acid (equal to 202.1 to 729 mg $L^{-1}$), 4.38 to 5.9 mg $g^{-1}$ stearic acid (equal to 112 to 151 mg $L^{-1}$), 6.94 to 9.9 mg $g^{-1}$ oleic acid (equal to 177.5 to 253.2 mg $L^{-1}$), 0.4 to 1.3 mg $g^{-1}$ linoleic acid (equal to 11.26 to 33.3 mg $L^{-1}$), 0.5 to 1.0 mg $g^{-1}$ eicosadienoic acid (equal to 12.8 to 25.6 mg $L^{-1}$), 0.4 to 0.5 mg $g^{-1}$ arachidonic acid (equal to 10.2 to 13 mg $L^{-1}$), 75 to 100 mg $g^{-1}$ docosahexanoic acid (equal to 1918 to 2560 mg $L^{-1}$), 1.9 to 6 mg $g^{-1}$ eicosapentaenoic acid (equal to 48.6 to 153.5 mg $L^{-1}$) and 17.1 to 33.7 mg $g^{-1}$ docosapentaenoic acid (equal to 437.4 to 862.1 mg $L^{-1}$), having a total fatty acid content within the cellular biomass of between 301 to 790 mg $g^{-1}$ (equal to 7700 to 20,209 mg $L^{-1}$).

(2) Other Molecules

The eukaryotic microorganism can further produce carotenoids and xanthophylls. Examples of such carotenoids and xanthophylls include beta-carotene, lycopene, astaxanthin, canthaxanthin, phoenicoxanthin, zeaxanthin, echinenone, beta-cryptoxanthin, capsanthin, lutin, annatto, beta-apo-8-carotenal and beta-apo-8-carotenal-ester.

The xanthophylls produced by the disclosed eukaryotic microorganisms can be conjugated with the various PUFAs also produced by the disclosed eukaryotic microorganisms.

(a) Antioxidants

Generally, antioxidants are compounds that react with, and typically get consumed by oxygen. Since antioxidants typically react with oxygen, antioxidants also typically react with the free radical generators, and free radicals. ("The Antioxidants—The Nutrients that Guard Your Body" by Richard A. Passwater, Ph. D., 1985, Keats Publishing Inc., which is herein incorporated by reference at least for material related to antioxidants). The compositions can contain any antioxidants, and a non-limiting list would included but not be limited to, non flavonoid antioxidants and nutrients that can directly scavenge free radicals including multi carotenes, beta-carotenes, alpha-carotenes, gamma-carotenes, lycopene, lutein and zeaxanthins, selenium, Vitamin E, including alpha-, beta- and gamma-(tocopherol, particularly alpha-tocopherol, etc., vitamin E succinate, and trolox (a soluble Vitamin E analog) Vitamin C (ascorbic acid) and Niacin (Vitamin $B_3$, nicotinic acid and nicotinamide), Vitamin A, 13-cis 30 retinoic acid, N-acetyl-L-cysteine (NAC), sodium ascorbate, pyrrolidin-edithio-carbamate, and coenzyme $Q_{10}$; enzymes which catalyze the destruction of free radicals including peroxidases such as glutathione peroxidase (GSHPX) which acts on $H_2O_2$ and such as organic peroxides, including catalase (CAT) which acts on $H_2O_2$, superoxide dismutase (SOD) which disproportionates $O_2H_2O_2$, glutathione transferase (GSHTx), glutathione reductase (GR), glucose 6-phosphate dehydrogenase (G6PD), and mimetics, analogs and polymers thereof (analogs and polymers of antioxidant enzymes, such as SOD, are described in, for example, U.S. Pat. No. 5,171,680 which is incorporated herein by reference for material at least related to antioxidants and antioxidant enzymes); glutathione; ceruloplasmin; cysteine, and cysteamine (beta-mercaptoethylamine) and flavenoids and flavenoid like molecules like folic acid and folate. A review of antioxidant enzymes and mimetics thereof and antioxidant nutrients can be found in Kumar et al, *Pharmac. Ther.* 39: 301, 1988 and Machlin L. J. and Bendich, *FASEB Journal* 1:441-445, 1987 which are incorporated herein by reference for material related to antioxidants.

Flavonoids, also known as "phenylchromones," are naturally occurring, water-soluble compounds which have antioxidant characteristics. Flavonoids are widely distributed in vascular plants and are found in numerous vegetables, fruits and beverages such as tea and wine (particularly red wine). Flavonoids are conjugated aromatic compounds. The most widely occurring flavonoids are flavones and flavonols (for example, myricetin, (3,5,7,3',4',5',-hexahydroxyflavone), quercetin (3,5,7,3',4'-pentahydroxyflavone), kaemferol (3,5,7,4'-tetrahydroxyflavone), and flavones apigenin (5,7,4'-trihydroxyflavone) and luteolin (5,7,3',4'-tetrahydroxyflavone) and glycosides thereof and quercetin).

Carotenoids are important natural pigments produced by many microorganisms and plants, usually red, orange or yellow in color. Traditionally, carotenoids have been used in the feed, food and nutraceutical industries. They are known to be essential for plant growth and photosynthesis, and are a main dietary source of vitamin A in humans. Dietary antioxidants, such as carotenoids (beta-carotene, lycopene, astaxanthin, canthaxanthin, zeaxanthin, capsanthin, lutein, annatto, beta-apo-8-carotenal and beta-apo-8-carotenal-ester), exhibit significant anticancer activities and play an important role in the prevention of chronic diseases. Carotenoids are potent biological antioxidants that can absorb the excited energy of singlet oxygen onto the carotenoid chain, leading to the degradation of the carotenoid molecule but preventing other molecules or tissues from being damaged.

Oxygen is required for metabolic functions, but it also presents challenges to cells. The human organism has a wide range of metabolic enzymes and antioxidants to rid its cells of oxygen derived molecules. This oxidative stress is supposed to be a contributing factor in conditions such as rheumatoid arthritis, ischemic heart disease and stroke, Alzheimer's dementia, cancer and ageing. Therefore, antioxidants have the potential to protect against a wide spectrum of diseases. Several antioxidant compounds have been isolated from marine microbial sources; these include astaxanthin, beta-carotene and other carotenoids.

Carotenoids are a widely distributed group of naturally occurring pigments, with over 700 natural lipid-soluble pigments primarily produced by microalgal, macroalgal, bacterial and fungal species, with astaxanthin and its derivatives being of particular interest commercially. Astaxanthin is an extremely effective antioxidant protector. Yet, unlike beta-carotene, astaxanthin readily crosses the blood-brain/retina barrier, and therefore also has potential to protect from diseases of the brain and the eyes. Preclinical studies suggest various beneficial effects of consuming astaxanthin such as: (i) inhibit cancer formation and growth in the bladder, colon, liver, mammary and the oral cavity; (ii) protect the retina of the eye from oxidative damage and thus has an effect against age related macular disease; (iii) promote increased immune activity, (iv) provide protection from ultraviolet light damage, as well as (v) provide increased muscle endurance.

(b) Isolation of Microorganisms

Disclosed are microorganisms from the family Thraustochytriaceae obtained by a method comprising baiting a vegetative sample in salt water (natural sea or artificial) with pollen grains and incubating; separating and transferring the grains to a heterotrophic medium and incubating; identifying an isolate that produces fatty acids, isolating from the identified isolate the microorganism from the family Thraustochytriaceae. Additional forms of isolation include media supplemented with appropriate antibiotics and identification via either by microscopic means as mentioned above or via the use of 18S rRNA gene primers or probes. The heterotrophic medium can be as described below.

6. Lipids and Other Molecules Produced by the Eukaryotic Microorganism

Disclosed are lipid compositions comprising from about 25 wt. % to about 40 wt. % of n-3 DHA, from about 6 wt. % to about 10 wt. % of n-6 DPA, and from about 0 wt. % to about 3 wt. % of n-3 EPA.

The lipid composition can further comprise from about 11 wt. % to about 15 wt. % (e.g., about 13 wt. %) myristic acid, from about 7 wt. % to about 11 wt. % (e.g., about 9 wt. %) pentadecanoic acid, from about 37 wt. % to about 41 wt. % (e.g., about 39 wt. %) palmitic acid, from about 3 wt. % to about 7 wt. % (e.g., about 5 wt. %) palmitoleic acid, from about 0 to about 3 wt. % (e.g., about 1 wt. %) stearic acid, or from about 1 wt. % to about 4 wt. % (e.g., about 2 wt. %) oleic acid.

The lipid composition can comprise n-3 DHA in concentrations in excess of about 400 mg of biomass, n-6 DPA in concentrations in excess of 100 mg of biomass.

The lipid composition can further comprise carotenoids. Examples of such carotenoids include beta-carotene, lycopene, astaxanthin, zeaxanthin, canthaxanthin, echinenone, phoenicoxanthin, capsanthin, lutein, annatto, beta-apo-8-carotenal, and beta-apo-8-carotenal-ester.

In one aspect, the composition can comprise at least about 24 wt. % n-3 DHA, about 1 wt. % n-3 DPA, about 6 wt. % n-6 DPA, and about 1 wt. % n-3 EPA.

7. Composition Containing the Molecules Produced by the Eukaryotic Microorganism A foodstuff, supplement, pharmaceutical composition for both human and animal (including marine) can comprise the composition (lipid, lipid with antioxidant and antioxidant alone).

Also disclosed is an infant formula comprising the composition (lipid, lipid with antioxidant and antioxidant alone).

C. METHODS

1. Methods of Making Lipids

Disclosed are methods of preparing a lipid composition, the method comprising: culturing a eukaryotic microorganism comprising one or more microorganisms from the family Thraustochytriaceae, and isolating the lipid composition.

A variety of procedures can be employed in the recovery of the resultant cellular biomass from fermentation in various culture media, such as by filtration or centrifugation. The cells can then be washed, frozen, lyophilized, or spray dried, and stored under a non-oxidizing atmosphere to eliminate the presence of oxygen, prior to incorporation into a processed food or feed product.

Cellular lipids containing the (n-3) DHA, EPA and (n-6) DPA PUFAs can also be extracted from the cellular biomass methods such as supercritical fluid extraction, or by extraction with solvents such as chloroform, hexane, methylene chloride, or methanol, and the resulting extract evaporated under negative pressure to produce a sample of concentrated lipid material. The omega-3 and omega-6 PUFAs may be further concentrated by hydrolyzing the lipids and concentrating the highly unsaturated fraction by employing traditional methods such as urea adduction or fractional distillation, column chromatography, or by supercritical fluid fractionation. The cells can also be broken or lysed and the lipids extracted into vegetable or animal (e.g. fish oils) oils. The extracted oils can be refined by well-known processes routinely employed to refine vegetable oils (e.g. by chemical or physical refining). These refining processes remove impurities from extracted oils before they are used or sold as edible oils. After refining, the oils can be used directly as a feed or food additive to produce omega-3 and/or omega-6 enriched products. Alternatively, the oil can be further processed and purified as outlined below and then used in the above applications and also in pharmaceutical applications.

In another process for the production of enriched (concentrated) omega-3 or omega-6 oils, the harvested cellular biomass (fresh or dried) can be ruptured or permeabilized by well-known techniques such as sonication, liquid-shear disruption methods, bead milling, pressing under high pressure, freeze-thawing, or enzymatic digestion of the cell wall. The lipids from the ruptured cells are extracted by use of a solvent or mixture of solvents such as hexane, chloroform, ether, or methanol. The solvent is removed and the lipids hydrolyzed by using any of the well-known methods for converting triglycerides to free fatty acids or esters of fatty acids including base, acid, or enzymatic hydrolysis. After hydrolysis is completed, the nonsaponifiable compounds are extracted into a solvent such as ether, hexane or chloroform and removed. The remaining solution is then acidified by addition of an acid, and the free fatty acid extracted into a solvent such as hexane, ether or chloroform. The solvent solution containing the free fatty acids can then be cooled to a temperature low enough for crystallization of the non PUFA compounds, which can then be removed via filtration, centrifugation or settling. Resulting in the concentration of the remaining PUFA compounds and used as a nutritional supplements for humans, as a food additive, or as pharmaceutical applications.

Also, disclosed is a lipid composition prepared by the method disclosed above.

The microorganisms from the family Thraustochytriaceae can be any of the microorganisms disclosed above.

a) Medium

Figure 9:
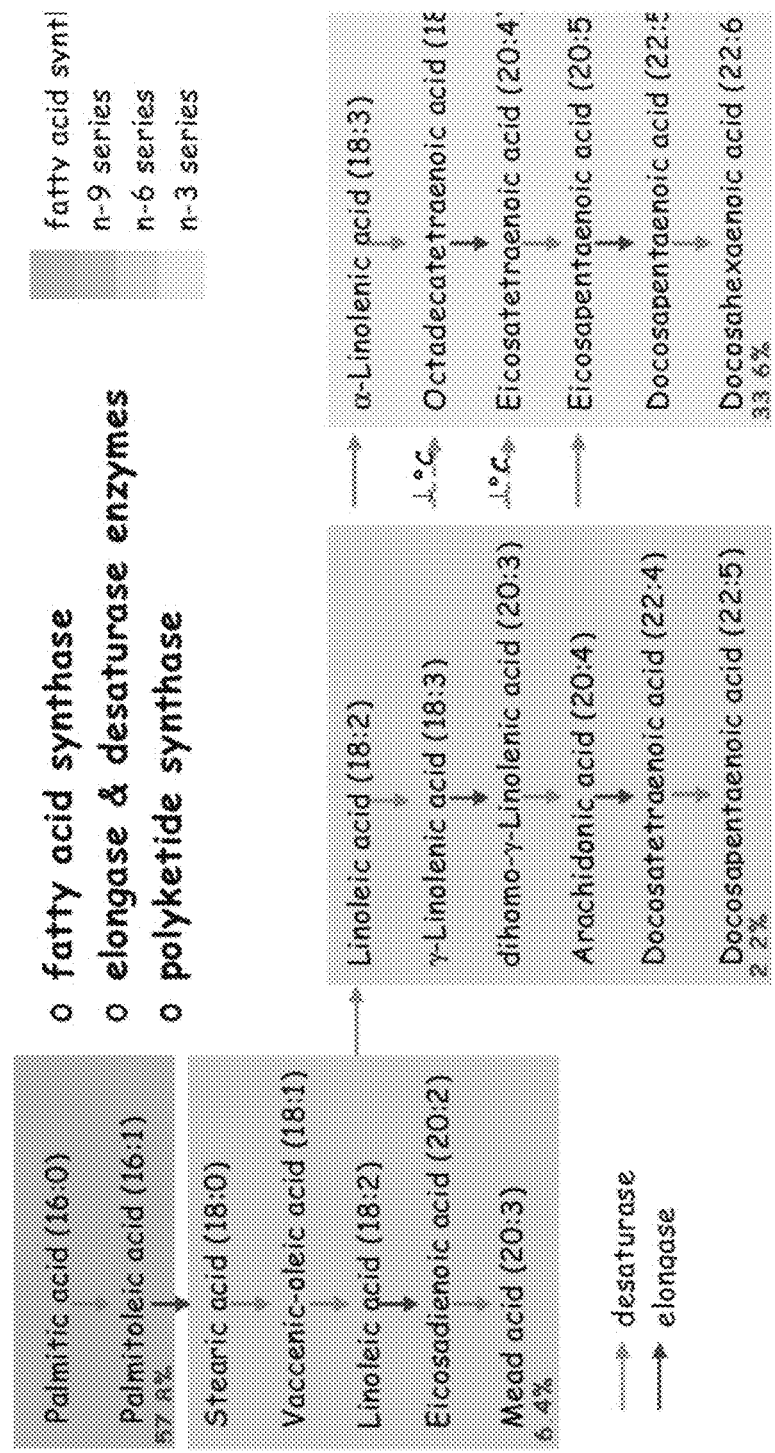
FIG. 9 shows a proposed metabolic pathway for the production of PUFAs for the disclosed eukaryotes.
Figure 11A:
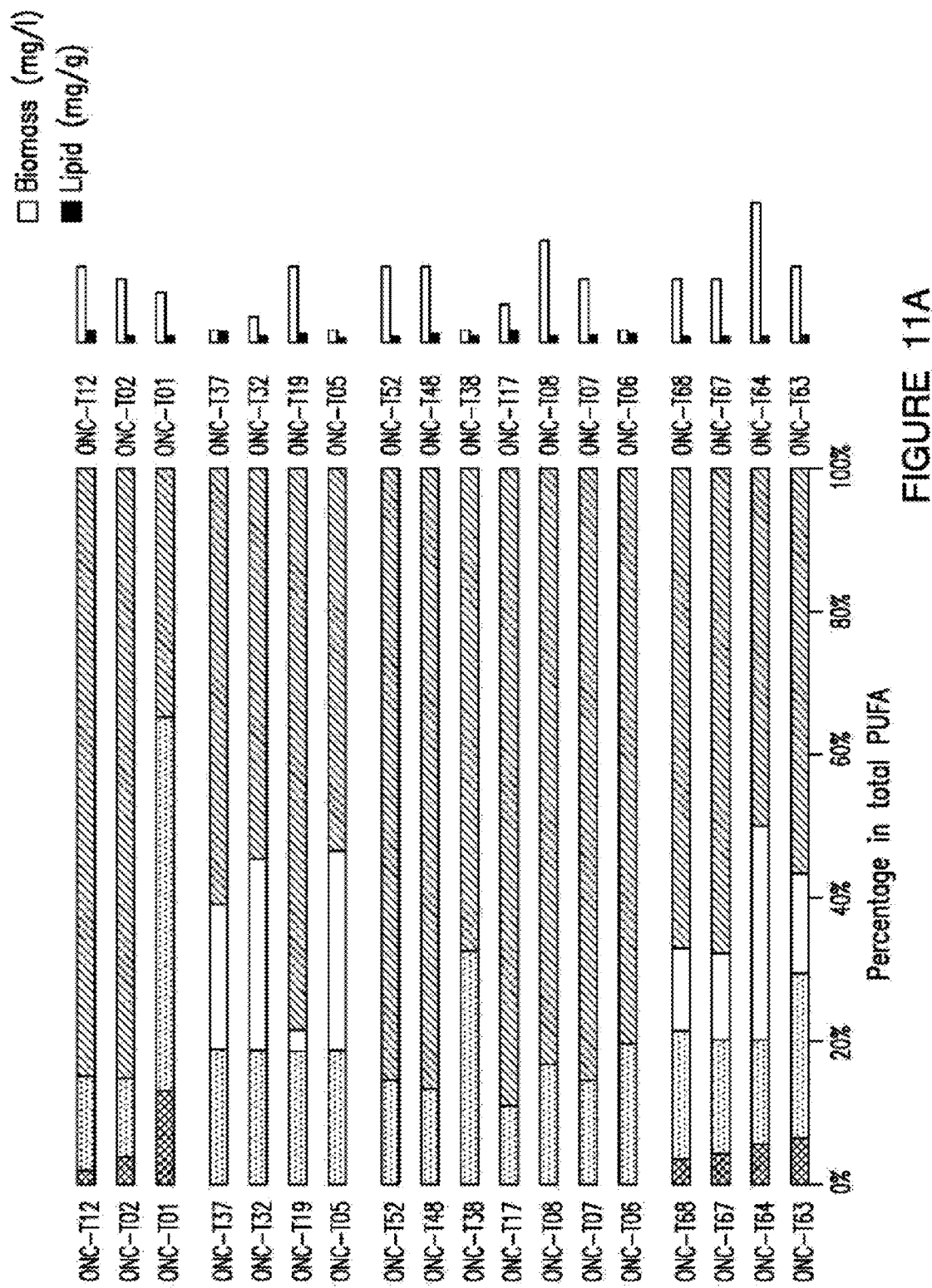
Figure 11B:
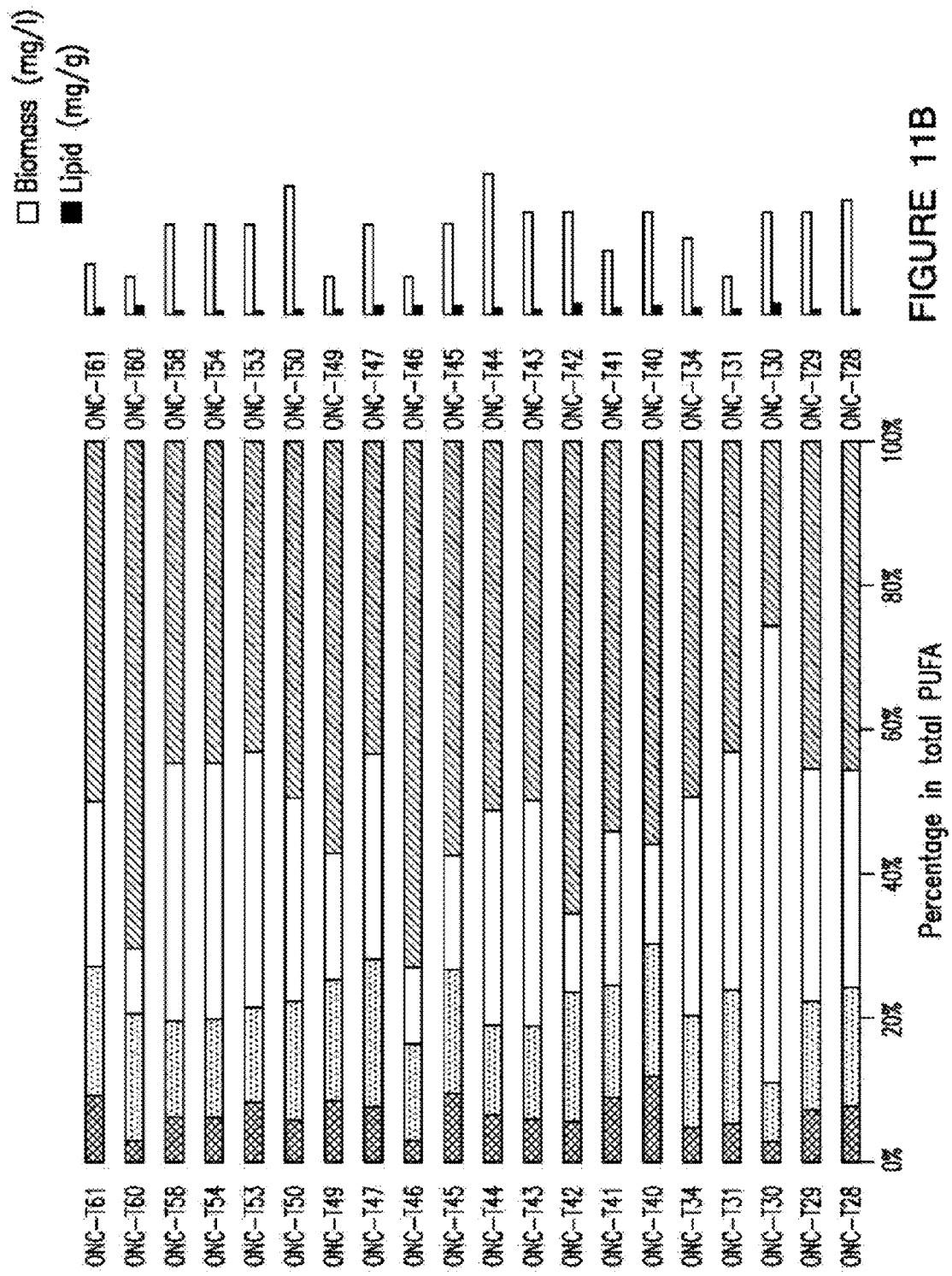
Figure 11C:
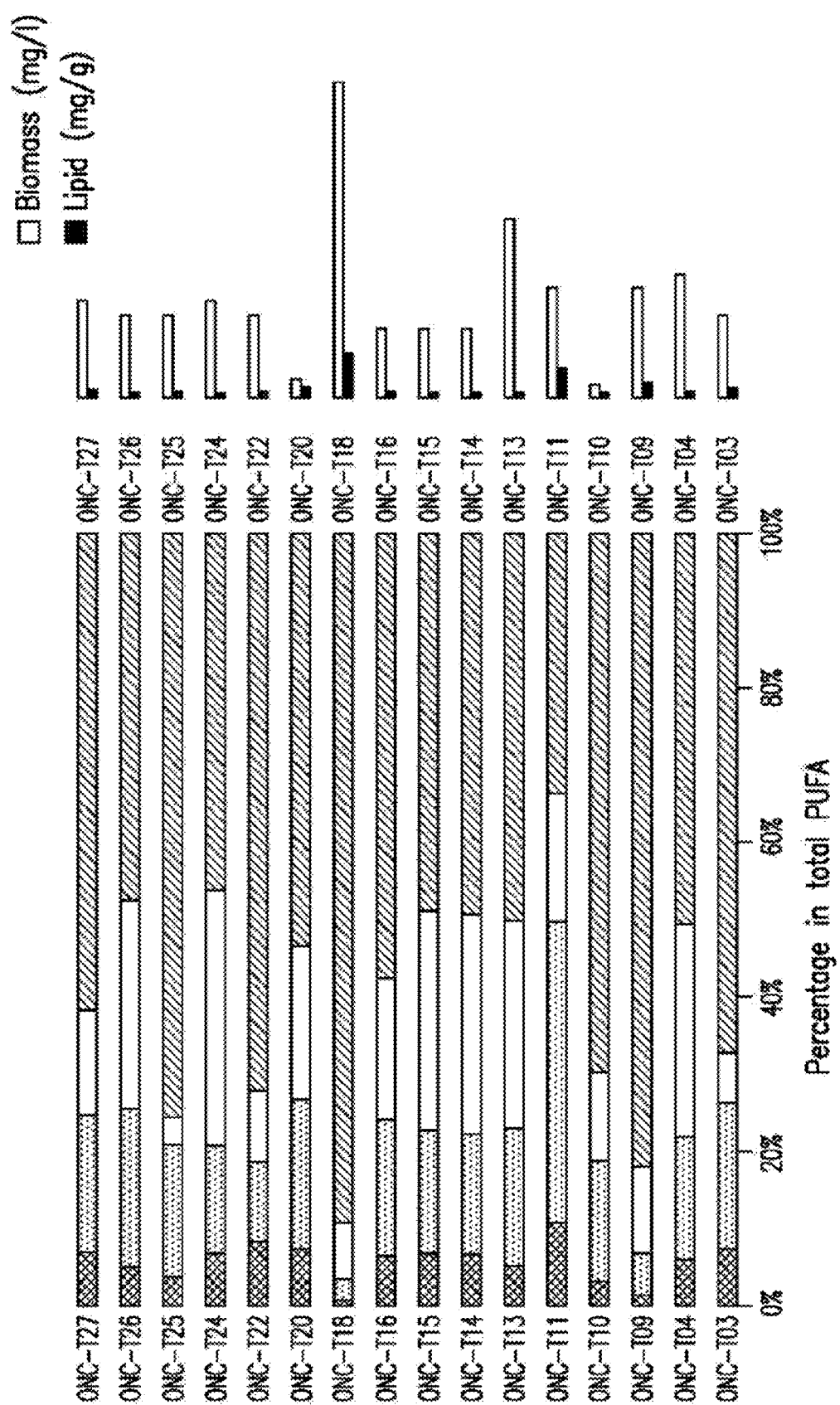
Figure 11D:
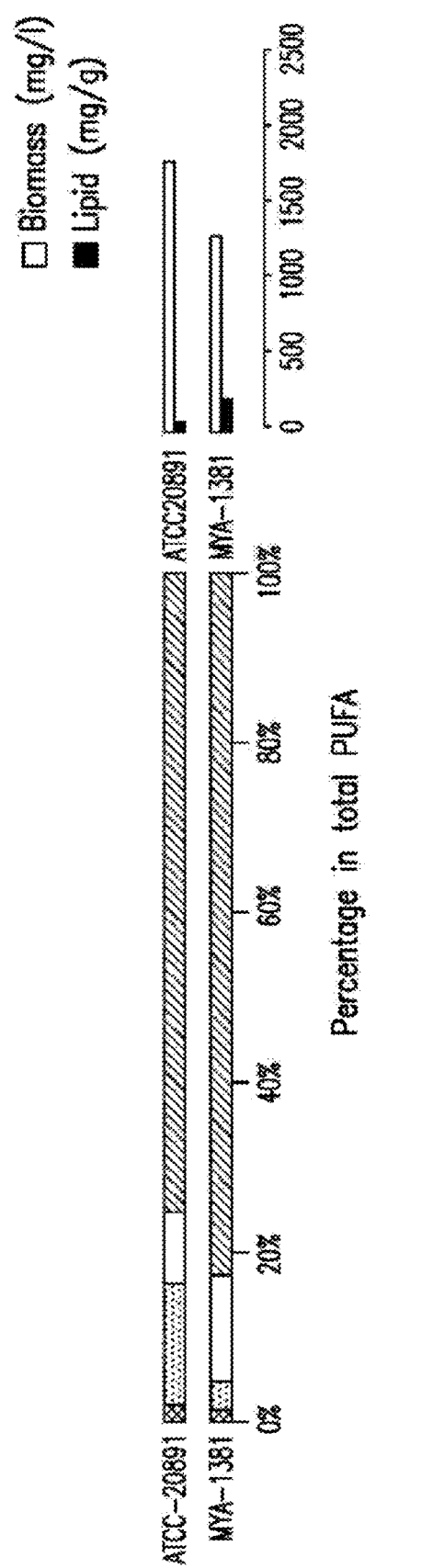

The heterotrophic medium can comprise sea salt (artificial or natural), one or more carbon sources, and one or more nitrogen sources. The sea salt can be present in an amount of from about 2.0 to about 40.0 g $L^{-1}$. The concentration of the carbon and nitrogen source used under standard cultivation conditions (not for high-concentration, but rather cost efficient fermentation) falls within the range of 5 g $L^{-1}$ to 60 g $L^{-1}$ and 4 g $L^{-1}$ to 10 g $L^{-1}$, respectively. For high-concentration fermentation, the concentration of the carbon and nitrogen source used under standard cultivation conditions falls within the range of 100 g $L^{-1}$ and 160 g $L^{-1}$ and 40 g $L^{-1}$ to 60 g $L^{-1}$, respectively. The trend being that for oil accumulation, the eukaryotic microorganism is grown in a culture medium (as those described above) in which the supply of nitrogen is limited after about 24 to about 48 hours, while the supply of carbon remains in abundance. This eukaryotic microorganism continues to assimilate the carbon (in the form of simple sugars) but can no longer undergo cell division due to a lack of nitrogen for the generation of relevant proteins and nucleic acids. The result being that these sugars are converted into storage oils, much in the same way that Ratledge C. (Lipid Tech. 16:34-39, 2004) describes and FIG. 9 depicts this phenomenon specific for this organism.

The nitrogen source can be one or more of peptone, yeast extract, malt extract, and sodium glutamate. The nitrogen source can also be corn steep liquor or cotton seed extract. The nitrogen source can comprise yeast extract and/or peptone or monosodium glutamate. For example, the nitrogen source can include, but is not limited to EMD™ YE-MSG, EMD™ YE, EMD™ Peptone-MSG, Sigma™ YE-MSG, Sigma™ YE, Fermtech™ YE-MSG, Fermtech™ YE, or Fish meal (62% protein). The yeast extract can be present in an amount of about 2 g $L^{-1}$. The monosodium glutamate can be present in an amount of about 8 g $L^{-1}$.

The carbon source can be one or more of D-trehalose, glycerol, D-gluconic acid, L lactic acid, D,L-malic acid, D-ribose, Tween 20, D-fructose, acetate, acetic acid, alpha-D-glucose, maltose, thymidine, L-asparagine, D-xylose, Tween 40, a-keto-glutaric acid, sucrose, L-glutamine, Tween 80, beta-methyl-D-glucoside, maltotriose, adenosinine, fumaric acid, bromo succinic acid, L-serine, D-cellobiose, L-alanyl-glycine, methyl pyruvate, L-malic acid, glycyl-L proline, D-palcose, L-lyxose, pyruvic acid, alpha-D-lactose, dextrin, D-arabinose, 2-deoxy-D ribose, gelatin, dextrose, starch, 3-O-beta-D-galactopyranosyl-D-arabinose, D-tagatose, 5-keto-D-gluconic acid, oxalomalic acid, sorbic acid, L-ornithine, and dihydroxy acetate. In one aspect, the carbon source can be D,L-malic acid, D-fructose, D-xylose, fumaric acid, D-cellobiose, 5-keto-D-gluconic acid, pyruvic acid, alpha-D-lactose, corn dextrin, gelatin, corn starch or wheat starch. The carbon source can be present in an amount of from about 1 g $L^{-1}$ to about 60 g $L^{-1}$ and up to about 200 g $L^{-1}$.

In one example, the medium can comprise about 5 g D-glucose, about 2 g peptone, and about 2 g yeast extract per liter of salt water (natural or artificial). In another, the medium can comprise about 60 g D-glucose, about 10 g yeast extract per liter of salt water (natural or artificial). In another, the medium can comprise about 8 g yeast extract, 32 g MSG, 24 g sea salt (natural and artificial) and 300 g D-glucose per liter.

The medium can further comprise phosphates (e.g., potassium phosphate and sodium phosphates). The medium can further comprise inorganic salts (e.g., ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride). The medium can further comprise a chelating compound (e.g., EDTA). The medium can further comprise vitamins (e.g., pyridoxine hydrochloride, thiamin hydrochloride, calcium pantothenate, p-aminobenzoic acid, riboflavin, nicotinic acid, biotin, folic acid, and vitamin $B_{12}$). The medium can be at a pH of from about 4.0 to about 6.5.

Incubation can be from about 1 to about 9 days (e.g., from about 3 to about 5 days). Incubation can be at from about 18 to about 30° C. (e.g., from about 18-25° C.). Incubation can further comprise shaking or aeration.

Isolating the lipid can comprise contacting the microorganisms with an extraction solvent. The solvent can comprise one or more solvents chosen from chloroform, hexane, methanol, or ethanol, or supercritical $CO_2$.

The method can produce any of the compositions as disclosed above.

The eukaryotic microorganism can produce a lipid composition comprising n-3 DHA at greater than or equal to about 20 g $L^{-1}$ of medium. The eukaryotic microorganism can produce a lipid composition comprising n-3 DHA at greater than or equal to about 40 g $L^{-1}$ of medium. The eukaryotic microorganism can produce a lipid composition comprising n-3 DHA at greater than or equal to about 80 g $L^{-1}$ of medium.

2. Screening and Identification Methods

The eukaryotic microorganism as disclosed herein can produce a lipid containing the (n-3) series of docosahexaenoic acid and eicosapentaenoic acid and the (n-6) series of DPA. These eukaryotic microorganism can be selected, for example, with the following screening method. Vegetative samples can be (and were) placed in 20 mL vials containing 10 mL of sterile 0.2 μm filtered natural seawater containing penicillin and streptomycin at 300 and 500 mg $L^{-1}$, respectively. The vials were then baited with sterile pollen grains and incubated for 48 hours at 18 to 25° C. The pollen grains were then transferred onto agar plates containing antibiotics (as above) and incubated under the same conditions. Single, irregular, hyaline colonies made up of spherical or limaciform cells and atypical of either yeast or bacterial colonies were picked and sub-cultured on the same medium and under the same conditions as above. These isolates were then screened for growth and fatty acids using a nutrient liquid medium, prepared with 0.2 μm filtered natural seawater containing 5 g $L^{-1}$ glucose, 2 g $L^{-1}$ peptone and 2 g $L^{-1}$ yeast extract, with the resulting cellular biomass collected by centrifugation or sedimentation within a liquid medium. Fatty acids were directly transesterified using conventional methods, with the fatty acid methyl ester composition analyzed via gas chromatography, with strains that produce appropriate amounts of the n-3 series of DHA and the n-6 series of DPA selected for further work.

Disclosed are methods of identifying an eukaryotic microorganism, the method comprising: baiting a vegetative sample in salt water (natural sea or artificial) with pollen grains and incubating; transferring the grains to a heterotrophic medium and incubating; and identifying isolates that produce fatty acids.

Also disclosed are lipid compositions produced by the above identified eukaryotic microorganisms.

Also disclosed are lipid compositions produced by methods using the disclosed eukaryotic microorganisms and the methods disclosed herein.

Also disclosed are eukaryotic microorganisms (ONC-T18) having American Type Culture Collection accession number PTA-6245.

Also disclosed are eukaryotic microorganisms belonging to the order Thraustochytriales (ONC-T18) having 18S rRNA, such as SEQ ID 1, and identified as a *Thraustochytrium* sp.

Also disclosed is a eukaryotic microorganism, *Thraustochytrium* sp. capable of producing DHA and DPA in concentrations in excess of 400 mg $L^{-1}$ and 100 mg $L^{-1}$, respectively.

Also disclosed is a eukaryotic microorganism, *Thraustochytrium* sp. capable of producing carotenoids via heterotrophic fermentation as mentioned above in the range 50 to 1250 mg $kg^{-1}$ and astaxanthin, zeaxanthin, canthaxanthin, echinenine and beta-carotene in the range of 1 to 20 mg $kg^{-1}$, 0.25 to 10 mg $kg^{-1}$, 1 to 20 mg $kg^{-1}$ 1 to 20 mg $kg^{-1}$ and 1 to 200 mg $kg^{-1}$, respectively.

Also disclosed are processes for growing a eukaryotic microorganism comprising, culturing the eukaryotic microorganism under conditions, wherein the conditions comprise a medium comprising sodium chloride in the form of artificial sea salt (trophic marine) between 2.0 and 15.0 g $L^{-1}$; a nitrogen source in the form of yeast extract and monosodium glutamate at 2.0 and 8.0 g $L^{-1}$ respectively; and carbon in the form of glucose up to 130 g $L^{-1}$.

The disclosed processes can, for example, grow ONC-T18, whereby at least 24% weight is DHA, at least 6% by weight is DPA and at least 1% is EPA of total fatty acid.

The disclosed processes for growth can also, for example, grow ONC-T18 such that at least 1% by weight is carotenoid material, with from 1 to 2% and at least 1.2% of that being astaxanthin, with from 0.25 and 1% and at least 0.45% being zeaxanthin, with from 5 to 16% and at least 9% being canthaxanthin, with from 1 to 2% and at least 1.2% of that being echinenone and from 12 to 16% and at least 14% by weight being beta-carotene.

3. Nucleic Acids

There are a variety of molecules disclosed herein that are nucleic acid based, including for example the nucleic acids that encode, for example, rRNA, as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U/T. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA*, 86:6553-6556, 1989), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, SEQ ID NO:1, as well as any other nucleic acids and proteins disclosed herein that can be disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain aspects the primers may be used as species or genus specific probes for the *Thraustochytrium* or *Bacillus* mentioned here. In this instance, primers would be designed to be specific to the eukaryotic microorganism, with PCR reactions subsequently carried out. Presence of target species would then be determined by successful PCR product formation. In certain aspects the primers can also be used for DNA amplification reactions, such as PCR or direct sequencing. It is understood that in certain aspects the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

It is understood that there are a variety of transcription control systems that can be used in the organisms disclosed herein, in addition to the general systems discussed below. It is understood that the organisms disclosed herein can be transfected and transformed with a variety of genes, such as marker genes, as discussed herein, or genes which have other desirable attributes, such as enhanced or unique growth characteristics.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273:113, 1978). The immediate early promoter of the human cytomegalovirus is conveniently obtained as a HindIII E restriction fragment (Greenway, P. J. et al., *Gene* 18:355-360, 1982). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78:993, 1981) or 3' (Lusky, M. L., et al., *Mol. Cell. Bio.* 3:1108, 1983) to the transcription unit. Furthermore, enhancers can be within an intron (Banerji, J. L. et al., *Cell* 33:729, 1983) as well as within the coding sequence itself (Osborne, T. F., et al., *Mol. Cell. Bio.* 4:1293, 1984). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, alpha-fetoprotein and insulin), typically one will use an enhancer from a eukaryotic cell virus for general expression. Preferred examples are the SV40 enhancer on the late side of the replication origin (100-270 bp), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bp). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1:327, 1982), mycophenolic acid, (Mulligan, R. C. and Berg, P. *Science* 209: 1422, 1980) or hygromycin, (Sugden, B. et al., *Mol. Cell. Biol.* 5:410-413, 1985). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Peptides a) Protein Variants

As discussed herein there are numerous variants of the disclosed organism proteins that are known and herein contemplated. In addition, to the known functional Thraustochytriales strain there are derivatives of the Thraustochytriales proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

TABLE 1

Amino Acid Abbreviations

| Amino Acid | Abbreviations | |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

Amino Acid Substitutions

| Original Residue | Exemplary Conservative Substitutions* |
|---|---|
| Ala | Ser |
| Arg | Lys; Gln |
| Asn | Gln; His |
| Asp | Glu |
| Cys | Ser |
| Gln | Asn; Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

*Others are known in the art

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86, 1983), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of proteins herein disclosed which have at least, 60%, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482, 1981, by the homology alignment algorithm of Needleman and Wunsch, *J. Mol. Biol.* 48: 443, 1970, by the search for similarity method of Pearson and Lipman, *Proc. Natl. Acad. Sci. USA* 85: 2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular strain from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Mol. Biol.* 77:43-73, 1991, Zoller, *Curr. Opin. Biotech.*, 3:348-354, 1992; Ibba, *Biotechnol. Genet. Eng.* 13:197-216, 1995, Cahill et al., *Trends Biochem. Sci.*, 14:400-403, 1989; Benner, *Trends. Biotechnol.*, 12:158-163, 1994) all of which are herein incorporated by reference at least for material related to amino acid analogs).

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —$CH=CH$—(cis and trans), —$COCH_2$—, —$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267, 1983; Spatola, A. F., Vega Data (March 1983), Vol. 1, Issue 3, Peptide Backbone Modifications (general review); Morley, *Trends Pharm. Sci.* 463-468, 1980; Hudson, D. et al., *Int. J. Pept. Prot. Res.* 14:177-185, 1979 (—$CH_2NH$—, $CH_2CH_2$—); Spatola et al. *Life Sci.* 38:1243-1249, 1986 (—$CHH_2$—S); Hann J. Chem. *Soc. Perkin Trans.* 1307-314, 1982 (—CH—CH—, cis and trans); Almquist et al. *J. Med. Chem.* 23:1392-1398, 1980 (—$COCH_2$—); Jennings-White et al. *Tetrahedron Lett.*, 23:2533, 1982 (—$COCH_2$—); Szelke et al. *European Appln., EP* 45665 CA: 97:39405, 1982 (—$CH(OH)CH_2$—); Holladay et al. *Tetrahedron Lett.* 24:4401-4404, 1983 (—C(OH)$CH_2$—); and Hruby *Life Sci.* 31:189-199, 1982 (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387, 1992, incorporated herein by reference).

6. Supplements

Also disclosed herein are nutritional supplements. A nutritional supplement is any compound or composition that can be administered to or taken by a subject to provide, supply, or increase a nutrient(s) (e.g., vitamin, mineral, essential trace element, amino acid, peptide, nucleic acid, oligonucleotide, lipid, cholesterol, steroid, carbohydrate, and the like). In one aspect, disclosed herein are nutritional supplements comprising any of the compounds disclosed herein. For example, a nutritional supplement can comprise any of the lipids disclosed herein. The fatty acid residues of these lipids can be any fatty acid as disclosed herein (e.g., unsaturated or saturated fatty acid residues).

The nutritional supplement can comprise any amount of the compounds disclosed herein, but will typically contain an amount determined to supply a subject with a desired dose of a benzenediol derivative (e.g., $CoQ_{10}$) and/or fatty acids. The exact amount of compound required in the nutritional supplement will vary from subject to subject, depending on the species, age, weight and general condition of the subject, the severity of the dietary deficiency being treated, the particular mode of administration, and the like. Thus, it is not possible to specify an exact amount for every nutritional supplement. However, an appropriate amount can be determined by one of ordinary skill in the art using only routine experimentation given the teachings herein. In one specific example, a nutritional supplement can comprise from about 0.05 to about 20%, from about 1 to about 7.5%, or from about 3 to about 5% by weight of the compound. In another example, the nutritional supplement can comprise from about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0% by weight of the compound, where any of the stated values can form an upper or lower endpoint when appropriate. In another aspect, when the nutritional supplement, the supplement can be composed of up to 100% of the supplement.

The nutritional supplement can also comprise other nutrient(s) such as vitamins trace elements, minerals, and the like. Further, the nutritional supplement can comprise other components such as preservatives, antimicrobials, anti-oxidants, chelating agents, thickeners, flavorings, diluents, emulsifiers, dispersing aids, and/or binders.

The nutritional supplements are generally taken orally and can be in any form suitable for oral administration. For example, a nutritional supplement can typically be in a tablet, gel-cap, capsule, liquid, sachets, or syrup form.

7. Delivery Devices

Any of the compounds described herein can be incorporated into a delivery device. Examples of delivery devices include, but are not limited to, microcapsules, microspheres, nanospheres or nanoparticles, liposomes, noisome, nanoerythrosome, solid-liquid nanoparticles, gels, gel capsules, tablets, lotions, creams, sprays, or emulsions. Other examples of delivery devices that are suitable for non-oral administration include pulmospheres. Examples of particular delivery devices useful herein are described below.

The disclosed compounds can be incorporated into liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The disclosed compositions in liposome form can contain, in addition to a compound disclosed herein, stabilizers, preservatives, excipients, and the like. Examples of suitable lipids are the phospholipids and the phosphatidylcholines (lecithins), both natural and synthetic. Methods of forming liposomes are known in the art. See, e.g., Prescott, Ed., *Methods in Cell Biology*, Volume XIV, Academic Press, New York, p. 33 et seq., 1976, which is hereby incorporated by reference herein for its teachings of liposomes and their preparation.

In other examples, the liposomes can be cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see e.g., Brigham, et al., *Am J Resp Cell Mol Biol* 1:95-100, 1989; Felgner, et al., *Proc Natl Acad Sci USA* 84:7413-7, 1987; and U.S. Pat. No. 4,897,355, which are incorporated by reference herein for their teachings of liposomes. As one example, delivery can be via a liposome using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

As described herein, noisomes are delivery devices that can be used to deliver the compositions disclosed herein. Noisomes are multilamellar or unilamellar vesicles involving non-ionic surfactants. An aqueous solution of solute is enclosed by a bilayer resulting from the organization of surfactant macromolecules. Similar to liposomes, noisomes are used in targeted delivery of, for example, anticancer drugs, including methotrexate, doxorubicin, and immunoadjuvants. They are generally understood to be different from transferosomes, vesicles prepared from amphiphilic carbohydrate and amino group containing polymers, e.g., chitosan.

As described herein, nanoerythrosomes are delivery devices that can be used to deliver the compositions disclosed herein. Nanoerythrosomes are nano-vesicles made of red blood cells via dialysis through filters of defined pore size. These vesicles can be loaded with a diverse array of biologically active molecules, including proteins and the compositions disclosed herein. They generally serve as ideal carriers for antineoplastic agents like bleomycin, actinomycin D, but can be used for steroids, other lipids, etc.

Artificial red blood cells, as described herein, are further delivery devices that can be used to deliver the compositions disclosed herein. Artificial red blood cells can be generated by interfacial polymerization and complex emulsion methods. Generally, the "cell" wall is made of polyphtaloyl L-lysine polymer/polystyrene and the core is made of a hemoglobin solution from sheep hemolysate. Hemoglobin loaded microspheres typically have particle sizes of from about 1 to about 10 mm. Their size, flexibility, and oxygen carrying capacity is similar to red blood cells.

Solid-lipid nanoparticles, as described herein, are other delivery devices that can be used to deliver the compositions disclosed herein. Solid-lipid nanoparticles are nanoparticles, which are dispersed in an aqueous surfactant solution. They are comprised of a solid hydrophobic core having a monolayer of a phospholipid coating and are usually prepared by high-pressure homogenization techniques. Immunomodulating complexes (ISCOMS) are examples of solid-lipid nanoparticles. They are cage-like 40 nm supramolecular assemblies comprising of phospholipid, cholesterol, and hydrophobic antigens and are used mostly as immunoadjuvants. For instance, ISCOMs are used to prolong blood-plasma levels of subcutaneously injected cyclosporine.

Microspheres and micro-capsules, as described herein, are yet other delivery devices that can be used to deliver the compositions disclosed herein. In contrast to liposomal delivery systems, microspheres and micro-capsules typically do not have an aqueous core but a solid polymer matrix or membrane. These delivery devices are obtained by controlled precipitation of polymers, chemical cross-linking of soluble polymers, and interfacial polymerization of two monomers or high-pressure homogenization techniques. The encapsulated compound is gradually released from the depot by erosion or diffusion from the particles. Successful formulations of short acting peptides, such as LHRH agonists like leuprorelin and triptoreline, have been developed. Poly (lactide co-glycolide (PLGA) microspheres are currently used as monthly and three monthly dosage forms in the treatment of advanced prostrate cancer, endometriosis, and other hormone responsive conditions. Leuprolide, an LHRH superagonist, was incorporated into a variety of PLGA matrices using a solvent extraction/evaporation method. As noted, all of these delivery devices can be used in the methods disclosed herein.

Pulmospheres are still other examples of delivery devices that can be used herein. Pulmospheres are hollow porous particles with a low density (less than about 0.1 m mL$^{-1}$). Pulmospheres typically have excellent re-dispersibility and are usually prepared by supercritical fluid condensation technology. Co-spray-drying with certain matrices, such as carbohydrates, human serum albumin, etc., can improve the stability of proteins and peptides (e.g., insulin) and other biomolecules for pulmonary delivery. This type of delivery could be also accomplished with micro-emulsions and lipid emulsions, which are ultra fine, thin, transparent oil-in-water (o/w) emulsions formed spontaneously with no significant input of mechanical energy. In this technique, an emulsion can be prepared at a temperature, which must be higher than the phase inversion temperature of the system. At elevated temperature the emulsion is of water-in-oil (w/o) type and as it cools at the phase inversion temperature, this emulsion is inverted to become o/w. Due to their very small inner phase, they are extremely stable and used for sustained release of steroids and vaccines. Lipid emulsions comprise a neutral lipid core (i.e., triglycerides) stabilized by a monolayer of amphiphilic lipid (i.e., phospholipid) using surfactants like egg lecithin triglycerides and miglyol. They are suitable for passive and active targeting.

There are other oral delivery systems under investigation that are based on osmotic pressure modulation, pH modulation, swelling modulation, altered density and floating systems, mucoadhesiveness etc. These formulations and time-delayed formulations to deliver drugs in accordance with circadian rhythm of disease that are currently in use or investigation can be applied for delivery of the compositions disclosed herein.

In one particular aspect disclosed herein, the disclosed compounds, including nutritional supplement and pharmaceutical formulations thereof, can be incorporated into microcapsules as described herein.

In one aspect disclosed herein, the disclosed compounds can be incorporated into microcapsules. In one aspect, the microcapsule comprises an agglomeration of primary microcapsules and the chromium compounds described herein, each individual primary microcapsule having a primary shell, wherein the chromium compound is encapsulated by the primary shell, wherein the agglomeration is encapsulated by an outer shell. These microcapsules are referred to herein as "multicore microcapsules."

In another aspect, described herein are microcapsules comprising a chromium compound, a primary shell, and a secondary shell, wherein the primary shell encapsulates the chromium compound, and the secondary shell encapsulates the loading substance and primary shell. These microcapsules are referred to herein as "single-core microcapsules."

Optionally, other loading substances can be encapsulated with the chromium compound. The loading substance can be any substance that is not entirely soluble in the aqueous mixture. In one aspect, the loading substance is a solid, a hydrophobic liquid, or a mixture of a solid and a hydrophobic liquid. In another aspect, the loading substance comprises a grease, an oil, a lipid, a drug (e.g., small molecule), a biologically active substance, a nutritional supplement (e.g., vitamins), a flavor compound, or a mixture thereof. Examples of oils include, but are not limited to, animal oils (e.g., fish oil, marine mammal oil, etc.), vegetable oils (e.g., canola or rapeseed), mineral oils, derivatives thereof or mixtures thereof. The loading substance can be a purified or partially purified oily substance such as a fatty acid, a triglyceride or ester thereof, or a mixture thereof. In another aspect, the loading substance can be a carotenoid (e.g., lycopene), a satiety agent, a flavor compound, a drug (e.g., a water insoluble drug), a particulate, an agricultural chemical (e.g., herbicides, insecticides, fertilizers), or an aquaculture ingredient (e.g., feed, pigment).

In one aspect, the loading substance can be an omega-3 fatty acid. Examples of omega-3 fatty acids include, but are not limited to, a-linolenic acid (18:3n3), octadecatetraenoic acid (18:4n3), eicosapentaenoic acid (20:5n3) (EPA), docosahexaenoic acid (22:6n3) (DHA), docosapentaenoic acid (22:5n3) (DPA), eicosatetraenoic acid (20:4n3), uncosapentaenoic acid (21:5n3), docosapentaenoic acid (22:5n3) and derivatives thereof and mixtures thereof. Many types of derivatives of omega-3 fatty acids are well known in the art. Examples of suitable derivatives include, but are not limited to, esters, such as phytosterol esters, branched or unbranched $C_1$-$C_{30}$ alkyl esters, branched or unbranched $C_2$-$C_{30}$ alkenyl esters, or branched or unbranched $C_3$-$C_{30}$ cycloalkyl esters such as phytosterol esters and $C_1$-$C_6$ alkyl esters. Sources of oils can be derived from aquatic organisms (e.g., anchovies, capelin, Atlantic cod, Atlantic herring, Atlantic mackerel, Atlantic menhaden, salmonids, sardines, shark, tuna, etc) and plants (e.g., flax, vegetables, etc) and microorganisms (e.g., fungi and algae).

In one aspect, the loading substance can contain an antioxidant. Examples of antioxidants include, but are not limited to, vitamin E, $CoQ_{10}$, tocopherols, lipid soluble derivatives of more polar antioxidants such as ascorbyl fatty acid esters (e.g., ascorbyl palmitate), plant extracts (e.g., rosemary, sage and oregano oils), algal extracts, and synthetic antioxidants (e.g., BHT, TBHQ, ethoxyquin, alkyl gallates, hydroquinones, tocotrienols).

A number of different polymers can be used to produce the shell layers of the single and multicore microcapsules. Examples of such polymers include, but are not limited to, a protein, a polyphosphate, a polysaccharide, or a mixture thereof. In another aspect, the shell material used to prepare the single- and multicore microcapsules further comprises In another aspect, the shell material used to prepare the single- and multicore microcapsules further comprises gelatin type A, gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, chitin, polylactides, poly-lactide-co-glycolides, derivatized chitin, chitosan, poly-lysine, various inorganic-organic composites, or any mixture thereof. It is also contemplated that derivatives of these polymers can be used as well. In another aspect, the polymer can be kosher gelatin, non-kosher gelatin, Halal gelatin, or non-Halal gelatin.

In one aspect, one or more of the shell layers in the single and multicore microcapsules comprises gelatin having a Bloom number less than 50. This gelatin is referred to herein as "low Bloom gelatin." The Bloom number describes the gel strength formed at 10° C. with a 6.67% solution gelled for 18 hours. In one aspect, the low Bloom gelatin has a Bloom number less than 40, less than 30, less than 20, or less than 10. In another aspect, the gelatin has a Bloom number of 45, 40, 35, 30, 25, 20, 15, 10, 9, 8, 7, 6, 5, 4, 3, 2, 1, or 0, where any two values can be used to produce a range. In another aspect, the low Bloom gelatin is in both the primary shell and the outer shell of the multicore microcapsule. In one aspect, the low Bloom gelatin is gelatin type A. In another aspect, the low Bloom gelatin is gelatin type A produced by Kenney & Ross Ltd., R.R. #3 Shelburne, NS Canada. In another aspect, gelatin having a Bloom number of zero is in both the primary shell and the outer shell of the multicore microcapsule.

In one aspect, the material used to make the shells of the single- or multicore microcapsules is a two-component system made from a mixture of two different types of polymers. In one aspect, the material is a complex coacervate between the polymer components. Complex coacervation is caused by the interaction between two oppositely charged polymers. In one aspect, the shell material used to produce the single and multicore microcapsules is composed of (1) low Bloom gelatin and (2) gelatin type B, polyphosphate, gum arabic, alginate, chitosan, carrageenan, pectin, carboxymethylcellulose, whey protein, soy protein, canola protein, albumin, or a mixture thereof. The molar ratio of the different polymers can vary. For example, the molar ratio of low Bloom gelatin to the other polymer component is from 1:5 to 15:1. For example, when low Bloom gelatin and polyphosphate are used, the molar ratio of low Bloom gelatin to polyphosphate is about 8:1 to about 12:1; when low Bloom gelatin and gelatin type B are used, the molar ratio is 2:1 to 1:2; and when low Bloom gelatin and alginate are used, the molar ratio is 3:1 to 8:1.

Processing aids can be included in the shell material (e.g., primary or outer shells). Processing aids can be used for a variety of reasons. For example, they may be used to promote agglomeration of the primary microcapsules, stabilize the emulsion system, improve the properties of the outer shells, control microcapsule size and/or to act as an antioxidant. In one aspect, the processing aid can be an emulsifier, a fatty acid, a lipid, a wax, a microbial cell (e.g., yeast cell lines), a clay, or an inorganic compound (e.g., calcium carbonate). Not wishing to be bound by theory, these processing aids can improve the barrier properties of the microcapsules. In one aspect, one or more antioxidants can be added to the shell material. Antioxidant properties are useful both during the process (e.g. during coacervation and/or spray drying) and in the microcapsules after they are formed (i.e. to extend shelf-life, etc). Preferably a small number of processing aids that perform a large number of functions can be used. In one aspect, the antioxidant can be a phenolic compound, a plant extract, or a sulphur-containing amino acid. In one aspect, ascorbic acid (or a salt thereof such as sodium or potassium ascorbate) can be used to promote agglomeration of the primary microcapsules, to control microcapsule size and to act as an antioxidant. The antioxidant can be used in an amount of about 100 ppm to about 12,000 ppm, or from about 1,000 ppm to about 5,000 ppm. Other processing aids such as, for example, metal chelators, can be used as well. For example, ethylene diamine tetraacetic acid can be used to bind metal ions, which can reduce the catalytic oxidation of the loading substance.

In one aspect, the primary microcapsules (primary shells) have an average diameter of about 40 nm to about 10 μm, 0.1 μm to about 10 μm, 1 μm to about 10 μm, 1 μm to about 8 μm, 1 μm to about 6 μm, 1 μm to about 4 μm, or 1 μm to about 2 μm, or 1 μm. In another aspect, the multicore microcapsules can have an average diameter of from about 1 μm to about 2000 μm, 20 μm to about 1000 μm, from about 20 μm to about 100 μm, or from about 30 μm to about 80 μm. In another aspect, the single-core microcapsules have an outer diameter of from 1 μm to 2,000 μm.

The microcapsules described herein generally have a combination of high payload and structural strength. For example, payloads of loading substance can be from 20% to 90%, 50% to 70% by weight, or 60% by weight of the single or multicore microcapsules.

In one aspect, the methods disclosed in U.S. Patent Application Publication No. 2003/0193102, which is incorporated by reference in its entirety, can be used to encapsulate the chromium compounds described herein. It is also contemplated that one or more additional shell layers can be placed on the outer shell of the single or multicore microcapsules. In one aspect, the techniques described in International Publication No. WO 2004/041251 A1, which is incorporated by reference in its entirety, can be used to add additional shell layers to the single and multicore microcapsules.

a) Pharmaceutical and Nutraceutical Compositions

These lipids and antioxidants are targeted for use in animal feeds, pharmaceuticals, nutraceuticals (especially infant formula) as well as in the industry. This is to also include nutraceutical forms of delivery such as gel capsules and the like, common microencapsulations, etc.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parental administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, 1991; Bagshawe, K. D., *Br. J. Cancer*, 60:275-281, 1989; Bagshawe, et al., *Br. J. Cancer*, 58:700-703, 1988; Senter, et al., *Bioconjugate Chem.*, 4:3-9, 1993; Battelli, et al., *Cancer Immunol. Immunother.*, 35:421-425, 1992; Pietersz and McKenzie, *Immunolog. Reviews*, 129:57-80, 1992; and Roffler, et al., *Biochem. Pharmacol.*, 42:2062-2065, 1991). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glicoma cells in vivo. The following references are examples of the use of this technology to target specific proteins to tumor tissue (Hughes et al., *Cancer Research*, 49:6214-6220, 1989); and Litzinger and Huang, *Biochimica et Biophysica Acta*, 1104:179-187, 1992). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:399-409, 1991).

(1) Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

b) Targeted Delivery

The disclosed liposomes and microcapsules can be targeted to a particular cell type, such as islets cells, via antibodies, receptors, or receptor ligands. The following references are examples of the use of this technology to target specific tissue (Senter, et al., *Bioconjugate Chem* 2:447-51, 1991; Bagshawe, *Br J Cancer* 60:275-81, 1989; Bagshawe, et al., *Br J Cancer* 58:700-3, 1988; Senter, et al., *Bioconjugate Chem* 4:3-9, 1993; Battelli, et al., *Cancer Immunol Immunother* 35:421-5, 1992; Pietersz and McKenzie, *Immunolog Reviews* 129:57-80, 1992; and Roffler, et al., *Biochem Pharmacol* 42:2062-5, 1991). These techniques can be used for a variety of other specific cell types.

8. Foodstuffs

Also disclosed herein are foodstuffs comprising any of the microcapsules and emulsions disclosed herein. By "foodstuff" is meant any article that can be consumed (e.g., eaten, drank, or ingested) by a subject. In one aspect, the microcapsules can be used as nutritional supplements to a foodstuff. For example, the microcapsules and emulsions can be loaded with vitamins, omega-3 fatty acids, and other compounds that provide health benefits. In one aspect, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In another aspect, the foodstuff is bread, tortillas, cereal, sausage, chicken, ice cream, yogurt, milk, salad dressing, rice bran, fruit juice, a dry beverage powder, rolls, cookies, crackers, snack food, fruit pies, or cakes.

9. Chips and Microarrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

10. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

11. Kits

Disclosed herein are kits that are drawn to reagents that can be used in practicing the methods disclosed herein or in using or keeping the compositions disclosed herein. The kits can include any reagent or combination of reagent discussed herein or that would be understood to be required or beneficial in the practice of the disclosed methods. For example, the kits could include one or more of the eukaryotic microorganisms disclosed herein along with, for example, media for their maintenance. The kits could also include, for example, the lipids or antioxidants, along with means for using or administering these.

12. Compositions with Similar Functions

It is understood that the compositions disclosed herein have certain functions, such as producing certain ratios of lipids. Disclosed herein are certain structural, genetic, and functional requirements for performing the disclosed functions, and it is understood that there are a variety of structures, genetic backgrounds, and functional backgrounds which can perform the same function which are related to the disclosed structures, and that these structures will ultimately achieve the same result, for example production of a certain ration of lipids.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356, 1984, (phosphotriester and phosphite triester methods), and Narang et al., *Methods Enzymol.*, 65:610-620, 1980, (phosphotriester method). Protein nucleic acid molecules can be made using known methods such as those described by Nielsen et al., *Bioconjug. Chem.* 5:3-7, 1994.

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151, 1991). Alternatively, native chemical ligation of synthetic peptides can be utilized to synthetically construct large peptides or polypeptides from shorter peptide fragments. This method consists of a two step chemical reaction (Dawson et al. *Science*, 266:776-779, 1994). The first step is the chemoselective reaction of an unprotected synthetic peptide— thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. *FEBS Lett.* 307:97-101, 1992; Clark-Lewis I et al., *J. Biol. Chem.*, 269:16075, 1994; Clark-Lewis I et al., *Biochemistry*, 30:3128, 1991; Rajarathnam K et al., *Biochemistry* 33:6623-30, 1994).

Alternatively, unprotected peptide segments are chemically linked where the bond formed between the peptide segments as a result of the chemical ligation is an unnatural (non-peptide) bond (Schnolzer, M et al. *Science*, 256:221, 1992). This technique has been used to synthesize analogs of protein domains as well as large amounts of relatively pure proteins with full biological activity (de Lisle Milton R C et al., Techniques in Protein Chemistry IV. Academic Press, New York, pp. 257-267, 1992).

3. Processes for Making the Compositions

Disclosed are processes for making the compositions as well as making the intermediates leading to the compositions. For example, disclosed are eukaryotic microorganisms which can produce desired lipids and antioxidants as well as methods for isolating and purifying the desired lipids and antioxidants. There are a variety of methods that can be used for making these compositions, such as synthetic chemical methods and standard molecular biology methods. It is understood that the methods of making these and the other disclosed compositions are specifically disclosed.

Disclosed are cells produced by the process of transforming the cell with any nucleic acid. Disclosed are cells produced by the process of transforming the cell with any of the non-naturally occurring disclosed nucleic acids.

Disclosed are any of the lipids produced by the disclosed eukaryotic microorganisms. Disclosed are any peptides produced by the process of expressing the peptide in the disclosed organisms. Methods of using the compositions.

4. Methods of Using the Compositions as Research Tools

The disclosed compositions can be used in a variety of ways as research tools and of the production of, for example, lipids and antioxidants.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any method for determining allelic analysis of for example, the strains of the organisms disclosed herein, particularly allelic analysis as it relates to the production of lipids and antioxidants. The compositions can also be used in any known method of screening assays, related to chip/microarrays. The compositions can also be used in any known way of using the computer readable embodiments of the disclosed compositions, for example, to study relatedness or to perform molecular modeling analysis related to the disclosed compositions.

5. Methods of Gene Modification and Gene Disruption

The disclosed compositions and methods can be used for targeted gene disruption and modification in any animal that can undergo these events. Gene modification and gene disruption refer to the methods, techniques, and compositions that surround the selective removal or alteration of a gene or stretch of chromosome in an organism, such as the eukaryotes disclosed herein, in a way that propagates the modification through the replication of the organism. In general, for example, a cell is transformed with a vector which is designed to homologously recombine with a region of a particular chromosome or nucleic acid contained within the cell, as for example, described herein. This homologous recombination event can produce a chromosome which has exogenous DNA introduced, for example in frame, with the surrounding DNA. This type of protocol allows for very specific mutations, such as point mutations, to be introduced into the genome contained within the cell. Methods for performing this type of homologous recombination are disclosed herein.

V. SPECIFIC EMBODIMENTS

Disclosed herein is a eukaryotic microorganism having an 18S sequence, wherein the 18S sequence has at least 94% identity to the sequence set forth in SEQ ID NO:1. The eukaryotic microorganism can produce unsaturated fatty acids having a profile shown in FIG. 2. The eukaryotic microorganism can be from the phylum Labyrinthulomycota, the class Labyrinthulomycetes, the subclass Thraustochytridae, the order Thraustochytriales, the family Thraustochytriaceae, and/or the genus *Thraustochytrium*. The eukaryotic microorganism can be *Thraustochytrium* sp., *Thraustochytrium aureum*, *Thraustochytrium roseum*, or *Thraustochytrium striatum*. The eukaryotic microorganism can also be from the family Thraustochytriaceae and can have ATCC accession number 20888, 20889, 20890, 20891, or 20892.

Also disclosed herein is a eukaryotic microorganism having an 18S sequence, wherein the 18S sequence has at least 94% identity to the sequence set forth in SEQ ID NO:1, wherein the microorganism is from the genus *Schizochytrium*. The eukaryotic microorganism can be *Schizochytrium* sp.

Also disclosed herein is a eukaryotic microorganism having an 18S sequence, wherein the 18S sequence has at least 94% identity to the sequence set forth in SEQ ID NO:1, wherein the eukaryotic microorganism comprises an omega 3 or omega 6 fatty acid. The eukaryotic microorganism can also comprises DHA or DPA.

Also disclosed herein is a eukaryotic microorganism having an 18S sequence, wherein the 18S sequence has at least 94% identity to the sequence set forth in SEQ ID NO:1, wherein the microorganism produces a lipid or fatty acid fraction of at least about 4 wt. % to 6 wt. %. The lipid can comprise DHA. The lipid composition can also comprise from about 25 wt. % fatty acid fraction to about 40 wt. % fatty acid fraction of n-3 DHA, from about 6 wt. % fatty acid fraction to about 10 wt. % fatty acid fraction of n-6 DPA, and from about 0 wt. % fatty acid fraction to about 3 wt. % fatty acid fraction of n-3 EPA.

Also disclosed is a composition comprising a eukaryotic microorganism having an 18S sequence, wherein the 18S sequence has at least 94% identity to the sequence set forth in SEQ ID NO:1. The composition can further comprise a medium and/or nutrients Also disclosed is a composition comprising a eukaryotic microorganism having an 18S sequence, wherein the 18S sequence has at least 94% identity to the sequence set forth in SEQ ID NO:1, wherein the composition is a biomass. The eukaryotic microorganism of the composition can be from the phylum Labyrinthulomycota, the class Labyrinthulomycetes, the subclass Thraustochytridae, the order Thraustochytriales, the family Thraustochytriaceae, or the genus *Thraustochytrium*. The eukaryotic microorganism can be *Thraustochytrium* sp., *Thraustochytrium aureum*, *Thraustochytrium roseum*, or *Thraustochytrium striatum*. The eukaryotic microorganism can also be from the family Thraustochytriaceae and can have ATCC accession number 20888, 20889, 20890, 20891, or 20892.

Also disclosed is a composition comprising a eukaryotic microorganism having an 18S sequence, wherein the 18S sequence has at least 94% identity to the sequence set forth in SEQ ID NO:1, wherein the microorganism is from the genus *Schizochytrium*. The eukaryotic microorganism can be *Schizochytrium* sp.

Figure 2:
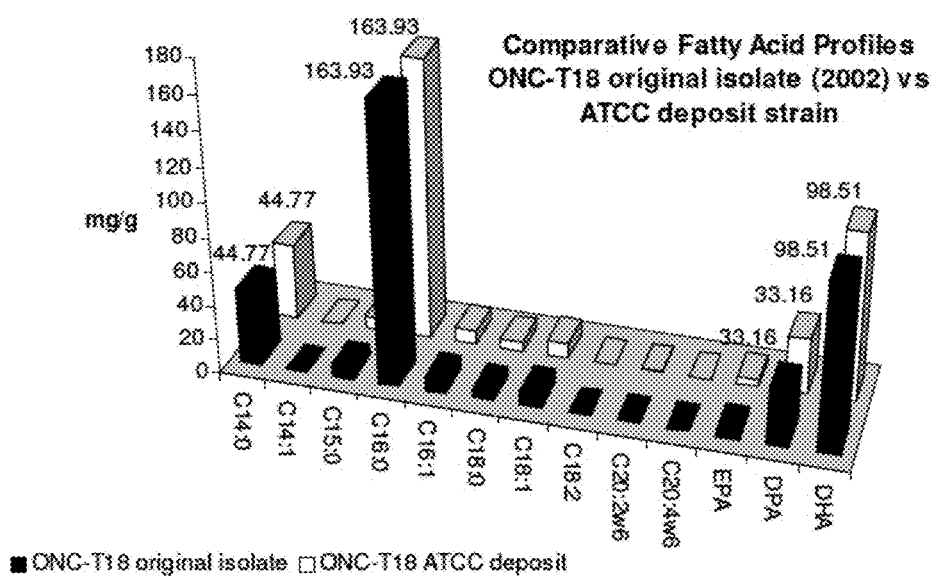

Also disclosed is a composition comprising a eukaryotic microorganism having an 18S sequence, wherein the 18S sequence has at least 94% identity to the sequence set forth in SEQ ID NO:1, wherein the eukaryotic microorganism produces unsaturated fatty acids having a profile shown in FIG. 2. The unsaturated fatty acid can comprise an omega 3 or omega 6 fatty acid. The unsaturated fatty acid can also comprise DHA or DPA.

Also disclosed is a composition comprising a eukaryotic microorganism having an 18S sequence, wherein the 18S sequence has at least 94% identity to the sequence set forth in SEQ ID NO:1, wherein the eukaryotic microorganism can produce a lipid or fatty acid fraction of at least about 4 wt. % to 6 wt. %. The lipid can comprise DHA. The lipid can also comprise from about 25 wt. % fatty acid fraction to about 40 wt. % fatty acid fraction of n-3 DHA, from about 6 wt. % fatty acid fraction to about 10 wt. % fatty acid fraction of n-6 DPA, and from about 0 wt. % fatty acid fraction to about 3 wt. % fatty acid fraction of n-3 EPA.

Also disclosed is a composition comprising a eukaryotic microorganism having an 18S sequence, wherein the 18S sequence has at least 80% identity to the sequence set forth in SEQ ID NO:1

Also disclosed is a comprising from about 25 wt. % fatty acid fraction to about 40 wt. % fatty acid fraction of n-3 DHA, from about 6 wt. % fatty acid fraction to about 10 wt. % fatty acid fraction of n-6 DPA, and from about 0 wt. % fatty acid fraction to about 3 wt. % fatty acid fraction of n-3 EPA.

Also disclosed is a method of preparing a lipid composition, the method comprising: culturing the eukaryotic microorganism described herein, in a heterotrophic medium, and isolating the lipid composition. Also disclosed is a lipid composition prepared according to this method.

Also disclosed is a delivery device comprising a any of the compositions described above. For example, disclosed is a delivery device comprising a composition comprising a eukaryotic microorganism having an 18S sequence, wherein the 18S sequence has at least 94% identity to the sequence set forth in SEQ ID NO:1. The delivery device can comprise a microcapsule, a microsphere, a nanosphere or nanoparticle, a liposome, a noisome, a nanoerythrosome, a solid-liquid nanoparticle, a leuprolide, a gel, a gel capsule, a tablet, a lotion, a cream, a spray, an emulsion, or a powder.

Also disclosed is a microcapsule, comprising an agglomeration of primary microcapsules and a loading substance, each individual primary microcapsule having a primary shell, wherein the loading substance comprises any of the compositions described above, and is encapsulated by the primary shell, and wherein the agglomeration is encapsulated by an outer shell. The primary shell and/or outer shell can comprise a surfactant, gelatin, polyphosphate, polysaccharide, or a mixture thereof. The primary shell and/or outer shell can also comprise gelatin type B, polyphosphate, gum arabic, alginate, chitosan, carrageenan, pectin, starch, modified starch, alfa-lactalbumin, beta-lactoglobulin, ovalbumin, polysorbiton, maltodextrin, cyclodextrin, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof. The primary shell and/or outer shell can also comprise a complex coacervate, gelatin type A, fish gelatin, a gelatin with a Bloom number of from about 0 to about 300, a gelatin with a Bloom number of from about 0 to about 50, a gelatin with a Bloom number of from about 51 to about 300, a gelatin with a Bloom number of about 0, about 210, about 220, or about 240, a coacervate of gelatin and polyphosphate.

The loading substance of the disclosed microcapsules can comprise oil from *Thraustochytrium*, *Schizochytrium*, or a mixture thereof. The loading substance can be from about 20% to about 90% or 50% to about 70% by weight of the microcapsule.

The outer shell of the disclosed microcapsules can have an average diameter of from about 1 μm to about 2,000 μm, about 20 μm to about 1,000 μm, about 30 μm to about 80 μm, about 40 nm to about 10 μm, or about 0.1 μm to about 5 μm.

Also disclosed is a nutritional supplement that comprises any of the compositions, delivery devices, or microcapsules described above. The disclosed nutritional supplements can be in the form of a tablet, gel-cap, capsule, liquid, or syrup.

Also disclosed is a foodstuff that comprises any of the compositions, delivery devices, or microcapsules described above. The foodstuff can be a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar, a sauce, a gravy, a syrup, a nutritional bar, a beverage, a dry beverage powder, a jam or jelly, an infant formula, or a baby food. The foodstuff can also be a fish product, a companion pet food, a livestock or an aquaculture feed. The foodstuff can also be bread, tortillas, cereal, sausage, chicken, ice cream, yogurt, milk, salad dressing, rice bran, fruit juice, a dry beverage powder, rolls, cookies, crackers, fruit pies, or cakes.

Also disclosed is a method of delivering a composition to a subject, comprising administering to the subject any of the compositions, delivery devices, microcapsules, or foodstuffs described above. The subject can be a mammal. The subject can also be a human.

Also disclosed is a use of any of the microcapsules described above and to prepare a medicament for delivering a loading substance to a subject.

Also disclosed is a method of lowering cholesterol levels, triglyceride levels, or a combination thereof in a subject, comprising the step of administering to the subject an effective amount of any of the compositions, delivery devices, microcapsules, nutritional supplements, or foodstuffs described above.

Also disclosed is a method of supplementing essential trace elements in a subject, the method comprising the step of administering to the subject an effective amount of any of the compositions, delivery devices, microcapsules, nutritional supplements, or foodstuffs described above, wherein the composition, delivery device, microcapsule, supplement, and foodstuff comprises an essential trace element.

Also disclosed is a method of improving insulin sensitivity in a subject, comprising the step of administering to the subject an effective amount of any of the compositions, delivery devices, microcapsules, nutritional supplements, or foodstuffs described above.

Also disclosed is a method of reducing hyperglycemia in a subject, comprising the step of administering to the subject an effective amount of any of the compositions, delivery devices, microcapsules, nutritional supplements, or foodstuffs described above.

Also disclosed is a method of reducing hypercholesterolemia in a subject, comprising the step of administering to the subject an effective amount of any of the compositions, delivery devices, microcapsules, nutritional supplements, or foodstuffs described above.

Also disclosed is a method of reducing body fat in a subject, comprising the step of administering to the subject an effective amount of any of the compositions, delivery devices, microcapsules, nutritional supplements, or foodstuffs described above.

Also disclosed is a method of promoting weight loss in a subject, comprising the step of administering to the subject an effective amount of any of the compositions, delivery devices, microcapsules, nutritional supplements, or foodstuffs described above.

Also disclosed is a method of treating or preventing diabetes in a subject, comprising the step of administering to the subject an effective amount of any of the compositions, delivery devices, microcapsules, nutritional supplements, or foodstuffs described above.

Also disclosed is a pharmaceutical formulation comprising any of the compositions, delivery devices, or microcapsules described above, and a pharmaceutical carrier.

Also disclosed is a foodstuff comprising a composition comprising a eukaryotic microorganism having an 18S sequence, wherein the 18S sequence has at least 94% identity to the sequence set forth in SEQ ID NO:1. The foodstuff can be a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar, a sauce, a gravy, a syrup, a nutritional bar, a beverage, a dry beverage powder, a jam or jelly, an infant formula, or a baby food. The foodstuff can also be a fish product, or pet companion food, a livestock or an aquaculture feed. The foodstuff can also be bread, tortillas, cereal, sausage, chicken, ice cream, yogurt, milk, salad dressing, rice bran, fruit juice, a dry beverage powder, rolls, cookies, crackers, fruit pies, or cakes.

Also disclosed is a method of lowering cholesterol levels, triglyceride levels, or a combination thereof in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of supplementing essential trace elements in a subject, the method comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method improving insulin sensitivity in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of reducing hyperglycemia in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of reducing hypercholesterolemia in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of reducing body fat in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of promoting weight loss in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a method of treating or preventing diabetes in a subject, comprising the step of administering an effective amount of a composition comprising a eukaryotic microorganism having an 18S sequence, wherein the 18S sequence has at least 94% identity to the sequence set forth in SEQ ID NO:1, a nutritional supplement comprising a composition comprising a eukaryotic microorganism having an 18S sequence, wherein the 18S sequence has at least 94% identity to the sequence set forth in SEQ ID NO:1, a delivery device comprising a composition comprising a eukaryotic microorganism having an 18S sequence, 10 wherein the 18S sequence has at least 94% identity to the sequence set forth in SEQ ID NO:1, or a foodstuff comprising a composition comprising a eukaryotic microorganism having an 18S sequence, wherein the 18S sequence has at least 94% identity to the sequence set forth in SEQ ID NO:1.

Also disclosed is a pharmaceutical formulation comprising a composition comprising a eukaryotic microorganism having an 18S sequence, wherein the 18S sequence has at least 94% identity to the sequence set forth in SEQ ID NO:1.

VI. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Isolation of ONC-T18 *Thraustochytrium* sp. Strain

Classical bacteriological strain purification techniques were employed in order to isolate ONC-T18 from mangrove leaves collected at Advocate Harbor, Nova Scotia. ONC-T18 was serially cultured at 25° C. on a nutrient medium agar containing 5 g $L^{-1}$ glucose, 2 g $L^{-1}$ peptone, 2 g $L^{-1}$ yeast extract and 15.0 g $L^{-1}$ agar to 1 L of 0.2 μm filtered sea water until purity was assured. Subsequently, a liquid medium containing 15% artificial sea water (trophic marine), supplemented with a nitrogen and carbon source, being 60 g $L^{-1}$ glucose and 10 g $L^{-1}$ yeast extract, respectively, was prepared. This medium (50 ml of medium in 250 ml flasks) was inoculated with ONC-T18, then incubated at 25° C. and aerated via shaking at 120 rpm.

ONC-T18 was separated from medium via centrifugation, with cellular biomass then washed, recentrifuged and freeze dried to completion. Cellular biomass was then weighed in order to determine culture efficiencies with biomass per liter medium values recorded. Extraction of lipid fraction from biomass and subsequent fatty acid methyl ester separation was performed using the Bligh & Dyer method. Transesterification was performed by transferring freeze dried cellular material to a 10 ml screw-top test tube and adding 10% methanolic HCl and dichloromethane to the tube, with the mixture allowed to react for 2 hours at 90° C. Fatty acid methyl esters were then extracted via addition of hexane: chloroform, and the methyl ester component measured via gas chromatography (FID) in order to determine the fatty acid profile of each microorganism and the symbiotic community (ONC-T18). Concentrations of each fatty acid methyl ester (C14:0 to C22:6) were determined by comparison of the GC peak areas of two internal standards (C19:0 and C23:0) added in defined amounts both at the beginning (C23:0) and end (C19:0) of the transesterification process. The total amount of fatty acids per gram of dried cell biomass and the percentage content of each fatty acid, calculated using this method, are shown in FIG. 2.

Figure 1:
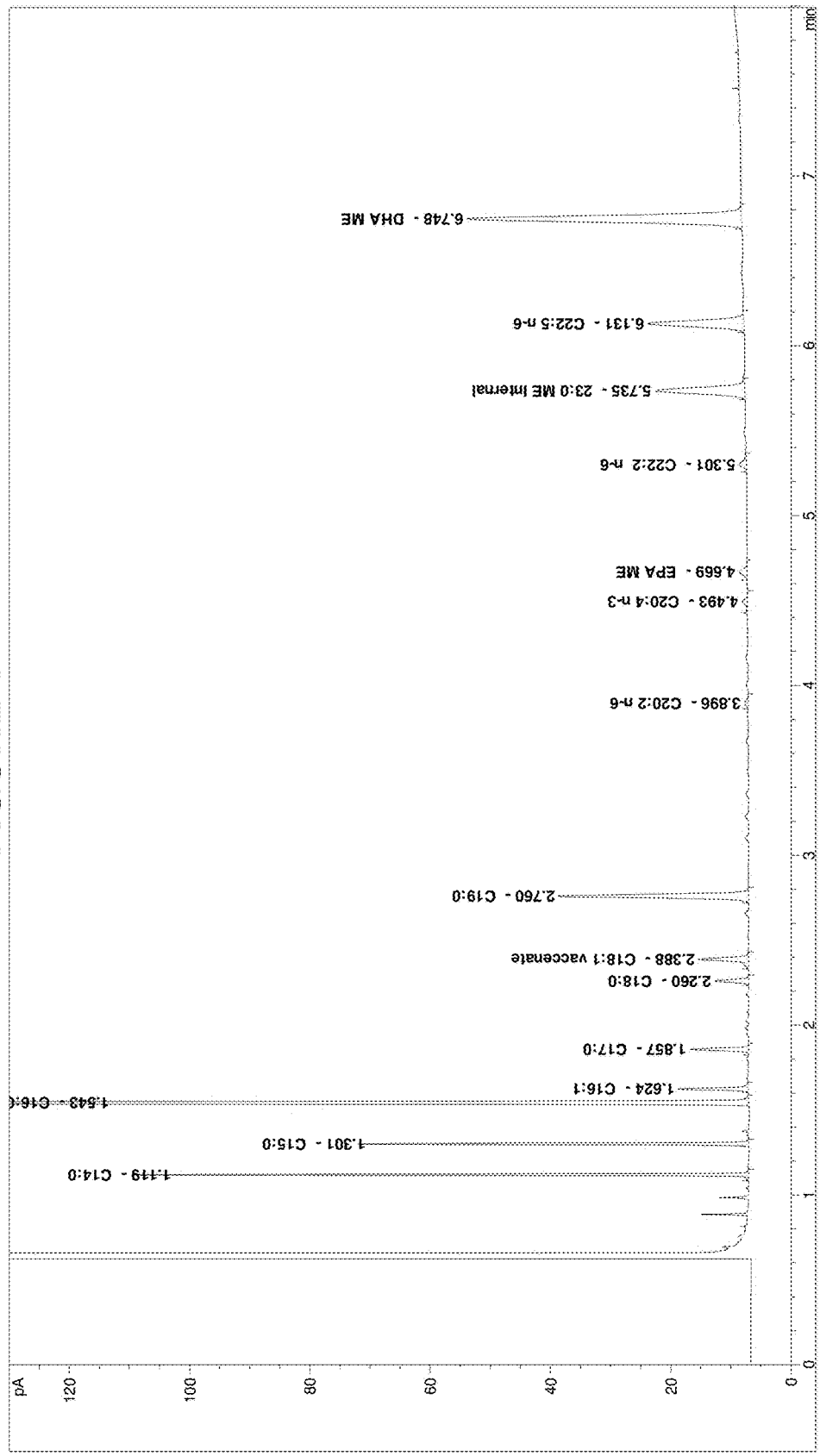

From analysis of these results, in conjunction with those shown in FIG. 1, it can be seen that ONC-T18 demonstrated the ability to produce increased amounts of DHA, as well as marked quantities of EPA and DPA. ONC-T18, produces of approximately 25% DHA, 8.0% (n-6) DPA and 1.0% EPA within this non-optimized fermentation medium. Subsequently, ONC-T18 was chosen on the basis of a combination of economically desirable characteristics: (1) capable of maximal heterotrophic growth (compared to control strains); (2) contain a high percentage of omega-3 highly unsaturated fatty acids; (3) capable of growth on inexpensive nutrients; (4) thermotolerance, and are (5) euryhaline.

In addition, multiple different strains of oil producing microbes were compared to ONC-T18. Each of these microbes is believed to comprise a Thraustochyrid, and produces oil in the amounts shown in Table 3.

TABLE 3

| | [ ] = mg/g | | |
|---|---|---|---|
| | [ ] DHA | [ ] EPA | Total Lipid | Weight (g) |
| MYA-1381 | 127.96 | 5.52 | 216.37 | 1.80 |
| ATCC-20891 | 37.97 | 7.14 | 67.34 | 1.30 |
| ONC-T01 | 5.18 | 7.76 | 50.82 | 0.40 |
| ONC-T02 | 31.84 | 4.20 | 52.88 | 0.50 |
| ONC-T03 | 24.87 | 6.97 | 75.00 | 0.60 |
| ONC-T04 | 14.39 | 4.49 | 41.74 | 0.90 |
| ONC-T05 | 11.37 | 3.97 | 34.89 | 0.10 |
| ONC-T06 | 27.80 | 6.71 | 63.87 | 0.10 |
| ONC-T07 | 33.02 | 5.49 | 61.81 | 0.50 |
| ONC-T08 | 24.48 | 4.83 | 53.35 | 0.80 |
| ONC-T09 | 63.82 | 4.25 | 109.12 | 0.80 |
| ONC-T10 | 22.22 | 4.93 | 40.99 | 0.10 |
| ONC-T11 | 18.37 | 21.25 | 214.98 | 0.80 |
| ONC-T12 | 57.96 | 9.03 | 96.26 | 0.60 |
| ONC-T13 | 12.90 | 4.57 | 39.52 | 1.30 |
| ONC-T14 | 15.99 | 5.16 | 36.46 | 0.50 |
| ONC-T15 | 15.53 | 5.11 | 37.72 | 0.50 |
| ONC-T16 | 18.02 | 5.55 | 42.12 | 0.50 |
| ONC-T17 | 36.43 | 4.34 | 94.26 | 0.30 |
| ONC-T18 | 83.63 | 2.76 | 321.14 | 2.30 |
| ONC-T19 | 34.71 | 8.07 | 66.14 | 0.60 |
| ONC-T20 | 19.28 | 6.94 | 66.74 | 0.10 |
| ONC-T21 | | | | |
| ONC-T22 | 22.72 | 3.26 | 47.58 | 0.60 |
| ONC-T23 | | | | |
| ONC-T24 | 11.73 | 3.56 | 33.56 | 0.70 |
| ONC-T25 | 26.99 | 6.11 | 45.67 | 0.60 |
| ONC-T26 | 14.50 | 6.43 | 39.22 | 0.60 |
| ONC-T27 | 26.83 | 7.75 | 61.87 | 0.70 |
| ONC-T28 | 16.62 | 6.02 | 38.28 | 0.90 |
| ONC-T29 | 14.67 | 4.91 | 34.48 | 0.80 |
| ONC-T30 | 16.56 | 5.42 | 81.88 | 0.80 |
| ONC-T31 | 13.36 | 5.74 | 44.86 | 0.30 |
| ONC-T32 | 19.12 | 6.56 | 53.29 | 0.20 |
| ONC-T33 | | | | |

TABLE 3-continued

| | [ ] = mg/g | | |
|---|---|---|---|
| | [ ] DHA | [ ] EPA | Total Lipid | Weight (g) |
| ONC-T34 | 18.92 | 5.98 | 53.36 | 0.60 |
| ONC-T35 | | | | |
| ONC-T36 | | | | |
| ONC-T37 | 35.69 | 11.06 | 82.73 | 0.10 |
| ONC-T38 | 22.73 | 10.94 | 51.56 | 0.10 |
| ONC-T39 | | | | |
| ONC-T40 | 26.87 | 8.83 | 67.87 | 0.80 |
| ONC-T41 | 22.85 | 6.65 | 52.63 | 0.50 |
| ONC-T42 | 33.65 | 9.22 | 83.93 | 0.80 |
| ONC-T43 | 12.49 | 3.25 | 37.93 | 0.80 |
| ONC-T44 | 11.71 | 2.93 | 55.05 | 1.10 |
| ONC-T45 | 26.08 | 7.95 | 70.45 | 0.70 |
| ONC-T46 | 33.34 | 6.27 | 63.76 | 0.30 |
| ONC-T47 | 10.01 | 4.77 | 68.02 | 0.70 |
| ONC-T48 | 26.23 | 3.95 | 69.06 | 0.60 |
| ONC-T49 | 16.64 | 4.89 | 39.76 | 0.30 |
| ONC-T50 | 13.64 | 4.56 | 40.30 | 1.00 |
| ONC-T51 | | | | |
| ONC-T52 | 26.57 | 4.55 | 41.36 | 0.60 |
| ONC-T53 | 11.40 | 3.56 | 29.20 | 0.70 |
| ONC-T54 | 10.34 | 3.18 | 29.31 | 0.70 |
| ONC-T55 | | | | |
| ONC-T56 | | | | |
| ONC-T57 | | | | |
| ONC-T58 | 10.30 | 3.13 | 27.10 | 0.70 |
| ONC-T59 | | | | |
| ONC-T60 | 27.71 | 7.01 | 66.84 | 0.30 |
| ONC-T61 | 15.72 | 5.62 | 52.56 | 0.40 |
| ONC-T62 | | | | |
| ONC-T63 | 20.17 | 8.25 | 62.58 | 0.60 |
| ONC-T64 | 12.16 | 2.97 | 44.73 | 1.10 |
| ONC-T65 | | | | |
| ONC-T66 | | | | |
| ONC-T67 | 23.71 | 5.63 | 43.24 | 0.50 |
| ONC-T68 | 22.72 | 6.10 | 41.37 | 0.50 |

It is understood that just as for ONC-T18, as described herein, a set of oil producing microbes as represented by the oil producing capabilities disclosed herein are disclosed, such as by a percentage of DHA to total oil production, or by total DHA production, for example.

2. Example 2: Identification Eukaryotic *Thraustochytrium* Species of ONC-T18 Using Genetic Techniques Using polymerase chain reaction (PCR) techniques and primers targeting the 18S ribosomal RNA gene, being universal for all eukaryotic species, it was possible to generate PCR products of the structural genes of the eukaryotic microorganism isolated from ONC-T18 (as per example 1). PCR products were then sequenced and designated SEQ ID NO:1 for the eukaryotic species (see FIG. 2).

Comparison of SEQ ID NO:1 with nucleic acid sequences found in the genomic database, GenBank (National Centre for Biotechnology Information, National Institute of Health, Bethesda, Md., USA) using the BLAST (Basic local alignment search tool) algorithm identified SEQ ID NO:1 as being most related to *Thraustochytrium striatum* [AF265338] (97.5% similarity).

BLAST results for ONC-T18 *Thraustochytrium* sp. are shown below.

| Sequences producing significant alignments: | Score (bits) | E Value |
|---|---|---|
| gi\|14279326\|gb\|AF265338.1\| *Thraustochytrium striatum* small subun . . . | 2126 | 0.0 |
| gi\|50508012\|dbj\|AB183657.1\| *Thraustochytriidae* sp. MBIC11072 gen . . . | 2121 | 0.0 |
| gi\|54778780\|gb\|AY773276.1\| *Thraustochytriidae* sp. FJN-10 18S rib . . . | 1857 | 0.0 |
| gi\|50508019\|dbj\|AB183664.1\| *Thraustochytriidae* sp. MBIC11093 gen . . . | 1828 | 0.0 |
| gi\|38524571\|dbj\|AB126669.1\| *Thraustochytrium* sp. CHN-1 gene for . . . | 1748 | 0.0 |
| gi\|24817740\|dbj\|AB073308.2\| *Thraustochytriidae* sp. N1-27 gene fo . . . | 1628 | 0.0 |
| gi\|50508018\|dbj\|AB183663.1\| *Thraustochytriidae* sp. MBIC11092 gen . . . | 1257 | 0.0 |
| gi\|50508017\|dbj\|AB183662.1\| *Thraustochytriidae* sp. MBIC11091 gen . . . | 1257 | 0.0 |
| gi\|50508015\|dbj\|AB183660.1\| *Thraustochytriidae* sp. MBIC11084 gen . . . | 1255 | 0.0 |
| gi\|50508011\|dbj\|AB183656.1\| *Thraustochytriidae* sp. MBIC11070 gen . . . | 1255 | 0.0 |
| gi\|50508016\|dbj\|AB183661.1\| *Thraustochytriidae* sp. MBIC11086 gen . . . | 1249 | 0.0 |
| gi\|15823623\|dbj\|AB052555.1\| *Schizochytrium* sp. KH105 gene for 18 . . . | 1245 | 0.0 |
| gi\|50508013\|dbj\|AB183658.1\| *Thraustochytriidae* sp. MBIC11075 gen . . . | 1227 | 0.0 |
| gi\|50508010\|dbj\|AB183655.1\| *Thraustochytriidae* sp. MBIC11067 gen . . . | 1213 | 0.0 |
| gi\|54303872\|gb\|AY758384.1\| *Schizochytrium* sp. FJU-512 18S riboso . . . | 1158 | 0.0 |
| gi\|14279326\|gb\|AF265338.1\|AF265338 *Thraustochytrium striatum* sma . . . | 1106 | 0.0 |
| gi\|6492308\|gb\|AF155209.1\|AF155209 Labyrinthulid quahog parasite . . . | 765 | 0.0 |
| gi\|16209570\|gb\|AY052644.1\| Labyrinthulid quahog parasite QPX sma . . . | 757 | 0.0 |
| gi\|9755031\|gb\|AF261664.1\|AF261664 Labyrinthulid quahog parasite . . . | 757 | 0.0 |
| gi\|58176547\|gb\|AY870336.1\| *Thraustochytriidae* sp. Fng1 18S ribos . . . | 735 | 0.0 |
| gi\|67624914\|dbj\|AB191425.1\| Uncultured eukaryote gene for small . . . | 724 | 0.0 |
| gi\|5509891\|dbj\|AB022112.1\| *Thraustochytrium striatum* gene for 18 . . . | 724 | 0.0 |
| gi\|561884\|gb\|L34054.1\|ULKRRE *Ulkenia profunda* 18S ribosomal RNA . . . | 702 | 0.0 |
| gi\|50508014\|dbj\|AB183659.1\| *Thraustochytriidae* sp. MBIC11077 gen . . . | 686 | 0.0 |
| gi\|50508008\|dbj\|AB183653.1\| *Thraustochytriidae* sp. MBIC11060 gen . . . | 686 | 0.0 |
| gi\|50508009\|dbj\|AB183654.1\| *Thraustochytriidae* sp. MBIC11063 gen . . . | 658 | 0.0 |
| gi\|41391986\|emb\|AJ535188.1\| *Pleurosira* cf. *laevis* 18S rRNA gene, . . . | 634 | e−178 |
| gi\|28316562\|gb\|AF525670.1\| *Pleurosira laevis* small subunit ribos . . . | 634 | e−178 |
| gi\|5509889\|dbj\|AB022110.1\| *Thraustochytrium aureum* gene for 18S . . . | 634 | e−178 |
| gi\|561883\|gb\|L34668.1\|TUKRRE *Thraustochytrium kinnei* 18S ribosom . . . | 628 | e−176 |
| gi\|5509894\|dbj\|AB022115.1\| *Ulkenia radiata* gene for 18S rRNA | 624 | e−175 |
| gi\|5509893\|dbj\|AB022114.1\| *Ulkenia profunda* gene for 18S rRNA | 624 | e−175 |
| gi\|5509895\|dbj\|AB022116.1\| *Ulkenia visurgensis* gene for 18S rRNA | 603 | e−169 |
| gi\|9027563\|gb\|AF257315.2\| *Thraustochytriidae* sp. BS2 18S ribosom . . . | 589 | e−164 |
| gi\|5509886\|dbj\|AB022107.1\| *Schizochytrium limacinum* gene for 18S . . . | 581 | e−162 |
| gi\|48727879\|gb\|AY620254.1\| *Metromonas simplex* clone TC-S small s . . . | 571 | e−159 |
| gi\|33309650\|gb\|AF411282.1\| Unidentified cercozoan 18S ribosomal . . . | 569 | e−158 |
| gi\|28076844\|gb\|AF530543.1\| Uncultured eukaryote clone AT4-68 18S . . . | 531 | e−147 |
| gi\|30144485\|gb\|AY256273.1\| Uncultured eukaryote isolate E170 sma . . . | 517 | e−143 |
| gi\|30144529\|gb\|AY256317.1\| Uncultured eukaryote isolate D107 sma . . . | 507 | e−140 |
| gi\|14579477\|gb\|AF363207.1\| Eukaryote marine clone ME1-24 18S rib . . . | 505 | e−139 |
| gi\|39578677\|gb\|AY426906.1\| Uncultured marine eukaryote clone BL0 . . . | 504 | e−139 |
| gi\|39981869\|gb\|AY381216.1\| Uncultured eukaryote clone BL010625.3 . . . | 504 | e−139 |
| gi\|73533408\|gb\|DQ103811.1\| Uncultured marine eukaryote clone M4_ . . . | 504 | e−139 |
| gi\|73533402\|gb\|DQ103805.1\| Uncultured marine eukaryote clone M3_ . . . | 504 | e−139 |
| gi\|73533389\|gb\|DQ103792.1\| Uncultured marine eukaryote clone M2_ . . . | 504 | e−139 |
| gi\|73533382\|gb\|DQ103785.1\| Uncultured marine eukaryote clone M1_ . . . | 504 | e−139 |
| gi\|30144534\|gb\|AY256322.1\| Uncultured eukaryote isolate D179 sma . . . | 504 | e−139 |
| gi\|24817738\|dbj\|AB073305.2\| *Thraustochytriidae* sp. H1-14 gene fo . . . | 504 | e−139 |
| gi\|30268157\|emb\|AJ519935.1\|1AST519935 *Aplanochytrium stocchinoi* p . . . | 504 | e−139 |
| gi\|58531881\|gb\|AY882527.1\| Uncultured marine eukaryote clone T41 . . . | 504 | e−139 |
| gi\|463127\|gb\|L27634.1\|LADDLRRNA *Labyrinthuloides minuta* 16S-like . . . | 504 | e−139 |
| gi\|39981839\|gb\|AY381186.1\| Uncultured eukaryote clone OR000415.1 . . . | 502 | e−138 |
| gi\|39981824\|gb\|AY381171.1\| Uncultured eukaryote clone HE001005.1 . . . | 502 | e−138 |
| gi\|18026024\|gb\|AY046848.1\| Uncultured eukaryote isolate C3_E019 . . . | 502 | e−138 |
| gi\|18026022\|gb\|AY046846.1\| Uncultured eukaryote isolate C3_E017 . . . | 502 | e−138 |
| gi\|18026014\|gb\|AY046838.1\| Uncultured eukaryote isolate C3_E008 . . . | 502 | e−138 |
| gi\|18026008\|gb\|AY046832.1\| Uncultured eukaryote isolate C3_E002 . . . | 502 | e−138 |
| gi\|18025980\|gb\|AY046804.1\| Uncultured eukaryote isolate C2_E014 . . . | 502 | e−138 |
| gi\|18025969\|gb\|AY046793.1\| Uncultured eukaryote isolate C2_E002 . . . | 502 | e−138 |
| gi\|18025801\|gb\|AY046625.1\| Uncultured eukaryote isolate C1_E024 . . . | 502 | e−138 |
| gi\|67624915\|dbj\|AB191426.1\| Uncultured eukaryote gene for small . . . | 502 | e−138 |
| gi\|67624913\|dbj\|AB191424.1\| Uncultured eukaryote gene for small . . . | 502 | e−138 |
| gi\|67624912\|dbj\|AB191423.1\| Uncultured eukaryote gene for small . . . | 502 | e−138 |
| gi\|39981861\|gb\|AY381208.1\| Uncultured eukaryote clone BL010320.1 . . . | 500 | e−138 |
| gi\|14349249\|dbj\|AB052556.1\| *Thraustochytrium* sp. KK17-3 gene for . . . | 500 | e−138 |
| gi\|20219962\|dbj\|AB073307.1\| *Thraustochytriidae* sp. M4-103 gene f . . . | 498 | e−137 |
| gi\|59709960\|gb\|AY916582.1\| Uncultured eukaryote clone Zeuk76 18S . . . | 496 | e−136 |
| gi\|18025960\|gb\|AY046784.1\| Uncultured eukaryote isolate A3_E043 . . . | 496 | e−136 |
| gi\|18025789\|gb\|AY046613.1\| Uncultured eukaryote isolate C1_E009 . . . | 496 | e−136 |
| gi\|30144548\|gb\|AY256336.1\| Uncultured eukaryote isolate D278 sma . . . | 496 | e−136 |
| gi\|2138106\|gb\|U59933.1\|U59933 *Scybalium jamaicense* 18S ribosomal . . . | 496 | e−136 |
| gi\|53828186\|gb\|AY744948.1\| *Phytophthora palmivora* isolate 88108 . . . | 494 | e−136 |
| gi\|60687349\|gb\|AY821976.1\| Uncultured oomycete clone CV1_B2_5 sm . . . | 494 | e−136 |
| gi\|60687347\|gb\|AY821974.1\| Uncultured *Phytophthora*-like oomycete . . . | 494 | e−136 |
| gi\|60687342\|gb\|AY821969.1\| Uncultured oomycete clone CV1_B1_49 s . . . | 494 | e−136 |
| gi\|39981870\|gb\|AY381217.1\| Uncultured eukaryote clone BL010625.3 . . . | 494 | e−136 |
| gi\|39981864\|gb\|AY381211.1\| Uncultured eukaryote clone BL010320.2 . . . | 494 | e−136 |

-continued

| Sequences producing significant alignments: | Score (bits) | E Value |
|---|---|---|
| gi\|39981860\|gb\|AY381207.1\| Uncultured eukaryote clone BL010320.6 . . . | 494 | e-136 |
| gi\|39981844\|gb\|AY381191.1\| Uncultured eukaryote clone BL000921.1 . . . | 494 | e-136 |
| gi\|18026046\|gb\|AY046870.1\| Uncultured eukaryote isolate C3_E044 . . . | 494 | e-136 |
| gi\|18026039\|gb\|AY046863.1\| Uncultured eukaryote isolate C3_E035 . . . | 494 | e-136 |
| gi\|18026031\|gb\|AY046855.1\| Uncultured eukaryote isolate C3_E026 . . . | 494 | e-136 |
| gi\|42412527\|gb\|AY486144.1\| *Pythium insidiosum* 18S ribosomal RNA . . . | 494 | e-136 |
| gi\|73533425\|gb\|DQ103828.1\| Uncultured marine eukaryote clone M2_ . . . | 494 | e-136 |
| gi\|34576227\|gb\|AY129064.1\| Uncultured marine eukaryote UEPAC45p4 . . . | 494 | e-136 |
| gi\|30144522\|gb\|AY256310.1\| Uncultured eukaryote isolate D85 smal . . . | 494 | e-136 |
| gi\|30144521\|gb\|AY256309.1\| Uncultured eukaryote isolate D84 smal . . . | 494 | e-136 |
| gi\|30144518\|gb\|AY256306.1\| Uncultured eukaryote isolate D79 smal . . . | 494 | e-136 |
| gi\|30144475\|gb\|AY256263.1\| Uncultured eukaryote isolate E106 sma . . . | 494 | e-136 |
| gi\|30144473\|gb\|AY256261.1\| Uncultured eukaryote isolate E94 smal . . . | 494 | e-136 |
| gi\|21954246\|gb\|AY116220.1\| Uncultured eukaryote clone ANT12-26 1 . . . | 494 | e-136 |
| gi\|41393027\|emb\|AJ535176.1\|LMI535176 *Leptocylindrus* minimum 18S . . . | 494 | e-136 |
| gi\|53693111\|gb\|AY742743.1\| *Phytophthora tropicalis* isolate 129F- . . . | 494 | e-136 |
| gi\|53693108\|gb\|AY742759.1\| *Pythium vexans* isolate Pyv6-2 18S rib . . . | 494 | e-136 |
| gi\|53693105\|gb\|AY742756.1\| *Pythium splendens* isolate 117 18S rib . . . | 494 | e-136 |
| gi\|53693104\|gb\|AY742755.1\| *Pythium aphanidermatum* 18S ribosomal . . . | 494 | e-136 |
| gi\|53693097\|gb\|AY742748.1\| *Phytophthora capsici* isolate 98110 18 . . . | 494 | e-136 |
| gi\|53693096\|gb\|AY742747.1\| *Phytophthora tropicalis* isolate 23047 . . . | 494 | e-136 |
| gi\|53693094\|gb\|AY742745.1\| *Phytophthora palmivora* isolate 8829 1 . . . | 494 | e-136 |
| gi\|58531862\|gb\|AY882508.1\| Uncultured marine eukaryote clone T53 . . . | 494 | e-136 |

3. Example 3: Optimized Production of Biomass Using Strain ONC-T18

Production of microbial derived (or single celled) oils are dependent on a variety of process variables, such as initial inoculum level, type of substrate, media composition, temperature and pH. Specifically, microbial-based production of highly unsaturated fatty acids using *Thraustochytrid* strains, shows a direct correlation between biomass and fatty acid production. Consequently, an understanding of the basic needs or optimization of parameters is an important factor in achieving maximum output. Therefore, in order to determine the best medium for production of increased fatty acid quantities, initial biomass optimization experiments were undertaken. Specifically, the recently developed Taguchi method (Joseph J and Piganatiells J R, *IIE Trans* 20:247-254, 1998), based on orthogonal arrays, was used in order to determine the optimum medium configuration for increased optical density (directly related to biomass production). In this instance, the Taguchi method was used to gain an understanding of the cumulative effects of the variables that pose an impact on biomass production. The effects of variations in nitrogen (yeast extract, peptone, L-glutamate), carbon (glucose) and salt 10 concentration (artificial sea salt) had on biomass production. Therefore, a variety of liquid media were prepared with varying amounts of yeast extract, peptone and L-glutamate (0, 4, 10, 20, 50 g L$^{-1}$) as relates to varying amounts of glucose and sea salt solution (5, 40, 100, 160, 200 g L$^{-1}$ and 0, 6, 20, 30, 40 g L$^{-1}$, respectively). Concentrations were calculated according to a L25 orthogonal array in such a way that nitrogen medium of choice was discerned through the use of signal to noise ratio (SNL) analysis at 48 and 120 hrs, using the following formula:

$$SNL = -10 \log\left[\frac{1}{n}\sum_{i=1}^{n}\frac{1}{y_i^2}\right]$$

where, n=number of levels and y=yield (average OD$_{600}$ from triplicate experiments).

Results from these experiments (which specifically target biomass considerations), as shown within FIG. 2 below, demonstrated that the rate of nitrogen utilization by ONC-T18 as relates to optical density (OD$_{600}$) was peptone, then yeast extract followed by L-glutamate. However, based on growth maxima the best nitrogen sources for increase biomass production was yeast extract, then peptone, followed by L-glutamate. Furthermore, through the use of similar experiments with variations in glucose and salinity (sea salt concentration), the optimal and cheapest medium composition for the production of ONC-T18 biomass was within a medium comprising 2 g L$^{-1}$ yeast extract, 8 g L$^{-1}$ MSG, 60 g L$^{-1}$ glucose and 6 g L$^{-1}$ sea salt.

4. Example 4: Optimized Production of Docosahexaenoic Acid (DHA) by Strain ONC-T18

Media consisting of a nitrogen source (either peptone, yeast extract, L-glutamate (MSG) or combinations of these) and a carbon source (glucose), in a saline (artificial sea water) solution, were prepared in order to determine the best media composition for optimal biomass and DHA production in a similar manner to that described in Example 3 (shown in Table 4). After cultivation at 25° C. and 130 rpms over 3 days, biomass, total fatty acid per liter of medium, percent content of fatty acids by weight, percent content of DHA in total fatty acids and the amount of DHA per liter of medium were determined via gas chromatography as per method described in example 1, and herein, and shown in Table 4 below.

In this case, DHA was confirmed by comparison to known standards of DHA using gas chromatography mass spectrometry and peak locking methods. Findings from experimental package ❶, where variations in both natural and organic forms of nitrogen were investigated, showed that the optimal media composition should contain between 4.0 and 6.0 g L$^{-1}$ of both yeast extract and L-glutamate for optimal biomass and DHA production. Experimental package ❷, on the other hand, which investigated changes in the composition of sodium added to the medium showed optimal DHA production and biomass production when artificial sea salt is used. Moreover, experimental package ❷, in which the concentration of sodium within the medium was varied, depicted maxima for DHA and biomass production between 5 and 15% artificial seawater $L^{-1}$ $dH_2O$. Results from experimental package ❹, where variations in glucose levels were evaluated, demonstrated that the range of 40 to less than 160 g $L^{-1}$ glucose translated into optimal biomass and DHA production. Finally, results of experimental package ❺ indicate that ONC-T18 produced equivalent values for both cellular biomass and DHA concentration, when glucose or glycerol were used as carbon sources.

resuspended in methanol:chloroform:$H_2O$ (2:1:0.8 vol/vol/vol) and the process repeated with supernatants being pooled and moved to a separation funnel. 5 ml of chloroform and 5 ml of $H_2O$ were then added to funnel resulting in the formation of a two-phase liquid system. After vigorous mixing within separation funnel, the chloroform layer was removed, concentrated under $N_2$ gas, resuspended in chloroform and stored at −20° C. under analyzed. Approximately 1 µl of the total lipid fraction was spotted on multiple chromarods, separated and analyzed using an Iatroscan MK6 TLC/FID instrument.

TABLE 4

Results of DHA production optimization experiments with respect to variations in medium compositions.

| | Exp No. | Carbon source used | Amount added (g $L^{-1}$) | Salt types Salt mix used | Amount added (% salinity) | Nitrogen Sources Yeast extract (g $L^{-1}$) | MSG (g $L^{-1}$) | Total fatty acids (g $L^{-1}$) | Percent fatty acids (wt %) | Percent content DHA (wt %) | Amount of DHA (g $L^{-1}$) |
|---|---|---|---|---|---|---|---|---|---|---|---|
| ❶ | 401 | Glucose | 60.0 | Sea salt | 15.0 | 10.0 | 0.0 | 7.7 | 34.53 | 20.20 | 1.5579 |
| | 402 | Glucose | 60.0 | Sea salt | 15.0 | 8.0 | 2.0 | 10.0 | 44.01 | 17.09 | 1.7156 |
| | 403 | Glucose | 60.0 | Sea salt | 15.0 | 6.0 | 4.0 | 11.5 | 50.69 | 16.23 | 1.8624 |
| | 404 | Glucose | 60.0 | Sea salt | 15.0 | 4.0 | 6.0 | 16.9 | 69.07 | 24.19 | 4.0877 |
| | 405 | Glucose | 60.0 | Sea salt | 15.0 | 2.0 | 8.0 | 21.3 | 81.73 | 20.99 | 4.4752 |
| | 406 | Glucose | 60.0 | Sea salt | 15.0 | 0.0 | 10.0 | 0.15 | 1.97 | 28.81 | 0.0426 |
| ❷ | 407 | Glucose | 60.0 | Sea salt | 15.0 | 10.0 | 0.0 | 13.2 | 58.92 | 31.44 | 4.1362 |
| | 408 | Glucose | 60.0 | NaCl | 15.0 | 10.0 | 0.0 | 9.6 | 63.75 | 38.45 | 3.7009 |
| | 409 | Glucose | 60.0 | NaSO$_4$ | 15.0 | 10.0 | 0.0 | 0.05 | 1.41 | 20.14 | 0.0109 |
| ❸ | 410 | Glucose | 60.0 | Sea salt | 5.0 | 10.0 | 0.0 | 14.6 | 59.23 | 31.44 | 4.6004 |
| | 411 | Glucose | 60.0 | Sea salt | 15.0 | 10.0 | 0.0 | 10.8 | 51.01 | 26.17 | 2.8144 |
| | 412 | Glucose | 60.0 | Sea salt | 37.5 | 10.0 | 0.0 | 15.9 | 69.32 | 25.32 | 4.0194 |
| | 413 | Glucose | 60.0 | Sea salt | 75.0 | 10.0 | 0.0 | 10.8 | 61.02 | 25.25 | 2.7356 |
| | 414 | Glucose | 60.0 | Sea salt | 100.0 | 10.0 | 0.0 | 11.8 | 68.21 | 24.02 | 2.8290 |
| | 415 | Glucose | 60.0 | Sea salt | 125.0 | 10.0 | 0.0 | 11.2 | 59.63 | 22.56 | 2.5256 |
| ❹ | 416 | Glucose | 5.0 | Sea salt | 15.0 | 10.0 | 0.0 | 0.63 | 5.21 | 29.18 | 0.1844 |
| | 417 | Glucose | 20.0 | Sea salt | 15.0 | 10.0 | 0.0 | 4.06 | 29.59 | 24.01 | 0.9752 |
| | 418 | Glucose | 40.0 | Sea salt | 15.0 | 10.0 | 0.0 | 9.91 | 59.39 | 23.88 | 2.3665 |
| | 419 | Glucose | 60.0 | Sea salt | 15.0 | 10.0 | 0.0 | 10.76 | 51.01 | 26.17 | 2.8144 |
| | 420 | Glucose | 100.0 | Sea salt | 15.0 | 10.0 | 0.0 | 12.79 | 69.50 | 31.55 | 4.0344 |
| | 421 | Glucose | 160.0 | Sea salt | 15.0 | 10.0 | 0.0 | 1.00 | 9.40 | 30.01 | 0.3013 |
| ❺ | 422 | Glucose | 5.0 | Sea salt | 15.0 | 10.0 | 0.0 | 0.62 | 12.74 | 29.86 | 0.1866 |
| | 423 | Glycerol | 5.0 | Sea salt | 15.0 | 10.0 | 0.0 | 0.52 | 18.84 | 35.07 | 0.1836 |

Figure 3:
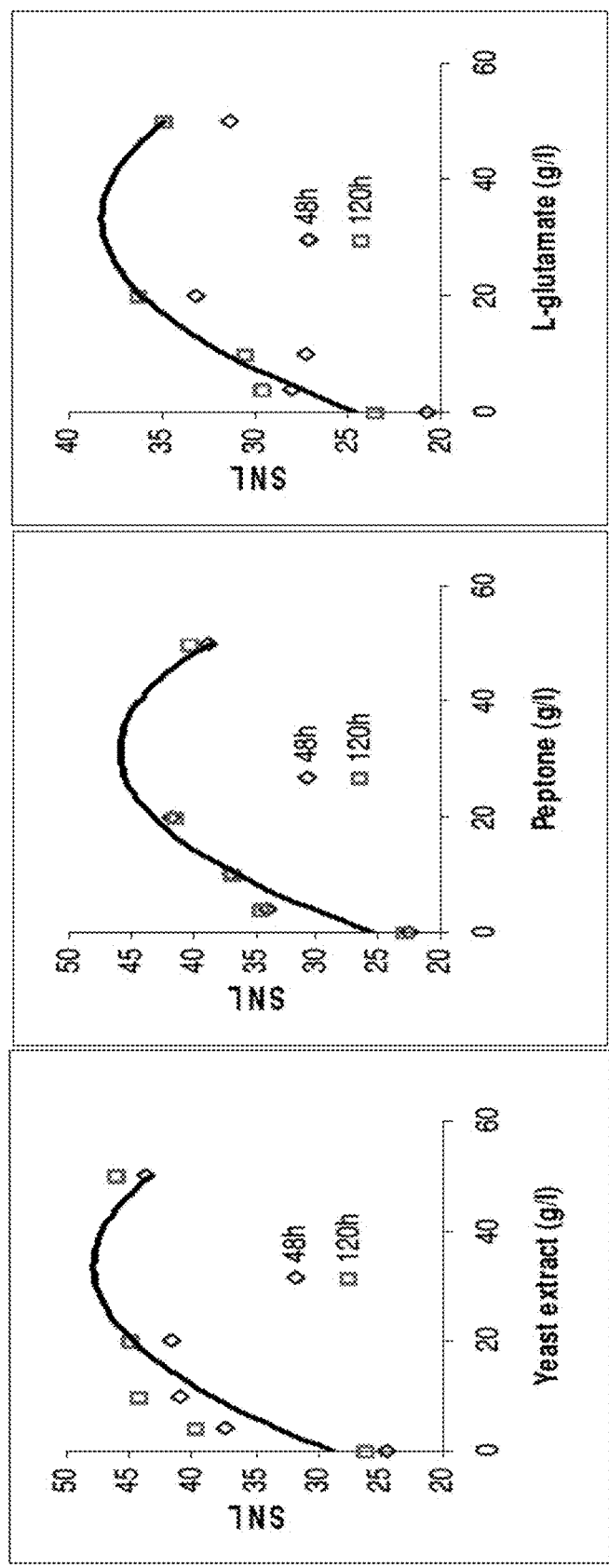
FIG. 3 shows a scatter plot graph of results from ONC-T18 biomass optimization experiments performed. These experiments used a technique known as the Taguchi method in order to determine the optimal conditions for growth of ONC-T18 under various media conditions.
Figure 4:
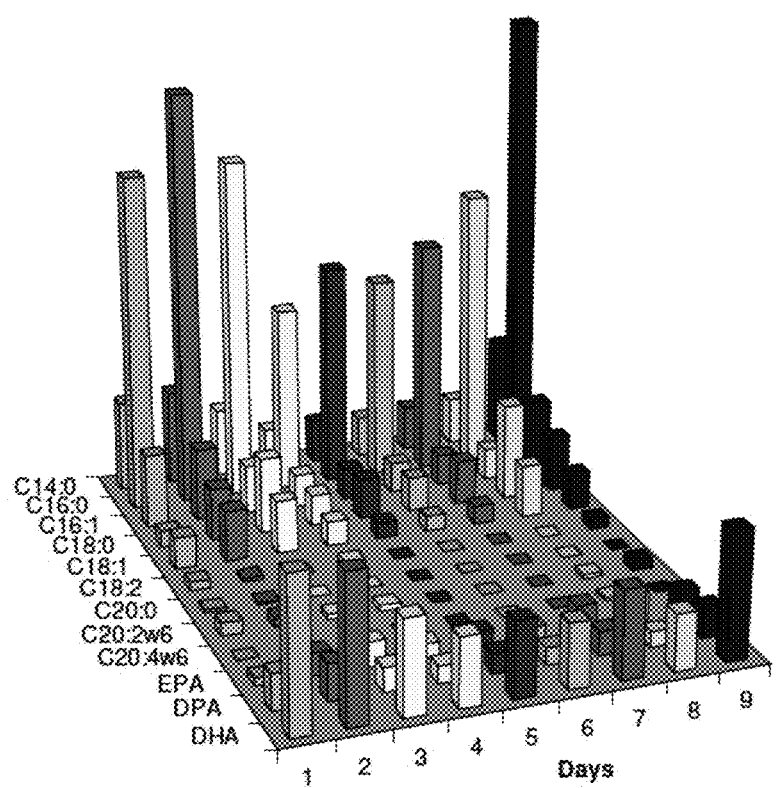
FIG. 4 shows a bar graph of the fatty acid profile of ONC-T18, grown under optimal conditions (example 4) over a nine day period.

5. Example 5: Optimal Time for Harvesting of ONC-T18 for Maximal DHA Production ONC-T18 was cultured under the same media composition and conditions as those shown within example 1. Of interest in this particular instance is the time at which ONC-T18 should be harvested in order to gain the maximal amounts of DHA, DPA and EPA as well as taking into account the time necessary to gain said amounts (see FIG. 3).

Time course experimental results showed that the optimal time for harvesting ONC-T18 for optimal DHA production within flask and bioreactor varied between 3 and 5 days, respectively.

6. Example 6: Analysis of Lipids Derived from ONC-T18

The total lipid fraction of ONC-T18 was extracted using a modified Bligh & Dyer method. Specifically, 2.0 g of dried cell biomass was rehydrated overnight at 4° C. in 8 ml of distilled $H_2O$. 30 ml of methanol:chloroform (2:1 vol/vol) was added to mixture and gently shaken at 120 rpm for 20 min, with resultant supernatant decanted. Pellet was then Analysis of results shows that the fatty acid component which ONC-T18 produces under heterotrophic fermentation is almost entirely triglyceride (at least 95%) in nature. In addition to the neutral fatty acid fraction mentioned above. ONC-T18 also produces a discernable carotenoid and phospholipid fraction. On subsequent isolation of the phospholipid fraction, first via a 50% and then a 75% burn followed by solvent-based separation, it was determined that a large and complex phospholipid fraction was present. Results showed the present of phosphotidylcholine, phosphotidylserine and phosphotidic acid components within the sample.

7. Example 7: Production of Antioxidants Using the Strain, ONC-T18

The eukaryote, ONC-T18 was cultured using conditions and medium as mentioned previously. The resultant cellular biomass after heterotrophic fermentation is collected via centrifugation, filtration or settling. Cells were harvested by centrifugation at 3800×g and washed with phosphate buffered saline. The cellular biomass (fresh or freeze-dried) was suspended in 10× volume of acetone, agitated for 5 minutes at 200 rpm, centrifuged at 3800×g for 5 minutes and concentrated to dryness by $N_2$ evaporation. The pigments were then immediately resuspended in a minimal amount of 10% acetone in hexane and stored at −20° C. until HPLC analysis. Identification of carotenoid extracts was then carried out on an Agilent 1100 HPLC (Agilent, Palo Alto, Calif., USA) equipped with a variable wavelength detector set at 470 nm. Samples were injected through a Symmetry C18 guard column (Waters, Milford, Mass., USA) to a Bondclone C18 reverse-phase column (Phenomenex, Torrance, Calif., USA; 10 μm particles; 3.9×300 mm i.d.). The injection volume was 10 μl and a flow of 1.00 ml/min 10% acetone in hexane over a 25 minute period was used. Quantitative data of carotenoids was based on comparison of the peak area with known standards (in this case astaxanthin, canthaxanthin, β-cryptoxanthin, zeaxanthin, echinenone and β-carotene; ChromaDex, Santa Ana, Calif., USA). In the absence of a known standard such as in the case of the carotenoid, phoenicoxanthin, the astaxanthin peak area was used to calculate its concentrations. Carotenoid identity was further confirmed via HPLC-MS using a Waters HPLC equipped with a photo-diode array (Waters model 996) leading into a Micromass ESI-Q-T of Mass spectrometer (Waters, Milford, Mass., USA). HPLC analysis of ONC-T18 subsequently revealed the presence of several antioxidant compounds (between 50 to 1250 mg kg$^{-1}$) within the cellular biomass. These compounds included the antioxidant carotenoids astaxanthin, zeaxanthin, canthaxanthin, echinenone and beta-carotene in the range of 1 to 20 mg kg$^{-1}$, 0.25 to 10 mg kg$^{-1}$, 1 to 20 mg kg$^{-1}$ 1 to 20 mg kg$^{-1}$ and 1 to 200 mg kg$^{-1}$, respectively, as well as several unidentified flavenoid polyphenolic compounds.

8. Example 8: Comparison with Known Microorganisms

The ability of ONC-T18 to produce DHA, EPA and DPA was compared with that of known microorganisms. The amount of cellular biomass per liter of medium, the percent content of fats or fatty acids per dried cell biomass, the percent content of DHA, EPA and DPA in total fatty acids, and the amount of DHA, EPA and DPA obtained when DHA, EPA and DPA are produced by cultivation of *Thraustochytrium aureum* ATCC 34304, *Thraustochytrium* sp. ATCC 20891, *Thraustochytrium* sp. ATCC 20892, *Thraustochytrium roseum* ATCC 28210, *Thraustochytrium* sp. ATCC 26185, *Schizochytrium* sp. ATCC 20888, *Schizochytrium aggregatum* ATCC 28209 and *Schizochytrium limacinum* MYA-1381, as well as when DHA, EPA and DPA are produced by cultivation of ONC-T18 according to the present invention.

TABLE 5

Comparison of the lipid production and biomass characteristics of several representative Thraustochytrid strains.

| Microorganism | Cellular biomass amount (gl$^{-1}$) | Percent lipid content (% g$^{-1}$) | Percent content of DHA (% g$^{-1}$) | Percent content of EPA (% g$^{-1}$) | Percent content of DPA (% g$^{-1}$) | Total DHA (gl$^{-1}$) | Total EPA (mg l$^{-1}$) | Total DPA (mg 1-1) |
|---|---|---|---|---|---|---|---|---|
| *Thraustochytrium* sp ATCC 20891 | 1.8 | no data | 12 | no data | no data | no data | no data | no data |
| *Thraustochytrium* sp ATCC 20892 | 3 | 7 | 35 | no data | no data | 0.07 | no data | no data |
| *Thraustochytrium* sp ATCC 26185 | 2.3 | no data | 41.9 | 3.1 | 10 | no data | no data | no data |
| *T. aureum* ATCC 34304 | 4-5 | 8-20 | 24-51 | 3.6-9.3 | no data | 0.1-0.5 | 0.0001 | no data |
| *T. roseum* ATCC 28210 | 8-17 | 18-25 | 50 | no data | no data | 0.6-2.1 | no data | no data |
| *Schizochytrium* sp. ATCC 20888 | 10.5 | 50 | 25-37 | no data | no data | 1.95 | no data | no data |
| *S. aggregatum* ATCC 28209 | 1.4 | 1.7 | 6.0 | 6.1 | no data | 1 | 1 | no data |
| *S. limacinum* SR21 MYA-1381 | 23-40 | 40-53.5 | 29.7-34 | 0.2-0.4 | no data | 3.0-7.2 | 0.08 | no data |
| ONC-T18 | 25-55 | 45-80 | 24-34.2 | 0.1-2 | 6-10 | 4.6-13 | 0.2-0.8 | 0.9-3.8 |

As shown in Table 5, it is apparent that, when cultivation is carried out using ONC T18 according to the present invention, the cellular biomass values per liter medium were extremely high as compared with the other strains tested. Moreover, according to the present invention, ONC-T18 has a very high percent content of lipids compared with the other strains mentioned above. Furthermore, according to the present invention, the percent content of DHA and DPA within ONC-T18 is extremely high, with EPA levels shown to be comparable to all strains screened. Thus, it appears that ONC-T18 has the ability to produce large quantities of DHA, EPA and DPA under fermentation conditions as mentioned within example 1.

9. Example 9: Alternative Carbon Source Information

ONC-T18 has been shown to grow preferentially on media where the main nitrogen sources are yeast extract, sodium glutamate and/or peptone and the main carbon source is D-glucose. As a result of detailed metabolic profiling of ONC-T18 it was noted that glycerol (carbon source) was also a viable alternative. Furthermore, fish oil processing waste streams containing glycerol were also tested for applicability as low-cost nutrient alternatives. Experiments using 200 ml media in 500 ml flasks, grown at 25° C. for 3 days, 120 rpm in the case of the glycerol were undertaken. The glycerol content of two fish oil processing waste products, GWW (glycerol water wash) and GAW (glycerol acid wash), constituted 40% vol:vol of the 200 ml medium (adjusted to pH 6.5), while 6% glycerol was added to 200 ml medium (wt:vol) as control.

TABLE 6

Fatty acid, biomass and glycerol content for alternative carbon source study.

| | Percentage (%) fatty add to total lipid content by weight | | | | | TFA | Glycerol | Biomass |
|---|---|---|---|---|---|---|---|---|
| | AA | EPA | DHA | DPA n-3 | DPA n-6 | (mg g$^{-1}$) | (g L$^{-1}$) | (g L$^{-1}$) |
| 6% Glycerol (wt:vol) | 0.29 | 0.52 | 26.31 | 0.24 | 9.49 | 426.12 | 76.00 | 9.13 |
| 40% GAW (vol:vol) | 0.37 | 1.32 | 19.69 | 0.42 | 6.36 | 294.55 | 68.59 | 5.94 |
| 40% GWW (vol:vol) | 0.46 | 5.55 | 12.46 | 1.01 | 3.82 | 274.33 | 2.70 | 3.08 |

Analysis of these results has determined that the use of fish oil waste stream components, such as glycerol by-products, as carbon sources in large-scale fermentation of ONC-T18 while resulting in a reduced total fatty acid amount, represent a maintained DHA content within the microbial cells (FIG. 10).

10. Example 10: Multiplier of Dry Cell Weight

*Thraustochytrium* sp. ONC-T18 can be grown for the production of omega-3 oils in a variety of reactor configurations up to 100,000 L. All fermentations begin with the preparation of a 10-20% final volume inoculum, which is used to establish the fermentation culture. Initial medium configurations comprise up to 6 g/L sea salt, 10 g/L nitrogen source and 60 g/L carbon source, with fed-batch addition of another 75 g/L carbon source after 24 to 36 hours of initial fermentation for an additional 72 to 96 hours and occurs within the temperature range 18-25° C. For example, using the medium 6 g/L sea salt, 2 g/L yeast extract, 8 g/L L-glutamate and 60 g/L D-glucose (with an addition 75 g/L added after 36 hours), grown at 25° C. for 96 hours, ONC-T18 was able to produce 40 g/L dry cell weight (dcw), 80% (dcw) total fatty acid (TFA)/lipid fraction (between C14:0 and C24:0) and 30% (TFA) DHA. Similarly, it is possible to increase dry cell weight by multiplying both nitrogen and carbon media components to exact a similar multiplication effect on biomass without affecting either TFA or DHA contents. For example, using the medium 24 g/L sea salt, 8 g/L yeast extract, 32 g/L L-glutamate and 300 g/L D-glucose, grown at 25° C. for 312 hours, ONC-T18 was able to produce 80 g/L dry cell weight (dcw), 60% (dcw) total fatty acid (TFA)/lipid fraction (between C14:0 and C24:0) and 38% (TFA) DHA.

11. Example 11: Growth of *Thraustochytrium* Sp. ONC-T18 on Various Alternative, Carbon (C) and Nitrogen (N) Sources and the Effect on Dry Cell Weight and Lipids Growth of *Thraustochytrium* sp. ONC-T18 on a variety of low-cost nitrogen and carbon sources was investigated. Specifically, 50 ml of ONC-T18 was cultured in 250 ml flasks containing 6 g/L artificial sea salts, for 72 hours at 25° C. Carbon and nitrogen source concentrations are shown below with 2 g/L of each nitrogen source listed, used in conjunction with 8 g/L of L-glutamate (with the exception of fish meal where 4 g was used). Carbon sources were switched as indicated. All experiments were performed in triplicate; all extractions for fatty acid methyl ester analysis were performed in triplicate along with triplicate GC injections.

Results indicate that *Thraustochytrium* sp. ONC-T18 produces optimal dry cell biomass (i.e. greater than the two control media) when grown on the nitrogen sources EMD yeast extract and fish meal. Conversely, lipid was found to be less than control, while DHA was optimal using corn steep liquor and EMD peptone. Finally, the carbon source dextrose was found to increase lipid content, while fructose and dextrose producing high DHA content than the controls.

TABLE 7

Growth of *Thraustochytrium* sp. ONC-T18

| | Medium (salt 6 g/l, growth 72 hrs, 50 ml cultures) | C (g/l) | N (g/l) | dcw/l medium (g) | Lipid (mg/g) | Lipid (g/l) | DHA (mg/g) | DHA (g/l) | DHA (% lipid) |
|---|---|---|---|---|---|---|---|---|---|
| Nitrogen Sources | Corn Steep Liquor-MSG | 60 | 10 | 11.36 | 371.97 | 4.33 | 111.64 | 1.244 | 29.72 |
| | Cotton Seed-MSG | 60 | 10 | 9.99 | 297.08 | 2.70 | 45.20 | 0.500 | 16.94 |
| | EMD ™ YE-MSG | 60 | 10 | 15.49 | 343.90 | 5.02 | 70.68 | 0.786 | 20.70 |
| | EMD ™ YE | 60 | 10 | 35.79 | 189.01 | 6.76 | 37.14 | 0.448 | 19.65 |
| | EMD ™ Peptone-MSG | 60 | 10 | 11.70 | 379.48 | 4.19 | 83.50 | 0.926 | 23.33 |
| | Sigma ™ YE-MSG | 60 | 10 | 9.77 | 257.86 | 3.28 | 54.60 | 0.618 | 19.69 |
| | Sigma ™ YE | 60 | 10 | 10.39 | 341.98 | 3.53 | 58.30 | 0.629 | 17.01 |
| | Fermtech ™ YE-MSG | 60 | 10 | 13.99 | 269.53 | 3.82 | 56.97 | 0.664 | 21.10 |
| | Fermtech ™ YE | 60 | 10 | 17.07 | 243.23 | 4.15 | 48.01 | 0.530 | 19.74 |
| | Fish meal (62% protein) | 60 | 12 | 19.53 | 290.72 | 5.68 | 73.59 | 0.828 | 25.31 |
| Carbon Sources | Fructose | 60 | 10 | 14.57 | 498.54 | 8.09 | 96.97 | 1.070 | 21.55 |
| | Dextrose | 60 | 10 | 14.98 | 623.91 | 9.87 | 113.69 | 1.232 | 18.94 |
| | Corn Dextrin | 60 | 10 | 4.65 | 89.69 | 0.39 | 25.69 | 0.278 | 26.75 |
| | Gelatin | 60 | 10 | 7.09 | 31.87 | 0.13 | 11.86 | 0.127 | 27.70 |
| | Starch (corn) | 5 | 10 | 4.85 | 94.04 | 0.46 | 19.49 | 0.206 | 20.72 |
| | | 30 | 10 | 3.13 | 90.07 | 0.28 | 23.78 | 0.256 | 26.40 |

TABLE 7-continued

Growth of Thraustochytrium sp. ONC-T18

| Medium (salt 6 g/l, growth 72 hrs, 50 ml cultures) | C (g/l) | N (g/l) | dcw/l medium (g) | Lipid (mg/g) | Lipid (g/l) | DHA (mg/g) | DHA (g/l) | DHA (% lipid) |
|---|---|---|---|---|---|---|---|---|
| Starch (wheat) | 5 | 10 | 8.03 | 86.96 | 0.47 | 17.62 | 0.185 | 17.76 |
|  | 30 | 10 | 18.16 | 18.59 | 0.34 | 3.83 | 0.042 | 20.58 |
| Control medium (1) | 60 | 10 | 16.92 | 487.59 | 8.25 | 70.87 | 0.768 | 13.25 |
| Control medium (2) | 60 | 10 | 10.88 | 483.06 | 6.06 | 74.64 | 0.818 | 16.19 |

Abbreviations:
MSG = L-glutamate (sodium)
YE = Yeast extract

12. Example 12: Extraction Techniques for Isolation of Total Lipids and Fractions A variety of methods for the isolation of selected omega-3 oils were tested in order to determine optimal isolation efficiency. These methods included: the standard Bligh & Dyer method (Bligh & Dyer, Can J. Biochem. Physiol., 37:912-917, 1959); the combined extraction and transesterification method used specifically with Thraustochytrid species allowing for processing of samples for rapid GC FAME analysis (Lewis et al., J. Microbiol. Methods, 43:107-116, 2000); extraction by simultaneous saponification (Cartens et al., J. Am. Oil Chem. Soc. 73:1025-1031, 1996); and solid phase extraction using silica gel columns which can selectively isolate triglycerides, diglycerides and monoglycerides (Pinkart et al., J. Microbiol. Methods, 34:9-15, 1998; Bateman & Jenkins, J. Agric. Food Chem., 45:132-135, 1997).

Specifically, 40 grams of dry cell weight Thraustochytrium sp. ONC-T18 biomass produced in a single fermentation run (see example 1) was divided into 0.44 g lots and used for each technique. All techniques were performed in triplicate with efficiencies analyzed using fatty acid methyl ester determination via FID-GC, again in triplicate with triplicate runs per sample. Results demonstrate that total fatty acid content might vary between individual methods with fluctuations most probably due to solvent:compound saturation, biomass disruption considerations and other physical condition considerations (e.g. temperature and time).

TABLE 8

Extraction Techniques for isolation of total lipids and fractions.

Bligh and Dyer

|  | DHA | EPA | C14:0 | C14:1 | C15:0 | C16:0 | C16:1 | C18:1 | C20:0 | C20:4 | C22:5 | TFA |
|---|---|---|---|---|---|---|---|---|---|---|---|---|
|  | mg omega-3 per gram of biomass (mg/g) | | | | | | | | | | | |
| 1 | 104.39 | 4.25 | 36.28 | 5.82 | 113.94 | 77.27 | 4.92 | 44.01 | 1.13 | 1.67 | 28.86 | 430.99 |
| 2 | 136.75 | 5.45 | 46.51 | 7.40 | 142.96 | 98.38 | 6.07 | 56.49 | 1.40 | 2.19 | 37.92 | 552.98 |
| 3 | 134.59 | 4.78 | 42.51 | 6.91 | 128.54 | 87.01 | 5.20 | 51.10 | 1.30 | 2.10 | 35.98 | 532.91 |
| Av. | 125.24 | 4.83 | 41.77 | 6.71 | 128.48 | 87.55 | 5.40 | 50.53 | 1.28 | 1.99 | 34.25 | 505.63 |

Direct Transesterification

|  | DHA | EPA | C14:0 | C15:0 | C16:0 | C16:1 | C18:0 | C18:1 | C20:0 | C20:4 | C22:5 | TFA |
|---|---|---|---|---|---|---|---|---|---|---|---|---|
|  | mg omega-3 per gram of biomass (mg/g) | | | | | | | | | | | |
| 1 | 104.39 | 4.24 | 36.39 | 5.42 | 112.94 | 75.27 | 5.42 | 44.01 | 1.13 | 1.67 | 28.86 | 420.99 |
| 2 | 89.83 | 4.54 | 34.81 | 5.60 | 103.04 | 73.43 | 5.56 | 42.85 | 0.98 | 1.87 | 25.35 | 392.88 |
| 3 | 101.64 | 4.25 | 37.16 | 5.98 | 106.94 | 75.98 | 5.35 | 43.95 | 1.11 | 1.78 | 26.46 | 410.65 |
| Av. | 98.65 | 4.34 | 36.12 | 5.67 | 107.64 | 74.89 | 5.44 | 43.60 | 1.07 | 1.77 | 26.89 | 408.17 |

Simultaneous saponification

|  | DHA | EPA | C14:0 | C15:0 | C16:0 | C16:1 | C18:0 | C18:1 | C20:0 | C20:4 | C22:5 | TFA |
|---|---|---|---|---|---|---|---|---|---|---|---|---|
|  | mg omega-3 per gram of biomass (mg/g) | | | | | | | | | | | |
| 1 | 204.85 | 6.75 | 46.55 | 8.56 | 182.26 | 134.81 | 8.73 | 105.04 | 2.16 | 3.20 | 66.68 | 785.25 |
| 2 | 188.51 | 6.17 | 47.64 | 9.32 | 208.29 | 121.25 | 10.35 | 95.80 | 2.53 | 2.89 | 61.41 | 770.14 |
| 3 | 198.25 | 6.12 | 47.21 | 9.65 | 207.71 | 136.51 | 9.58 | 98.50 | 2.41 | 3.10 | 63.58 | 782.54 |
| Av. | 197.20 | 6.35 | 47.13 | 9.18 | 199.42 | 130.86 | 9.55 | 99.78 | 2.37 | 3.06 | 63.89 | 779.31 |

TABLE 8-continued

Extraction Techniques for isolation of total lipids and fractions.

| | \multicolumn{12}{c}{Solid phase extraction} | | | | | | | | | | | |
| --- | --- | --- | --- | --- | --- | --- | --- | --- | --- | --- | --- |
| | DHA | EPA | C14:0 | C15:0 | C16:0 | C16:1 | C18:0 | C18:1 | C20:0 | C20:4 | C22:5 | TFA |
| | \multicolumn{12}{c}{mg omega-3 per gram of biomass (mg/g)} | | | | | | | | | | | |
| 1 | 169.17 | 0.42 | 68.41 | 10.83 | 204.43 | 140.14 | 8.09 | 76.97 | 1.75 | 3.00 | 47.05 | 748.33 |
| 2 | 172.26 | 0.44 | 69.59 | 11.01 | 207.01 | 143.74 | 8.11 | 78.72 | 1.74 | 3.27 | 47.86 | 819.04 |
| 3 | 171.65 | 0.43 | 69.21 | 11.31 | 208.97 | 146.64 | 8.16 | 77.64 | 1.73 | 3.64 | 46.98 | 785.64 |
| Av. | 171.69 | 0.43 | 69.07 | 11.05 | 206.80 | 143.51 | 8.12 | 77.78 | 1.74 | 3.30 | 47.30 | 784.34 |

N.B: Each value listed above is the average of triplicate runs using FID-GC for FAME analysis

13. Example 13 a) Materials and Methods (1) Isolation and Maintenance of Thraustochytrids

Seventy marine samples including: *Spartina alterniflora*, *Zostera marina* and sediment were collected in eastern Canadian coastal sites from Nova Scotia, Prince Edward Island, New Brunswick, Newfoundland and Labrador between July and August 2002. Samples were placed in 20 mL vials containing 10 mL of sterile 0.2 μm filtered natural seawater and 300 mg L$^{-1}$ penicillin and 500 mg L$^{-1}$ streptomycin. Suspensions were baited with sterile pollen (*Acer* sp.) and incubated for 48 hours at 18° C., according to (Bremer, *Marine Mycology—A Practical Approach*, Fungal Diversity Press, Hong Kong, pp 49-61 (2000)). Pollen grains were then transferred by loop and streaked onto B1 agar plates (1 g L$^{-1}$ yeast extract, 1 g L$^{-1}$ peptone, 10 g L$^{-1}$ agar to 1 L natural seawater) containing antibiotics and incubated. Single, irregular, hyaline colonies made up of spherical or limaciform cells and atypical of either yeast or bacterial colonies were picked and sub-cultured at least three times on B1 plates for purity.

(2) Biomass Production for Fatty Acid Screening

To screen isolates for growth and fatty acid production, liquid medium was prepared using 0.2 μm filtered natural seawater containing 2 g L$^{-1}$ peptone (BD, Franklin Lakes, N.J., USA) and 2 g L$^{-1}$ yeast extract (BD, Franklin Lanes, N.J., USA), which was sterilized by autoclaving, followed by the addition of 5 g L$^{-1}$, 0.2 μm filter sterilized glucose (Sigma-Aldrich, St. Louis, Mo., USA) (Bowles et al., *J Biotechnol* 70:193-202 (1999)). A 30 mL volume culture was inoculated by loop from an agar plate and grown for 4 days at 18° C. on a shaker at 100 RPM. 5 mL of this culture was then used to inoculate a 95 ml culture incubated for a further 4 days (stationary phase). Cells were harvested by centrifugation at 4,500 RPM, rinsed with 5 mL of distilled water and re-centrifuged. The cell pellets were freeze dried, weighed and stored at −80° C. prior to derivatisation for fatty acid analysis.

(3) Preparation of Fatty Acid Methyl Esters (FAME)

Fatty acid methyl ester (FAME) extraction was via the direct transesterification method, modified from Lewis et al. (*J Microbiol Meth.* 43:107-116 (2000)). Specifically, 20 mg of freeze dried material and 3 ml of transesterification reaction mix (methanol:hydrochloric acid:chloroform (10:1:1 vol/vol)) were added. Cells were vortexed for 10 seconds to ensure even dispersal of biomass and placed at 90° C. for 120 minutes. Once transesterification was complete, samples were removed and allowed to cool to room temperature. Water (1 ml) was then added and vortexed for 10 seconds. FAMEs were then extracted via the addition of 3×2 ml aliquots of hexane:chloroform (4:1), vortexed for 10 seconds and allowed to sit until clear liquid separations were achieved.

(4) Gas Chromatographic (GC) Analysis of FAMEs

GC analysis of FAMES was carried out using two internal standards (200 μl each). One hexacosaenoic acid (C23:0) is added prior to transesterification and the other, nonadecaenoic acid (C19:0) added directly before analysis. Analyses was performed using an Agilent 6890 GC (Agilent Technologies, Palo Alto, Calif., USA) equipped with a 30 m×0.32 m internal diameter (0.25 μm film thickness) OMEGAWAX 320 fused-silica capillary column (Sigma-Aldrich, St. Louis, Mo., USA) and flame ionization detector (injection volume 1 μl, carrier gas H2 with a constant flow of 5.0 ml min-1 and set at 250° C., split ratio 50:1 to FID detector at 275° C.). Confirmation of FAME identity was performed using a Trace GC-DSQ mass spectrometer (Thermo Electron, Boston, Mass., USA) and comparison of retention times for laboratory standards.

(5) Genetic Identification

The genomic DNA was extracted using the MoBio UltraClean Microbial DNA Isolation Kit (MoBio Laboratories, Carlsbad, Calif., USA) according to manufacturer instructions. The oligonucleotide primers used in amplifying the 18S rRNA gene, were modified from Honda et al. (*J Eukaryot Microbial.* 46:637-647 (1999)) namely T18S 1F 5'CAACCTGGTTGATCCTGCCAGTA-3' (SEQ ID NO:2) and T18S5R 5'-TCACTACGGAAACCTTGTTACGAC-3' (SEQ ID NO:3). A 20-μl PCR reaction mixture contained 2U Biolase™ DNA polymerase (Bioline, Boston, Mass., USA), 1×NH$_4$ reaction buffer, 3 mM MgCl$_2$, 1M Betaine (Sigma-Aldrich, StLouis, Mo., USA), 200 μM of mix PCR nucleotides (Promega, Madison, Wis., USA), 1 μM of each forward and reverse primer (MWG Biotech., High Point, N.C., USA) and 100 ng of genomic DNA template. After an initial denaturation step for 3 minutes at 94° C., PCR amplification was performed using a Eppendorf Master Cycle Gradient thermal cycler (Eppendorf, Westbury, N.Y., USA), using a program of 45 seconds at 94° C., 30 seconds at 64° C. and 2 minutes at 72° C. for 30 cycles, followed by a 10 minute final extension at 72° C. The PCR product was purified using MoBio UltraClean PCR Clean-up Kit (MoBio Laboratories Inc, Carlsbad, Calif., USA) for direct sequencing (MWG Biotech., High Point, N.C., USA) using primers FA2, FA3, RA1, R (Mo et al., Mar Bio/140:883-889 2002), T18S1F and T18S5R. The resulting sequences were aligned and compared to nucleotide sequences of similar microorganisms stored in GenBank (Benson et al., Nucleic Acids Res 33:D34-38 (2005)) using DS Gene (Accelrys, San Diego, Calif., USA). A phylogenetic tree was subsequently generated using the Neighbor-Joining method (Saito and Nei, Mol Bioi Evo/4:406-425 (1987)), with the statistical significance assessed using 1,000 bootstrap resamplings (Felsenstein, Evolution 39:783-791 (1985)).

(6) Identification of Carotenoids

Cells were harvested by centrifugation at 3800×g and washed with phosphate buffered saline. Then resuspended in 10× volume of acetone (Sigma-Aldrich, St Louis, Mo., USA), agitated for 5 minutes at 200 RPM, centrifuged at 3,800×g for 5 mins and concentrated to dryness by $N_2$ evaporation. Followed by resuspension in a minimal amount of 10% acetone in hexane prior to HPLC analysis. Identifications were carried out on an Agilent 1100 HPLC (Agilent, Palo Alto, Calif., USA) equipped with a variable wavelength detector set at 470 nm. Samples were injected through a Symmetry $C_{18}$ guard column (Waters, Milford, Mass., USA) to a Bondclone $C_{18}$ reverse-phase column (Phenomenex, Torrance, Calif., USA; 10 µm particles; 3.9× 300 mm i.d.). The injection volume was 10 µl and a flow of 1 ml $min^{-1}$ 10% acetone in hexane over a 25 minute period was used. Carotenoid identity was further confirmed with mass spectrometry analysis (Micromass ESI-QT of MS, Waters, Milford, Mass., USA). Quantitative data for each carotenoid was based on the development of a calibration curve using standards (astaxanthin, zeaxanthin, canthaxanthin, echinenone and β-carotene) and comparing peak area with defined concentrations.

(7) Fermentation Optimization

The effect of carbon, nitrogen and sea salt on fatty acid and DHA production were examined using batch cultures in 250 ml Erlenmeyer flasks shaken at 130 RPM for 3 days at 25° C. Further cultivation studies were carried out using a Biostat® Bplus Twin 5 L Bioreactor (Sartorius BBI Systems Inc., Bethlehem, Pa., USA). A 100 ml inoculum was used to inoculate 4.9 L of medium in the bioreactor. Glucose concentration was measured using the Glucose (HK) Assay Kit (Sigma-Aldrich, St Louis, Mo., USA) according to the manufacturers instructions. The media constituents and the conditions employed in the bioreactor are detailed with the relevant results.

b) Results

A collection and screening process was developed whereby members of the protist family Labyrinthulida, especially the genus, *Schizochytrium* and *Thraustochytrium*, were isolated using pollen-baiting and selective bacteriological media. This study, covering 20 unique collection sites dispersed throughout Atlantic Canada, produced 68 pure strains, identified microscopically. Selection of oleaginous strains, having more than 20% of their cell dry weight being fatty acids, was based upon results of GC PUFA profiling, biomass productivity, maximal TFA, DHA and to a lesser extent EPA concentrations (FIG. 11), according to the method of (Lewis et al., *J Microbiol Meth* 43:107-116 (2000)). Values for biomass, TFA and subsequent DHA and EPA productivities ranged from 100 to 2300 mg $L^{-1}$, 27.1 to 321.14, 5.18 to 83.63 and 2.97 to 21.25 mg $g^{-1}$, respectively (FIG. 11).

All isolates which grew in liquid medium (54 out of 68), produced major amounts of omega-3 polyunsaturated fatty acid, particularly DHA which comprised between 22 and 80% of the total C20 to C22 content of these cells (FIG. 11). This confirms previous findings, whereby thraustochytrids isolated from cold temperate environments have fatty acid profiles with DHA being up to 53% of the total fatty acid present (Bowles et al., *J Biotechnol* 70:193-202 (1999) and Huang et al., *Mar Biotechnol* 5:450-457 (2003)). Of particular interest is ONC-T18 which produces up to 90% of its C20 to C22 content as DHA which is approximately 35% of the total intracellular fatty acids. This DHA content was shown to be equivalent to those of several commercial production strains, such as *Schizochytrium* sp. ATCC 20888 (32%) and *S. limacinum* MYA-1381/5R21 (34%) (Barclay et al, *J Appl Phycol* 6:123-129 (1994) and Yokochi et al., *Appl Microbiol Biotechnol* 49:72-76, (2003)). Furthermore, all isolates synthesized eicosapentaenoic acid (EPA), varying between 2 and 20% w/w of total PUFAs identified (FIG. 11). In addition to the omega-3 oils produced, approximately 80% of all isolates synthesized the omega-6 PUFAs, arachidonic acid (AA) or docosapentaenoic acids (DPA), at concentrations varying between 1 and 18% and 3 and 7% w/w, respectively (FIG. 11).

Huang et al. (*Mar Biotechnol* 5:450-457 (2003)) suggested that for 20 thraustochytrids isolated from the tropical coastal waters of Japan and Fiji, five polyunsaturated fatty acid profiles could be described, namely DHA/DPA (n-6), DHA/DPA/EPA, DHA/EPA, DHA/DPA/EPA/AA and DHA/DPA/EPA/AA/docosatetraenoic acid (Huang et al., *Mar Biotechnol* 5:450-457 (2003)). In the case of this collection of thraustochytrids, isolated from the temperate waters of Atlantic Canada, four PUFA profiles could be determined, three of which 25 are identical to those mentioned above, namely DHA/DPA/EPA at 7.4% of collection, DHA/EPA at 13% of collection and DHA/DPA/EPA/AA, 74%, with a forth comprising a mixture of DHA/EPA/AA at 5.6%.

Through direct sequencing of the 18S rDNA gene, ONC-T18 was positively identified as a member of the *Thraustochytrid* family (GenBank Accession Number: DQ374149). Phylogenetic analysis indicated that ONC-T18 formed a unique group (97.5% identity) with *Thraustochytrium striatum* T91-6 (FIG. 12) (Leander and Porter, Mycologia 93:459-464 (2001)). While *Thraustochytriidae* sp. MBIC 11093, N1-27 and *Thraustochytrium* sp. CHN-1, collected from the coastal tropical waters of Japan, and found to be significant producers of DHA (Carmona et al., *Biosci Biotechnol Biochem* 67:884-888 (2003) and Huang et al., *Mar Biotechnol* 5:450-457 (2003)), were shown to be 96, 95.5 and 94.5% similar, respectively. Genetic diversity is quite low between all members of the *Thraustochytriidae* shown in FIG. 12, ranging from 97.5-91.0% similarity throughout. Yet, these species are globally distributed, with two-thirds isolated from the tropical coastal waters of Japan, China and Israel and the remaining from temperate waters off America, Europe and Canada.

The fatty acid profile of ONC-T18 included high contents of C22 PUFA, very low levels of C18 and C20 FA, and the occurrence of odd-chain saturated fatty acids (15:0 and 17:0), similar to that of *Schizochytrium* sp. KH105 or *S. limacinum* SR21. Furthermore, analysis of carbon and nitrogen utilization profiles for strains ONC-T18, SR21 and KH105 showed a similar pattern of assimilation. The content of n-6 DPA in strain ONC-T18 ranged from 6-10%, which seems to be extremely high when considering the limited occurrence of n-6 DPA in the biosphere. Similar levels of n-6 DPA were reported however, by Nakahara et al. (*J Am Oil Chem Soc* 73:1421-1426 (1996)) in *Schizochytrium* sp. SR21 (6-10%) and Ellenbogen et al. (*Comp Biochem Physiol* 29:805-81 (1969)) in *T. aureum* (9.5%) and *T. roseum* (6.6%).

Analysis of the fatty acid profile of ONC-T18 under three different culture configurations: (1) agar plate; (2) conical flask and (3) bioreactor and grown on the same medium (FIG. 13), shows a decrease in the diversity of PUFAs present and an overall increase in TFA from agar plate to bioreactor. Specifically, agar plates exhibited an array of PUFAs, while the flask and bioreactor grown cultures were dominated by one or two intermediates (FIG. 13). Compared to *Thraustochytrium aureum*, which grew better in flask culture than in a stirred tank fermenter (Ilda et al., *J Ferment Bioeng* 81:76-78 (1996)), ONC-T18 grew better in a bioreactor. This result is in agreement with that of (Nakahara et al., *J Am Oil Chem Soc* 73:1421-1426 (1996)), who found that *Schizochytrium* sp. SR21 showed high resistance to mechanical stirring, and therefore thrived under bioreactor conditions.

Furthermore, carotenoid pigments were found to be produced in plate, flask and bioreactor fermentations of *Thraustochytrium* sp. ONC-T18, resulting in a pale orange discoloration. Production of these antioxidants is maximal within bioreactor fermentations concurrently with fatty acid production. Moreover, through the use of HPLC mass spectrometry, it was determined that these antioxidant compounds were identified as astaxanthin, zeaxanthin, canthaxanthin, echineone and β-carotene (FIG. 14), being conjugated to various PUFAs. Similar results were reported amongst members of the *thraustochytid* group of protists. Specifically, *Schizochytrium aggregatum* was shown to produce echinenone and canthaxanthin (Valadon, *Trans Br Mycol Soc* 67:1-15 (1976)), while Carmona et al. (*Biosci Biotechnol Biochem* 67:884-888 (2003) and Huang et al. (*Mar Biotechnol* 5:450-457 (2003)) demonstrated the production of astaxanthin, echineone, canthaxanthin, phoenicoxanthin (not zeaxanthin as in ONC-T18) and 0-carotene by *Thraustochytrium* sp. CHN-1, a close relative of ONC-T18 (FIG. 12). In this study, concentrations of these carotenoids were found to be an order of magnitude less than those of CHN-1 with the major compound being β-carotene, rather than astaxanthin. Thus, within *Thraustochytrium* spp., PUFA and carotenoid production can be linked so that the storage fats being produced may be protected from oxidation.

Previously, it has been determined that the relative amounts of the principal fatty acid components (myristic, palmitic and oleic acids) may be altered somewhat by changing the growth conditions of the culture (Ilda et al., *J Ferment Bioeng* 81:76-78 (1996)). In this way, one can manipulate the final fatty acid composition and hence, physical properties of the desired PUFA in a controlled fashion during fermentation (Sijtsma et al., *Recent Res Devel Microbiol* 2:219-232 (1998)). In an attempt to limit the factors inhibiting both biomass and omega-3 PUFA production in ONC-T18, carbon, nitrogen and sea salt components in nutrient media were manipulated (Table 9), along with duration of culture (FIG. 15).

TABLE 9

Mean biomass production (SD ≤ 15%), total fatty acid (TFA) and DHA content of *Thraustochytrium* SP. ONC-T18.

| Glucose (g $L^{-1}$) | Biomass (g $L^{-1}$) | TFA (% biomass) | DHA (% TFA) | DHA (g $L^{-1}$) |
|---|---|---|---|---|
| 5 | 12.13 | 5.21 | 29.18 | 0.18 |
| 20 | 13.73 | 29.59 | 24.01 | 0.98 |
| 40 | 16.69 | 59.39 | 23.88 | 2.37 |
| 60 | 21.08 | 51.01 | 26.17 | 2.81 |
| 100 | 18.40 | 69.49 | 31.55 | 4.03 |
| 160 | 10.68 | 9.40 | 30.01 | 0.30 |

| YE (g $L^{-1}$) | MSG (g $L^{-1}$) | Biomass (g $L^{-1}$) | TFA (% biomass) | DHA (% TFA) | DHA (g $L^{-1}$) |
|---|---|---|---|---|---|
| 10 | 0 | 22.33 | 34.53 | 20.20 | 1.56 |
| 8 | 2 | 22.81 | 44.00 | 17.52 | 1.72 |
| 6 | 4 | 22.64 | 50.69 | 16.23 | 1.86 |
| 4 | 6 | 24.46 | 69.07 | 24.19 | 4.09 |

TABLE 9-continued

Mean biomass production (SD ≤ 15%), total fatty acid (TFA) and DHA content of *Thraustochytrium* SP. ONC-T18.

| | | | | | |
|---|---|---|---|---|---|
| 2 | 8 | 26.09 | 81.73 | 20.99 | 4.47 |
| 0 | 10 | 7.50 | 1.97 | 28.81 | 0.04 |

| Sea salt (g $L^{-1}$) | Biomass (g $L^{-1}$) | TFA (% biomass) | DHA (% TFA) | DHA (g $L^{-1}$) |
|---|---|---|---|---|
| 2 | 24.70 | 59.23 | 31.44 | 4.60 |
| 6 | 21.08 | 51.01 | 26.17 | 2.81 |
| 15 | 22.90 | 69.32 | 25.32 | 4.02 |
| 30 | 17.76 | 61.02 | 25.25 | 2.74 |
| 40 | 17.27 | 68.21 | 24.02 | 2.83 |
| 50 | 18.77 | 59.63 | 22.56 | 2.53 |

Within this study, as the concentration of nitrogen decreased, total fatty acid content increased, with the highest total fatty acid content (approximately 80%) obtained at 1% concentration of yeast extract and or monosodium glutamate (w/v). Cultures with a low nitrogen concentration, however, also limited cell growth and hence total fatty acid production. Optimal production in this experiment was obtained using 8 g $L^{-1}$ monosodium glutamate and 2 g $L^{-1}$ yeast extract, producing 26.1 g $L^{-1}$ biomass and 4.5 g $L^{-1}$ DHA (Table 9). Furthermore, increases in carbon up to 100 g $L^{-1}$ effectively increased DHA yield, this is in agreement with results obtained for *Schizochytrium* sp. SR21 (Yokochi et al., *Appl Microbiol Biotechnol* 49:72-76, (2003)) and contrary to those shown in *T. aureum* where glucose concentrations above 10 g $L^{-1}$ were inhibitory (Ilda et al., *J Ferment Bioeng* 81:76-78 (1996)). Maximum DHA yields of more than 4.0 g $L^{-1}$ were obtained in glucose medium, with yields more than 5 times that of *T. aureum* (Bajpai et al., *J Am Oil Chem Soc* 68:509-514 (1991)) and *T. roseum* (Li and Ward, *J Ind Microbiol* 13:238-241 (1994)) and comparable to that of *Schizochytrium* sp. SR21 and KH105 (Aki et al., *J Am Oil Chem Soc* 80:789-794 (2003)). Finally, ONC-T18 exhibited classical euryhaline abilities, being able to withstand salinities ranging from 2.0 to 50.0 g $L^{-1}$, resulting in biomass productivity of 25-30% variability (Table 9). In the same experiment DHA g $L^{-1}$ values were found to vary up to 45% between optimal at 4.6 g $L^{-1}$ and minimal at 2.5 g $L^{-1}$ (Table 9).

The biomass, TFA and DHA produced by ONC-T18 over a 168 h period in a 5 L bioreactor are presented in FIG. 15. The growth curve depicted is typical of several achieved under identical conditions. Maximum biomass production was reached after 120 h, close to the point of carbon source (i.e. glucose) depletion. This was also the point at which total fatty acid content of the biomass reached a maximum at around 70% biomass. Interestingly, after only 24 h of cultivation, DHA content spiked to 30% total fatty acid, thereafter remaining constant at 20-25%. These results are consistent with those of other fatty acid producing *Thraustochytid* strains, yet there is disparity with regards to the rate at which these reactions occur.

c) Discussion

Previously most studies of Labyrinturomycota identified strains which are unable to store total fatty acid in amounts greater than 20% of biomass. For example, prior to the isolation of *Schizochytrium* sp. SR 21 which is able to accumulate up to 50% of biomass as fat, *T. aureum* was the best accumulator at 20% (Bajpai et al., *J Am Oil Chem Soc* 68:509-514 (1991)). ONC-T18, on the other hand, is able to accumulate up to 80% of its biomass as lipid.

For oleaginous micro-organisms such as ONC-T18 to accumulate oil, it typically should be grown in a culture medium with a limited amount of nitrogen (usually exhausted after 24 to 36 h) and abundant amounts of a carbon source. Once the nitrogen is depleted, the oleaginous microbes continue to assimilate the carbon source but are no longer able to undergo cell division due to a lack of nitrogen (thus preventing protein and nucleic acid synthesis). The result being the conversion of these carbon sources (i.e. sugars such as glucose) into storage oils. In this regard, ONC-T18 is considered to grow more slowly than other *Thraustochytrid* strains, such as G13 (Bowles et al., *J Biotechnol* 70:193-202 (1999) and Huang et al., *Mar Biotechnol* 5:450-457 (2003), yet it produces DHA at faster rates and demonstrates a unique ability to incorporate elevated amounts of total fatty acids. Finally, the ability of ONC-T18 to grow at very low salt concentrations with both high biomass and total fatty acid productivity is remarkable. Lending itself well to scale up by negating the corrosive nature of salt water on industrial fermentation equipment.

What is claimed is:

1. A composition comprising an isolated eukaryotic microorganism having an 18S sequence, wherein the 18S sequence has at least 97% identity to the sequence set forth in SEQ ID NO:1, and an artificial heterotrophic growth medium comprising a carbon source, a nitrogen source, inorganic salts and vitamins, wherein the microorganism in the composition produces a lipid or fatty acid fraction of at least about 30 wt. % to 80 wt. %.

2. The composition of claim 1, wherein the 18S sequence has at least 99% identity to the sequence set forth in SEQ ID NO:1.

3. The composition of claim 1, wherein the microorganism has ATCC Accession Number PTA-6245.

4. The composition of claim 1, wherein the microorganism comprises an omega 3 or omega 6 fatty acid.

5. The composition of claim 1, wherein the microorganism comprises a lipid or fatty acid fraction and wherein the lipid or fatty acid fraction comprises docosahexaenoic acid (DHA).

6. The composition of claim 1, wherein the microorganism is a *Schizochytrium* sp.

7. The composition of claim 1, wherein the microorganism is a *Thraustochytrium* sp.

8. The composition of claim 1, wherein the medium comprises a carbon source in an amount of from 1 to 60 g $L^{-1}$.

9. The composition of claim 1, wherein the microorganism medium comprises a carbon source in an amount of from 1 to 200 g $L^{-1}$.

10. The composition of claim 1, wherein the microorganism comprises neutral lipids.

11. The composition of claim 10, wherein the microorganism comprises at least 95% by weight of total lipids.

12. The composition of claim 1, wherein the 18S sequence contains at least one substitution modification relative to SEQ ID NO:1.

13. The composition of claim 12, wherein the 18S sequence has at least 99% identity to the sequence set forth in SEQ ID NO:1.

14. The composition of claim 12, wherein the microorganism comprises an omega 3 or omega 6 fatty acid.

15. The composition of claim 12, wherein the microorganism comprises a lipid or fatty acid fraction and wherein the lipid or fatty acid fraction comprises docosahexaenoic acid (DHA).

16. The composition of claim 12, wherein the microorganism is a *Schizochytrium* sp.

17. The composition of claim 12, wherein the microorganism is a *Thraustochytrium* sp.

18. The composition of claim 12, wherein the microorganism comprises neutral lipids.

19. The composition of claim 18, wherein the neutral lipids comprise at least 95% by weight of total lipids.

* * * * *